US007071386B2

(12) United States Patent
Bintrim et al.

(10) Patent No.: US 7,071,386 B2
(45) Date of Patent: Jul. 4, 2006

(54) *XENORHABDUS* TC GENE FOR PEST CONTROL

(75) Inventors: Scott B. Bintrim, Westfield, IN (US); Jon C. Mitchell, West Lafayette, IN (US); Ignacio M. Larrinua, Indianapolis, IN (US); Patricia C. Apel-Birkhold, Zionsville, IN (US); Susan B. Green, Nobleville, IN (US); Barry W. Schafer, Cicero, IN (US); Scott A. Bevan, Indianapolis, IN (US); Scott A. Young, Midland, MI (US); Lining Guo, Chapel Hill, NC (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 10/753,901

(22) Filed: Jan. 7, 2004

(65) Prior Publication Data

US 2004/0194164 A1   Sep. 30, 2004

Related U.S. Application Data

(60) Provisional application No. 60/441,717, filed on Jan. 21, 2003.

(51) Int. Cl.
*A01H 5/00* (2006.01)
*A01H 5/10* (2006.01)
*C12N 15/82* (2006.01)
*C12N 1/21* (2006.01)
*C12N 15/31* (2006.01)

(52) U.S. Cl. .................. 800/301; 536/23.7; 435/418; 435/252.3

(58) Field of Classification Search .............. 800/279; 536/23.7; 435/252.3
See application file for complete search history.

(56) References Cited

U.S. PATENT DOCUMENTS

| 5,173,419 | A | 12/1992 | Harman et al. |
| 6,048,838 | A | 4/2000 | Ensign et al. |
| 6,174,860 | B1 | 1/2001 | Kramer et al. |
| 6,277,823 | B1 | 8/2001 | Kramer et al. |
| 6,281,413 | B1 | 8/2001 | Kramer et al. |
| 6,590,142 | B1 | 7/2003 | Petell et al. |
| 2002/0078478 | A1 | 6/2002 | Ffrench-Constant |
| 2002/0147148 | A1 | 10/2002 | Ensign et al. |

FOREIGN PATENT DOCUMENTS

| WO | WO 95/00647 A1 | 1/1995 |
| WO | WO 97/17432 A1 | 5/1997 |
| WO | WO 98/08388 A1 | 3/1998 |
| WO | WO 98/08932 A1 | 3/1998 |
| WO | WO 98/50427 A1 | 11/1998 |
| WO | WO 99/03328 A1 | 1/1999 |
| WO | WO 99/42589 A2 | 8/1999 |
| WO | WO 99/54472 A1 | 10/1999 |
| WO | WO 00/30453 A2 | 6/2000 |
| WO | WO 00/42855 A1 | 7/2000 |
| WO | WO 01/11029 A1 | 2/2001 |
| WO | WO 02/94867 A2 | 11/2002 |

OTHER PUBLICATIONS

Schnepf et al., *Bacillus thuringiensis* and its pesticidal crystal proteins, Microbiol Mol Biol Rev.;62(3):775-806, 1998.*
Database Uniprot, "Putative chitinase—CHI" (Dec. 1, 2001). XP002289854, retrieved from EBI, Database Accession No. Q93RP3 (abstract).
Database Uniprot, "XptA2 protein—*Xenorhabdus nematophilus*" (Dec. 1, 2001), XP002289855, retrieved from EBI. Database Accession No. Q93RN7 (abstract).
Database Uniprot, "XptC1 protein—*Xenorhabdus nematophilus*" (Dec. 1, 2001), XP002289856, retrieved from EBI, Database Accession No. Q93RN8 (abstract).
Database Uniprot, "XptB1 protein—*Xenorhabdus nematophilus*" (Dec. 1, 2001), XP002289857, retrieved from EBI, Database Accession No. Q93RN9 (abstract).
Database Uniprot, "XptA1 protein—*Xenorhabdus nematophilus*" (Dec. 1, 2001), XP002289857, retrieved from EBI, Database Accession No. Q93RP0 (abstract).
Database Uniprot, "XptD1 protein—*X. nematophilus*" (Dec. 1, 2001), XP002289860, retrieved from EBI, Database Accession No. Q93RP4 (abstract).
Bowen et al., "Insecticidal toxins from the bacterium Photorhabdus luminescens," Science 280 (5372), 2129-2132 (1998).
Bowen, D. et al., insecticidal toxin complex protein TcaC (Photorhabdus luminescens), GENBANK Accession No. AAC38625 (Jun. 30, 1998).
Bowen, D., et al., insecticidal toxin complex protein TcbA (Photorhabdus luminescens), GENBANK Accession No. AAC38627 (Jun. 30, 1998).
Ffrench-Constant et al., "Photorhabdus toxins: novel biological insecticides," Current Opinions in Microbiol. (1999), p. 284-288, vol. 2.
Ffrench-Constant et al., "Novel insecticidal toxins from nemalode-symbiotic bacteria," Cell. and Mol. Life Sciences (May 2000), p. 828-833, vol. 57, No. 5 (abstract).
Ffrench-Constant et al., "A Genomic Sample Sequence of the Entomopathogenic Bacterium . . . " Appl. Environ. Microbiol. (Aug. 2000), p. 3310-3329, vol. 66, No. 8.
Forst et al., "Molecular Biology of the Symbiotic-Pathogenic Bacteria Xenorhabdus spp. and Photorhabdus spp.," Microbiological Reviews (Mar. 1996), p. 21-43, vol. 60, No. 1.

(Continued)

Primary Examiner—Anne Kubelik
(74) Attorney, Agent, or Firm—Saliwanchik, Lloyd & Saliwanchik

(57) ABSTRACT

The subject invention relates to novel nucleic acid encoding a *Xenorhabdus* strain Xwi toxin complex (TC) protein and plants and bacteria transformed therewith.

9 Claims, 5 Drawing Sheets

OTHER PUBLICATIONS

Merlo, D.J., et al., toxin A (*Photorhabdus luminescens*), GENBANK Accession No. AAF05542, Nov. 2, 1999.

Morgan et al., "Sequence Analysis of Insecticidal Genes from *Xenorhabdus nematophilus* . . . " Appl. Environ. Microbiol. (May 2001), p. 2062-2069, vol. 67, No. 5.

Morgan et al., *Xenorhabdus nematophilus* genes, GENBANK Accession No. AJ308438 (May 11, 2001).

Morgan et al., XptA1 protein (*Xenorhabdus nematophila*), GENBANK Accession No. CAC38401 (May 11, 2001).

Morgan, J.A., et al., XptB1 protein (*Xenorhabdus nematophila*), GENBANK Accession No. CAC38402 (May 11, 2001).

Morgan, J.A., et al., XptC1 protein (*Xenorhabdus nematophila*), GENBANK Accession No. CAC38403 (May 11, 2001).

Morgan, J.A., et al., XptA2 protein (*Xenorhabdus nematophila*), GENBANK Accession No. CAC38404 (May 11, 2001).

Toleman, M., exochitinase (*Sodalis glossinidius*), GENBANK Accession No. CAA72201 (Feb. 4, 1998).

Waterfield et al., "Oral Toxicity of Photorhabdus luminescenss W14 Toxin Complexes in *Escherichia coli*," Appl. Environ. Microbiol. (Nov. 2001), p. 5017-5024, vol. 67, No. 11.

Waterfield et al., "The tc genes of Photorhabdus: a growing family," Trends Microbiol. 9 (4), 185-191 (2001).

Waterfield et al., "Genomic islands in Photorhabdus," Trends Microbiol. 10 (12), 541-545 (2002).

Waterfield, N.R., et al., toxin complex protein (*Photorhabdus luminescens*), GENBANK Accession No. AAL18471 (Oct. 25, 2001).

Waterfield, N.R., et al., toxin complex protein (*Photorhabdus luminescens*), GENBANK Accession No. AAL18472 (Oct. 25, 2001).

Waterfield, N.R., et al., toxin complex protein (*Photorhabdus luminescens*), GENBANK Accession No. AAL18473 (gi:16416915), Oct. 25, 2001.

Waterfield, N.R., et al., TcdA1; toxin complex protein (*Photorhabdus luminescens*), GENBANK Accession No. AAL18486.

Waterfield, N.R., et al., TcdB1; toxin complex protein (*Photorhabdus luminescens*), GENBANK Accession No. AAL18487.

Waterfield, N.R., et al., TccC2 (*Photorhabdus luminescens*), GENBANK Accession No. AAL18492 (gi:27479639).

Waterfield, N.R., et al., TccC4 (*Photorhabdus luminescens*), GENBANK Accession No. AAO17196 (gi:27479669).

Waterfield, N.R., et al., TcdA2 (*Photorhabdus luminescens*), GENBANK Accession No. AAO17201.

Waterfield N.R., et al., TcdB2 (*Photorhabdus luminescens*), GENBANK Accession No. AA017202.

Waterfield, N.R., et al., TccC3 (*Photorhabdus luminescens*), GENBANK Accession No. AAO17204 (gi:27479677).

Waterfield, N.R., et al., TcdA4 (*Photorhabdus luminescens*), GENBANK Accession No. AAO17209.

Waterfield, N.R., et al., TccC5 (*Photorhabdus luminescens*), GENBANK Accession No. AAO17210 (gi:27479683).

* cited by examiner

Figure 1. Orientation of ORFs identified in pDAB2097

Figure 2. Expression Vector Plasmid pET280 Vector

Figure 3. Expression Plasmid pCot-3

Figure 4. Schematic Diagram of pET

*Photorhabdus*
*tca*
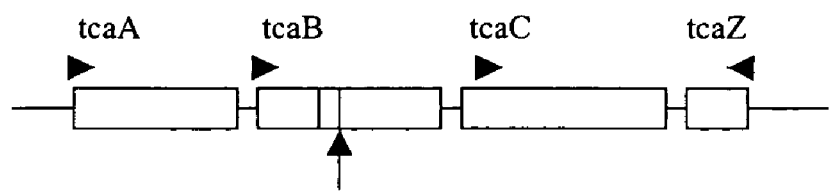
*tcb*
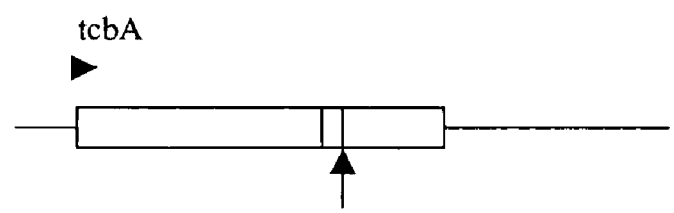
*tcc*
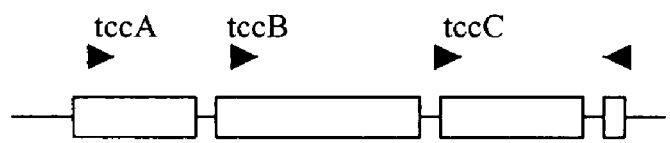
*tcd*
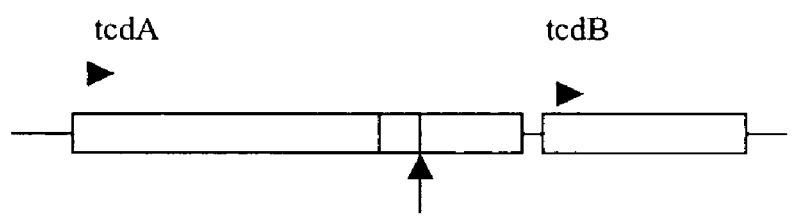
Fig. 5

SEQUENCE LISTING

```
<160> NUMBER OF SEQ ID NOS: 22

<210> SEQ ID NO 1
<211> LENGTH: 20
<212> TYPE: PRT
<213> ORGANISM: Xenorhabdus nematophilus

<400> SEQUENCE: 1

Met Tyr Ser Thr Ala Val Leu Leu Asn Lys Ile Ser Pro Thr Arg Asp
1               5                   10                  15

Gly Gln Thr Met
            20

<210> SEQ ID NO 2
<211> LENGTH: 5
<212> TYPE: PRT
<213> ORGANISM: Xenorhabdus nematophilus

<400> SEQUENCE: 2

Met Trp Tyr Val Arg
1               5

<210> SEQ ID NO 3
<211> LENGTH: 6
<212> TYPE: PRT
<213> ORGANISM: Xenorhabdus nematophilus

<400> SEQUENCE: 3
```

-continued

```
Leu Thr Gln Phe Leu Arg
1               5

<210> SEQ ID NO 4
<211> LENGTH: 10
<212> TYPE: PRT
<213> ORGANISM: Xenorhabdus nematophilus

<400> SEQUENCE: 4

Ala Asn Pro Gln Leu Ser Gly Ala Ile Arg
1               5                   10

<210> SEQ ID NO 5
<211> LENGTH: 8
<212> TYPE: PRT
<213> ORGANISM: Xenorhabdus nematophilus

<400> SEQUENCE: 5

Leu Leu Asp Gln Leu Ile Leu Arg
1               5

<210> SEQ ID NO 6
<211> LENGTH: 39005
<212> TYPE: DNA
<213> ORGANISM: Xenorhabdus nematophilus

<400> SEQUENCE: 6
gatcaggtat tcaatcaacc caaactgttt gatgaacctt tctttgttga taatcgtact      60
tttgattaca acgccattcg tggtaatgat gcacgaacaa ttaagcaact gtgcgccgga     120
ttgaaaatca ccgtagccac cttccaattg ttagctgagc aggtaaacac cgcctttcat     180
ctgccatccg gcaaattaac ctgttcactg cctgttattt cagcgcttta tcgtctggtg     240
actgttcctc ggttatttaa tttaaccgct gaacagggca tgatgctgat taacgcatta     300
aatgccagcg agaaattctc acctcatatt ctggctggtg agcctcgatt aagcctgtta     360
acaacagagg gttcagatac cacagaggtc gatttattgg atgttattct gatgttggaa     420
gaagttgctg tctggctgca acagagcaaa ctgaaaccgg aagaattctg cctgatgctg     480
caaagtgtta tgttgccggt ggttgccacg gacagcagtg tgacattctt cgacaacctg     540
ctgcaaggca ttcccaaaac cttactcaca gaagataact caacgcagg ggatatcccc      600 agactccctg aaggagaaac ctggtttgac aaactttcga tgctgataac cagcgatgga     660
ctcgtcaacg tttaccctct cagttggggc cagagtgatg aagattatct gaaatcagta     720
ttgacacctg tcgtcgaaaa aatcattagc gatccaaaca gtgtgattat cactgttttcc    780 gcattaacac aggtcattac tcaggcgaaa actgcgcagg aagatctggt ttccgccagc     840
gtgacacggg aatacggtac tggacgtgat atcgttcctt ggttattacg ctggattggc     900
agcagtgttc ccgatttcct tggcaaaatt tatatacaag cgcaaccag aggcggacac      960 ttgcgcactc cgccggatat cagcgctgaa ttactgcata tcacctatca tctggcgatg    1020
aataacatgc tgattaagca gttacgactc aaagctcaaa tcatttcatt acgtatcatc    1080
atgcctgaat ggctcggatt accaacgata gatggcagtc cgctatccgt gcatgaaatt    1140
tgggcactga gccggttccg taactgggcg accagctcat tgttcagtga agacgagtta    1200
atcgagtatt ttgcttttgc caatcagccg gagcaggacg ttcgtaacga tgaagatttt    1260
aatcgggact gtgctgaaaa gcttgccgac atactggaat gggatgccga tgaaattgag    1320
ctggcaaccc gacattttga tcctgccca gcacgtgcca gaaatatggg acaaattgac    1380
```

-continued

```
tggctgcgtc gtgtcatggc gttgtcgcgt cagactggcc tgtcagtgac accgttaatg    1440
acagccgcaa cgttaccgcc tttcccgccc tatgaccaga taacccatgt cggtgaagcg    1500
gtgattgcgg caacccagta cccatcagag gagtaaggaa cgatgagttc agttacccaa    1560
cctattgaag agcgtttact ggaatcacag cgcgacgcac tgctggattt ctatctcgga    1620
caggtcgttg cctattcacc tgacatgaca agtcagcgcg acaaaattaa ggatattgac    1680
gatgcctgcg actacctcct gctggatctg ctgacttccg ccaaagtcaa agcgacacga    1740
cttcacttg cgaccaattc attgcagcaa tttgtgaacc gcgtgtcact gaatattgaa    1800
cccggtttgt ttatgaccgc ggaagagagc gaaaattggc aggaatttgc gaatcgttat    1860
aattactggt ctgcggatcg cttattacgg acttatccgg aaagctatct ggaaccctg    1920
ttacgcctga ataaaacaga attcttcttc caactggaaa gtgcccttaa tcagggaaaa    1980
attaccgaag attccgtaca caagcggtg ctcggttatc tgaataattt tgaagatgtc    2040
agtaacctga aagttatcgc aggttatgaa gatggtgtta acatcaaacg cgataagttc    2100
ttctttgtcg gacgtacccg tacacagcca taccaatatt actggcgttc actgaatctt    2160
tcgatacgcc atcctgatac cgatgcgtta tctcccaatg cctggagcga gtggaaacct    2220
attgacctgc cattgggcag cgtagacccc aatttgatac gccccatttt cctgaataat    2280
cgcctgtata ttgcctggac ggaagttgaa gaacagtctg aaactaaaga tacaactgcg    2340
ttatcactgc ataaccaaaa cgttgagcct agtgcgggtg attgggttcc tcccacaccg    2400
ttcctgaccc ggatcaaaat cgcttatgcc aaatatgatg gcagctggag tacacccacc    2460
attctgcgcg aagacaatct gcaataccgg atggcccaga tggttgctgt gatggatata    2520
cagcaagacc gcataacccc gtttctggct ctggttccgt tgtccgtct tcaggggaca    2580
gataagaaag gtaaggatta tgattatgac gaagccttcg gttatgtctg cgatacactg    2640
ctggtagaaa ttactgattt gccggatgac gaatatgctg atggacgaaa aggaaaaat    2700
gtcggcaacc tggtctggta ttactcacgt gaacacaagg atgcagaagg caatcctatc    2760
gattaccgta ctatggtgct ctatccggca acccgggaag aacgctttcc tattgccgga    2820
gaagccaaac cggaaggaag ccctgatttt ggcaaagaca gtatcaaact gattgtcaat    2880
tttgttcatg gcactgatga cacactggag attgtcgctc aatctgactt taagtttggt    2940
gcgatagaag atcatcaata ttcaacggt tctttccggc tgatgcacga taatactgtc    3000
ttggatgaac aaccactggt actgaacgaa aaagttcctg atttaaccta tccatcaatc    3060
aagctggggt cggataatcg aatcaccctg aaagccgaac ttctctttaa gcccaaaggt    3120
ggtgttggca atgaaagtgc cagctgtact caagagttca gaatcggtat gcacattcgc    3180
gaactgatta aactcaatga acaggatcag gtgcaattcc tttccttccc cgcagatgaa    3240
actggtaacg cgccacaaaa cattcgcctt aatacactgt tgcaaaaaa actgatcgcc    3300
attgccagtc agggtatccc gcaggtactg agctggaata cacagcttat tactgaacaa    3360
cccataccc gttcattccc tacgccgatt gatttaaatg gcgcaaatgg gatctatttc    3420
tgggaactgt ttttccatat gccatttctg gtcgcgtggc gactgaatat cgaacaacga    3480
ttaaaagagg ccaccgaatg gctgcactat atttttaatc cgctggaaga tgaacttgtt    3540
caggccagca accaaggtaa accgcgttac tggaattcac ggccaattat tgatcctcca    3600
cccaccgtgt accggatgtt aattgaacca accgatccgg atgccattgc agccagtgaa    3660
cccattcact accggaaagc aatattccgt ttctatgtca agaatctgtt agatcaggga    3720
gacatggaat accgtaagct gacatccagt gcacgtactg tcgccaagca gatctatgac    3780
```

```
tccgtcaata tgttactggg taccagccct gatattctgc tcgcggcaaa ctggcaaccc    3840
cgtacgctgc aagatgtggc tctgtatgaa acagtgaag cacgggcaca ggagttaatg     3900
cttactgtca gcagcgtgcc acttctgcct gtgacatatg atacatccgt ctctgccgca    3960
ccgtctgatt tatttgtcaa acctgttgat acggaatatc tcaaactgtg caaatgttg    4020
gatcagcgtc tatataactt acgtcataac ctgaccttgg atggtaaaga gtttccggcc    4080
ggattatacg atgaacccat cagcccgcaa gatctgctca ggcagcgtta ccagcgtgtt    4140
gtggctaatc gtatggcggg catgaaacgc cgggcaatcc cgaattatcg tttcaccccg    4200
atcatgagcc gggcaaaaga ggccgcagaa acgctgattc agtacggcag cacgttactg    4260
agtttgctgg agaaaaaaga caataccgat tttgaacact tccgtatgca gcagcaactg    4320
ggctgtaca gctttacccg caatctgcaa cagcaagcga ttgacatgca acaggcttca     4380
ttggatgcac tgaccatcag ccgacgggcc gctcaggagc gccagcaaca ctataaatcg    4440
ctctatgatg aaaacatctc catcaccgag caggaagtta tcgcattaca atcaagagcg    4500
gctgaaggtg tgatcgctgc ccagtcagcc gccactgcgg ccgctgtggc ggatatggtt    4560
cccaatattt tcggtctggc cgtcgggggg atggtctttg gcggtatgct tcgggcaatc    4620
ggtgaaggaa tacgcattga cgttgaaagt aaaaatgcca aagccaccag cctgagcgtg    4680
tcagaaaatt accgtcgccg tcagcaagaa tgggagctgc aatacaaaca ggcggatatc    4740
aacattgagg agatcgacgc acagattggt atccagcaac gccaactgaa tatcagcaca    4800
acccaactgg cacaattgga agcccagcat gagcaggatc aagtcctgct ggagtactat    4860
tcaaaccgtt ttaccaatga tgcgttatac atgtggatga tcagccaaat ctccgggctt    4920
tacctgcaag cctatgatgc ggttaattcc ctctgtttac tggccgaagc ctcctggcag    4980
tacgaaacag gtcagtatga tatgaatttc gtccaaagtg gtctctggaa tgatctttat    5040
caggggctgc tggtcggaga acatctgaaa ttagccttac aacggatgga tcaggcgtat    5100
ttgcaacata caccagacg tctggagatc ataaaaacca tcggtaaaa atcattactg     5160
acatcatcac agtgggaaat tggcaagagt acgggttcat tcactttctt actgagcgcc    5220
gaaatgttct tgcgcgatta tccgacccac gctgatcggc gtataaaaac cgtagcgctg    5280
tcattgcccg cattgctggg gccttatgaa gatgtacggg cttcactggt acaactcagc    5340
aatacgcttt acagtactgc tgacttaaaa actatcgatt atttgcttaa ccccttggaa    5400
tacaccaaac ccgaaaacgt tttgctgaac gtacaggcta atcaaggtgt ggtgatttca    5460
acggccatgg aagacagcgg catgttcagg ctcaattttg atgatgaact tttcctgcct    5520
tttgaaggga caggcgccat ttcacagtgg aagttggaat tcggttccga tcaggatcag    5580
ctgctggagt cgctgagcga tattatcctc catctgcgtt ataccgcgcg tgatgtgagt    5640
ggcgaagta atgagttcag ccagcaggtt cgtagccgtc tgaataaaca tcaattaaaa    5700
caagacaatt ctaactgata tcaggagccg gccccggaat ataacggggc cggaagtgaa    5760
attatgtctc aaaatgttta tcgataccct tcaattaaag cgatgtctga cgccagcagc    5820
gaagtaggcg catctctggt tgcctggcag aatcaatctg gtggtcaaac ctggtatgtc    5880
atttatgata gcgcggtttt taaaaacatc ggctgggttg aacgctggca tattcccgac    5940
cgcaatattt cacctgattt accggtttat gagaatgcct ggcaatatgt ccgtgaggcg    6000
acaccggaag aaattgccga tcacggtaac cccaatacgc ctgatgtacc gccgggagaa    6060
aaaaccgagg tattgcaata tgatgcactc acagaagaaa cctatcagaa ggtgggatat    6120
```

-continued

```
aaacctgacg gcagcggaac tcctttgagt tattcttcag cacgtgttgc caagtccctg    6180
tacaacgaat atgaagttga tccggaaaat acagaaccgc tgcctaaagt ctctgcctat    6240
attactgact ggtgccagta tgatgcgcgt ttgtcgccag aaacccagga taacactgcg    6300
ctgaccagcg acgatgcccc cggccgtggt tttgatctgg aaaaaatccc gcctaccgcc    6360
tacgaccgcc tgattttcag ttttatggcc gtcaacggtg ataaaggcaa gttatccgaa    6420
cggattaatg aggttgttga cggtggaac cggcaagcag aagccagcag tggccagatt    6480
gcccctatta cattaggcca tattgtaccc gttgatcctt atggtgattt aggcaccaca    6540
cgcaatgtcg gtctggacgc ggatcagcgc cgtgatgcca gcccgaagaa tttcttgcaa    6600
tattacaatc aggatgcagc ctccggttta ctgggggat tgcgtaatct gaaagcgcga    6660
gcaaaacagg cagggcacaa gctggaactc gcattcagta tcggcggctg gagtatgtca    6720
gggtatttct ctgtgatggc caaagatcct gagcaacgtg ctacatttgt gagtagcatc    6780
gtcgacttct tccggcgttt tcccatgttt actgcggtgg atatcgactg gaataccccc    6840
ggcgccacag gtgaagaagg taatgaattc gacccggaac atgatggccc aaactatgtt    6900
ttgttagtga aagagctgcg tgaagcactg aacatcgcct ttggaacccg ggcccgtaaa    6960
gaaatcacga tagcctgtag cgccgtcgtt gccaaaatgg agaagtccag cttcaaagaa    7020
atcgcacctt atttagacaa tatctttgtg atgacctacg acttctttgg taccggttgg    7080
gcagaataca tcggtcacca tactaacctg tatcccccca gatatgaata tgacggcgat    7140
aaccctcctc cgcccaatcc tgatcgggac atggattact cggctgatga ggcgatccgc    7200
ttttttactgt cacaaggtgt acaaccggag aaaattcacc tcggatttgc taactatgga    7260
cgttcatgtc tgggtgctga tctgacaact cgccgctata acagaacagg agagccactg    7320
ggcacgatgg aaaaaggtgc tccggaattc ttctgtctgc tgaataacca atacgatgcg    7380
gaatatgaaa ttgcacgcgg gaaaaatcag tttgaactgg tgacagacac ggaaaccgac    7440
gctgacgcac tctttaatgc tgacggtggt cactggattt cactggatac gccccgcact    7500
gtgctgcata aggaattta tgcaaccaaa atgaaattgg gcgggatctt ctcttggtca    7560
ggcgatcagg atgatggcct gttggcaaat gctgctcacg aaggtttggg ttacttacct    7620
gtacgcggaa aagagaagat tgatatggga ccgttatata caaaggacg tctcattcag    7680
cttcctaaag taacccgtcg taaatcgtag taaataaaat tttccggtgg cctcacaggg    7740
gtcaccatat cctgctgtga aaagcgtat ccatttaatg ctttaacgct tcaattttct    7800
cccggctcag gccggtactg gtgacaatga tgtccagact gacaccatgc cgtaataatg    7860
cgcgcgccgt ttccagcttg ccttcttccc gtccttcagc tctgccttct gttctgcctt    7920
cagccctgcc ttcgtccgg ccttgctcac gccctttttg ttcaagctgt tctgcaatag    7980
tcatcaacat ggtttcatgc tccggagatt gttcagtcag ttgatggaca aactgggcga    8040
gatccagcgt atgtccattc agtaaaatat agcttaacac aacatggcgc tgttcggcgc    8100
tattataacc ggcattcaac aacgccacta ttggggaac ccactccagc atatcccggc    8160
aacggatatg ttttgtacc agctccatca aggcaatgct tttatgtgtc aggatctctt    8220
catcactgag cgcactgata tccaccaacg gcagggctg attatacagg tgagccgcgt    8280
gttcagagag tgtaaaacaa tccagccatc gatttgagta agggtaaggc ctcacctcac    8340
catgataaaa cagcaggggg acgaccaaag ggagttcagt atgtcctttt ttcagatgcg    8400
cagccatggc tgacagcgaa taatacatca gccgccaggc cattaacgga tcaggcgtgg    8460
actggtgttc aatcaggcaa taaatgtaac cgtccccgtg ggttgtctcg acagaataca    8520
```

```
gcacatcact gtgcaactga cgtaattgcc tgtccacaaa gctgccgggt tccagtttta   8580
gtgtggttaa atcacacact gaccggatcg cttccggcag ataaagggat aaaaattccc   8640
gggcggtttc tggttgggtt aaaaaatgtt tgaataacgc gtcatggtga ggcttttttg   8700
ctttcctggc cacaatccgt ctctctgttt tatcgttat taatcgcctt tactgccaaa    8760
gctatcatct cgctgaaaaa tccacagcca atatacaaca tattatctgc tgacccaaca   8820
ctcgtccggc taatcaatcc agtatcaatg cgagttctac agtaaataca gctcttcatg   8880
gtcaggaaac cggacaaaag ttgattgaat tccctaacca tgaattttct gttatgttaa   8940
ttattaccgt ctcacaataa taatcacatc aacagaatt tatttactat ataaataaac    9000
tatcaattat tataagaaaa ataatatgat tggcattaaa tataaaacca taaaaaagta   9060
gaattaattt ttaaaactta attgcagaaa ccagatgaaa tataaactta atttcttatc   9120
cataaataat aatgaatcaa tatttattca ataccatcag tggaaggttc ccgtttgttt   9180
taatttcaag cttataatcc cctttgcctt tagctgaatc accagacata atttgcttat   9240
tgctaaattg tttactactg tctgtaaaat aaacataact gccatgttga acatgtagt    9300 tcacaatatc agcagcgtcc ttttactga agtaactttt gatataatgg ccagagttaa    9360
tatctttctg actatcgcac caaggaatcc acataccacc ggtagatgaa tcatttcccg   9420
gagaaacaac cacatggtca ggtattatgg ggataactc atttgctgac tcctgattaa    9480
ataaatccgc tttatattca caaccaaaat tgttatcaac attaataata ttacgaacat   9540
ctgacataat aatttccccc gaatatagtt taaaggtttt tcaatttaa taacatatca    9600 aaggaactat aatactgtat atttacatcc gtcaacatta ttcacctaca gggtgacatt   9660
cctctattaa ataaaaata agttttgatt tttaactttt gataacttat gcaccaaatc    9720
agtgaccact gccgttaact tagttttgat cctcgtcact acggttaaac ttccgactcc   9780
cagaaagcaa aaaccccgc gagtgcgggg ctatattcaa agtgcttgag ttatttcact    9840
atgcggatag ttttgacatc aatttcaaca ctgttccagt cttgtccac ttccacttcg     9900 atacgaactt tgtcagttgg agtggccgtc agacccatcc agcgcttatc atcaatgtca   9960
acataaacag aaccactgtt atccctgaat tcatagagtt cgtgaccaac ctgtttaaca   10020
atgtttcctt ccagaacaac ccacgcatca tcacgaaaag atttttgcttg agcaacgctg  10080 gtcaggttgg gagttggacc tttaaatcca ccctgagtat agtctgtgct gtctggggaa   10140
acgaagccac cctgctgtgc caaagcacca aagaaaggg tactgagaat aagagtaatc    10200
agtgtttttt tcatagcttt ctctttgatt atgcgaagaa aaaccccgca tttgcgaggt   10260
tcgggtattc aataaattat gtgacattac tatcactctt gtcacgatat atcaactttt   10320
gtaattacgc aactttatta aggatttctt tttgcacaca tttatctgac tccaacgtag   10380 cccccctgaaa ccagcaagac atcctcaata aataatcttt catagataaa tattagttat  10440 tcattttttca aacagcacaa acacaattaa aaatatttaa acaattgttg agttgaattt  10500
tttcatgaaa gtttgttaaa atttaatttt taacatacgg tattcattat ttaaatccat   10560
gtattatagg gaagttcttt attttttatt gaaagaatag agcgataaat cagtatcaat   10620
ttaattaacc ataatattcc tatcagatta taataatctc cacctaaaaa ccattaatca   10680
ttaaattgac aataacttaa ggatttatat gataaaagtt aatgaactgt tagataagat   10740
aaatagaaaa aggtctggtg atactttatt attgacaaac atttcgttta tgtctttcag   10800
cgaatttcgt cataggacaa gtggaactct gacgtggcga gaaacagact ttttatatca   10860
```

```
acaggctcat caggaatcaa aacagaataa acttgaagaa ctgcgcattt tgtcccgtgc    10920
taatccacaa ctggctaata ccactaacct taatattaca ccgtcaaccc taaacaatag    10980
ttacaacagt tggttttatg gccgtgccca ccgttttgta aaaccgggat caattgcttc    11040
catattttca ccagcggctt atttaacaga attatatcgg gaagcgaaag attttcatcc    11100
tgacaattct caatatcacc tgaataaacg acgccccgac attgcttcac tggcactgac    11160
acagaataat atggatgaag aaatttccac attatcctta tctaatgaat tactgctgca    11220
taatattcag acgttagaga aaactgacta taacggtgta atgaaaatgt tgtccactta    11280
ccggcaaacc ggcatgacac cctatcatct gccgtatgag tcagcccgtc aggcaatttt    11340
attgcaagat aaaaacctca ccgcatttag ccgtaataca gacgtagcgg aattaatgga    11400
cccaacatcg ctactggcta ttaagactga tatatcgcct gaattgtatc aaatccttgt    11460
agaagaaatt acaccggaaa attcaacaga actgatgaag aaaaatttcg gtacagatga    11520
tgtactgatt tttaagagtt atgcttcttt ggctcgctac tacgatttgt cttatgatga    11580
actcagttta tttgtcaatc tctccttcgg taagaaaaat acaaatcaac agtataagaa    11640
tgagcaactg ataacattgg tcaatgacgg gaatgatacg gcaacggcaa gattgattaa    11700
gcgaacccgc aaagatttct acgattcaca tttaaactat gcagaactaa ttccaatcaa    11760
agaaaatgaa tacaaatata atttcagtgt aaaaaaaaca gaacctgacc acttggatt    11820
tcgtctccag aatggagata agaatatat ataccaagat aaaaatttcg tccccattgc    11880
taatacccat tacagtattc ccattaaatt gacgacagag caaatcacca acggtataac    11940
actccgctta tggcgagtta aaccaaatcc gtcggatgct atcaatgcca atgcatactt    12000
taaaatgatg gagttccccg gtgatatatt cctgttaaag ctgaataaag cgattcgttt    12060
gtataaagcc acaggcatat ctccagaaga tatctggcaa gtaatagaaa gtatttatga    12120
tgacttaacc attgacagca atgtgttggg taagctgttt tatgttcaat attatatgca    12180
gcactataat attagcgtca gcgatgcgct ggtattgtgt cattcagata tcagccaata    12240
ttccactaaa caacaaccca gtcattttac aatactgttc aatacaccgc tattaaatgg    12300
ccaagagttt tctgctgata ataccaaact ggatttaacc cccggtgaat caaaaaacca    12360
ttttttatttg ggaataatga aacgtgcttt cagagtgaat gatactgaac tgtatacatt    12420
atggaagctg gctaatggcg gaacaaatcc agaatttatg tgttccatcg agaacctgtc    12480
tctgctttat cgcgttcgtc tgctggcaga cattcatcat ctgacagtga atgaattatc    12540
catgttgttg tcggtttctc cctatgtgaa cacgaaaatt gcccttttt ctgatacagc    12600
attaacgcaa ttaatcagct ttctgttcca atgcacccag tggctgacaa cacagaaatg    12660
gtctgtcagt gatgtgtttc tgatgaccac ggataattac agcactgtcc ttacgccgga    12720
tattgaaaac cttatcacga cactaagtaa tggattatca acactttcac tcggtgatga    12780
cgaactgatc cgtgcagctg ccccgctgat tgctgccagc attcaaatgg attcagccaa    12840
gacagcagaa actattttgc tgtggattaa tcagataaaa ccacaaggac tgacattcga    12900
tgatttcatg attattgcgg ctaaccgtga tcgctcagaa aatgaaacca gcaacatggt    12960
ggcttttttgt caggtactgg ggcaactttc tctgattgtg cgcaatattg gactcagcga    13020
aaacgaactg accctgttgg tgacaaaacc ggagaaattc caatcagaaa ccacagcact    13080
gcaacatgat ctccccactt tgcaagcgct gacccgcttc catgctgtga tcatgcgttg    13140
tggaagctac gcgacagaaa tcttaacagc attggaacta ggagcgctga ctgccgaaca    13200
attggcggtg gcgttaaaat ttgatgctca ggttgtgaca caagcattgc aacagaccgg    13260
```

```
tttgggagtg aataccttta ccaactggag aactatagat gtcactctgc aatggctgga    13320
tgtcgctgct acattgggta ttaccccgga tggtgttgct gcactcataa aattaaaata    13380
tatcggtgaa ccagaaaccc cgatgccaac atttgatgat tggcaagccg ccagtacttt    13440
gttgcaggcg ggactgaaca gtcaacaatc cgaccagctt caggcatggc tggatgaagc    13500
cacgacgaca gcggccagtg cttactacat caaaaatagt gcacctcaac agattaagag    13560
ccgggatgag ttgtacagct atctgctgat tgataaccaa gtttctgccc aagtgaaaac    13620
cacccgtgtg gcagaagcca ttgccagcat tcagttatat gtcaaccggg cgttgaataa    13680
tgttgaagga aaagtatcaa agccagtgaa aacccgtcag ttcttctgcg actgggaaac    13740
ctacaatcga cggtatagca cctgggccgg cgtatctgaa ctggcctatt atccggaaaa    13800
ctatatcgac cccacgattc gtattggtca gacaggtatg atgaacaacc tgttacagca    13860
actttcccaa agtcagttaa atatcgatac cgttgaagat agctttaaaa attatctgac    13920
cgcatttgaa gatgtcgcta acttgcaggt gattagcgga tatcatgaca gtatcaatgt    13980
caatgaggga ctcacttatt taattggtta tagccagaca gaacccagaa tatattattg    14040
gcgcaatgtc gatcaccaaa agtgccagca cggtcaattt gctgccaatg cctggggaga    14100
atggaaaaaa attgaaatac ccatcaatgt atggcaggaa aatatcagac ctgttattta    14160
caagtctcgt ttgtatttac tgtggctgga acaaaaagag ctgaaaaatg aaagtgaaga    14220
tgcaagata gatatcactg attatatatt aaaactgtca catattcgtt atgatggcag    14280
ctggagctca ccgtttaatt ttaatgtgac tgataaaata gaaaacctga tcaataaaaa    14340
agccagcatt ggtatgtatt gttcttctga ttatgaaaaa gacgtcatta ttgtttattt    14400
ccatgagaaa aaagacaatt attcttttaa tagtcttcct gcaagagaag ggatgaccat    14460
taaccctgat atgacattat ccattctcac agaaaatgat ttagacgcca ttgttaagag    14520
cacattatca gaacttgata ccaggacaga atacaaagtc aacaatcaat tgctacaga    14580
ttatttggcc gaatataagg aatctataac cacaaaaaat aaattagcca gttttaccgg    14640
aaatatttt gatctctcgt atatatcacc aggaaatggt catattaatt taacgttcaa    14700
tccttcaatg gaaattaatt tttcaaaagg caatatatat aatgatgagg ttaaatacct    14760
gttatcgatg gtagaagatg aaacggttat tttatttgat tatgatagac atgatgaaat    14820
gcttggaaaa gaagaagaag ttttttcatta tggaactttg gattttatta tttccatcga    14880
tcttaaaaat gccgaatatt ttagagtgtt aatgcatcta agaaccaagg aaaaaattcc    14940
tagaaaatca gaaattggag ttggtataaa ttatgattat gaatcaaatg atgctgaatt    15000
caaacttgat actaacatag tattagattg gaaagataac acaggagtat ggcatactat    15060
atgtgaatca tttactaatg atgtttcaat cattaataac atgggaaata ttgcggcact    15120
gttccttcgc gaggatccat gtgtgtattt atgttcaata gccacagata taaaaattgc    15180
ttcatctatg atcgaacaga tccaagataa aaacattagt ttttttattaa aaaatggctc    15240
tgatattcta gtggagttaa atgctgaaga ccatgtggca tctaaacctt cacacgaatc    15300
tgaccctatg gtatatgatt ttaatcaagt aaaagttgat attgaaggct atgatattcc    15360
tctggtgagc gagtttatta ttaagcaacc cgacggcggt tataacgata ttgttattga    15420
atcgccaatt catataaaac taaatccaa agatacaagt aacgttatat cactgcataa    15480
aatgccatca ggcacacaat atatgcagat tggcccttac agaacccggt taaatacttt    15540
attttccaga aaattagctg aaagagccaa tattggtatt gataatgttt taagtatgga    15600
```

```
aacgcaaaat ttaccagagc cgcaattagg tgaagggttt tatgcgacat ttaagttgcc    15660
cccctacaat aaagaggagc atggtgatga acgttggttt aagatccata ttgggaatat    15720
tgatggcaat tctgccagac aaccttatta cgaaggaatg ttatctgata ttgaaaccac    15780
agtaacgctc tttgttccct atgctaaagg atattacata cgtgaaggtg tcagattagg    15840
ggttgggtac aaaaaaatta tctatgacaa atcctgggaa tctgctttct tttattttga    15900
tgagacgaaa atcaattta tattcattaa tgatgccgat catgattcgg gaatgacaca    15960 acagggata gtaaaaaata tcaaaaaata taaaggtttt attcatgtcg ttgtcatgaa    16020
aaataacact gaacccatgg atttcaacgg cgccaatgca atctatttct gggaattgtt    16080
ctattacacg cccatgatgg tattccagcg cttattgcaa gagcagaatt ttaccgaatc    16140
gacacgctgg ctgcgctata tctggaaccc ggccggatat tcggttcagg gtgaaatgca    16200
ggattattac tggaacgtcc gcccattgga ggaagatacg tcctggaatg ccaatccgct    16260
ggattcggtc gatcctgacg ccgttgccca gcatgatccg atgcactata aagtggctac    16320
ctttatgaaa atgctggatt tgttgattac ccgcggagat agcgcctatc gccagcttga    16380
acgtgatacc ttaaacgaag ctaaaatgtg gtatgtacag gcgctcactt tattgggtga    16440
tgagccttat ttttcattgg ataacgattg gtcagagcca cggctggaag aagctgccag    16500
ccaaacaatg cggcatcatt atcaacataa aatgctgcaa ctgcgtcagc gcgctgcatt    16560
acccacgaaa cgtacggcaa attcgttaac cgcattgttc ctccctcaaa ttaataaaaa    16620
actgcaaggt tactggcaga cattgacgca acgcctctat aacttacgcc ataacctgac    16680
aatcgacggt cagccactgt cattatctct ctatgccacg cccgcagatc cgtccatgtt    16740
actcagtgct gccatcactg cttcacaagg cggcggcgat ttacctcatg cagtgatgcc    16800
gatgtaccgt tttccggtga ttctggaaaa tgccaagtgg ggggtaagcc agttgataca    16860
atttggcaat accctgctca gcattactga acggcaggat gcagaagcct tggctgaaat    16920
actgcaaact caaggcagtg agttagccct gcaaagtatt aaaatgcagg ataaggtcat    16980
ggctgaaatt gatgctgata aattggcgct tcaagaaagc cgtcatggtg cacagtctcg    17040
ttttgacagt ttcaatacgc tgtacgacga agatgttaac gctggtgaaa aacaagcgat    17100
ggatctttac ctctcttcat cggtcttgag caccagcggc acagccctgc atatggccgc    17160
cgccgcggca gatctcgtcc ccaatattta cggttttgct gtgggaggtt cccgttttgg    17220
ggcgcttttc aatgccagtg cgattggtat cgaaatttct gcgtcagcaa cacgtattgc    17280
cgcagacaaa atcagccaat cagaaatata ccgtcgccgt cggcaagagt gggaaattca    17340
gcgcaataat gcggaagctg agataaaaca aattgatgct caattagcga cgctggctgt    17400
acgtcgtgaa gcggcagtat tacaaaaaaa ctatctggaa actcagcagg cacaaactca    17460
ggcgcagtta gcctttctgc aaagtaaatt cagtaatgca gcgctataca actggctccg    17520
tggaaggttg tccgctattt attatcagtt ttatgatttg gcggtctcac tctgtttaat    17580
ggcagagcaa acttatcagt atgaattgaa taatgcggca gcacacttta ttaaaccagg    17640
tgcctggcat gggacttatg cgggtttatt agcgggtgaa accctgatgc tgaatttagc    17700
acagatggaa aaaagctatt tggaaaaaga tgaacgggca ctggaggtca ccagaaccgt    17760
ttctctggct gaagtgtatg ctggtctgac agaaaatagt ttcattttaa aagataaagt    17820
gactgagtta gtcaatgcag gtgaaggcag tgcaggcaca acgcttaacg gtttgaacgt    17880
cgaagggaca caactgcaag ccagcctcaa attatcggat ctgaatattg ctaccgatta    17940
tcctgacggt ttaggtaata cacgccgtat caaacaaatc agtgtgacat tacctgccct    18000
```

```
tttagggcct tatcaggatg ttcgggcaat actaagttat ggcggcagca caatgatgcc    18060
acgtggctgc aaagcgattg cgatctcaca tggcatgaat gacagtggtc aattccagat    18120
ggatttcaat gatgccaagt acctgccatt tgaagggctt cctgtggccg atacaggcac    18180
attaaccctc agttttcccg gtatcagtgg taaacagaaa agcttattgc tcagcctgag    18240
cgatatcatt ctgcatatcc gttacaccat tcgttcttga tccaaaaatt aactggacag    18300
agaccctgta cgggtctctg tccacacatc cgaaaaccc accttgtcat ccatgacaaa    18360
gtgggaatga acatgattgt tatgcttcgg attcattatg acgtgcagag gcgttaaaga    18420
agaagttatt aaaagcccgc ttaaagccgc tccaggtaac ccggctagcg gcattggcaa    18480
cttcccctcc aacggcatga tgagcggccg cggctgtccc gccaatggct gcaccaaccc    18540
attcaccggg tgtacggcta aggtaataa atacttcaga aatatttctc ccgacacttt    18600
ctcctatcat tcggccaaac cagctcctgg aactgacagc gtgggaaatg gcagagctaa    18660
tgcctcttct gagcagtaac ctgccgataa accgataagg gccatcccat agattaccaa    18720
tgatccttcc ccatcgagca ccatacatag caccaatcgc tgcccgttca cccagctcag    18780
aacttccctg atggcggcca agtaatatgc cgccaataat tgcgcctgat agtgcccta    18840 accgctctgg cgcgctgaca ttaccgggcc tgagcgtatc cagcgtacct tgtccggcgg    18900
gtgtggcaat actgatagcc atgcccgtgt tatgctctcc ggctaaagcc attaatcctc    18960
caacggtgac cgctgttgct gcggaaatgg cggtacctgt cgaagagctg ttaaatagtg    19020
cagacgtcac aagcgatgtg acaacaaaag cgccaacctg aacaggaaca gaacgtttac    19080
gcgtcagata acttaaaact tccccaattt tttctgagat gttgttcgcg aaaaacccca    19140
tcaccgcccc ggagacaaaa ccaccaatgg cagccccgac aatcccccaa ggcgacgctc    19200
ctgcaatcgt ggccgccttc accccagac ttgctacccc cacacccaaa acaaacgttc    19260
gcaatcctcg gtttaatttc aagaacgtat caaaggaagc gccttgttca agcaggtgtt    19320
ctgtcgtgat gttgactgcc tttcgatacg cttttttccc tatccaggca aggacaccct    19380
gaccggggaa acgaccatca gaatcagaaa aaacgatggg gttattcctg cacattcgga    19440
acaaattgag accatcgacc tcaccggcag gatctacact caaccatcgc cctgtccacg    19500
attgataata acgataaccg tagtaataca accctgttgc atcccgctct ttgccagaat    19560
aacgcacggt tttgtaatca gcttctgact gacttcgggc tgcccacacg gcggttcccc    19620 catagggta atattcttcc tgactaatga tctgcccgtc actgtccaat tccagcccgc    19680
tactgccaat caggttgcca taactgtagc gcagctgatc attgctgata tccgccggtt    19740
tgcctgtttc ccaatgcagc acccgcactt gtgcctgacc cgattcaccg acagtgatga    19800
cctgcaaaaa ctctttaat gtattgccgc tatatgtcgt gcgccattcc agctctggca    19860
aatataatgt tcgctgtatt tgctcactgt tacctgtctt ctgaatatga gtcttaatga    19920
cacgctgact gtctgcatca taacggtaga attcctgatc aggcgtcgta ttttccctat    19980
tgaccaatat cacttgttgc aattcgtcac ggggtgtcca gaaaagatcc tgaccgggaa    20040
caagccgggt ctgatgcccg ccggggtga acaacatatc cacctgagtg ggatcttgcg    20100
ccagctcttc cagtacagcc cggttgctgt gatctgaaac ggtcatgttc gttgtatagt    20160
tattaccggt gatcggtgaa ttatggcgaa ttctggtcag atttcccca cgatcatagt    20220 cgtaagtgcg agagtaattc gtataagtat tgttatcaat cagagcgggg atgggtaact    20280 ggttttttg tcggccaata ttcgccattt cacgcccagt gacggaaacc agctggtaca    20340
```

```
ggctgtcata ggtgtaagta ttttccggta caattttctg gttgcgccaa aagcgggtaa    20400
tttcagcatc attagttgat ttcagcacat ttccgacagg atcatattca taacgcaggt    20460
tttgtaaaat tttctcccca gcggcatgac cggaaggacg ttctgttttt atgccaataa    20520
ctcgttgcgt ctcgggttca taggtatatg tagtcactat cccgttacca tgttcctccc    20580
gtagcttctg gctggcagcc gaataggtca gggatttcac gataacttgt tcttgttttc    20640
ccttcagcgc caaccaactg ccttgaagca gaccggccac atcataggcg atacgttgct    20700
tgtttccggc agcatctgta ctcgttaata ccgtgccggt agcatccgtt gtgctgacag    20760
aagtgaagct ttccggcgcc agcgcgtttt tccagccaga ttcatccata ccgtgccaat    20820
cggcttcgct gtcatctttc agtaattgct gtgtgatgga caagggtatg ctggttaacg    20880
atatgctgtt ggtttgattc attccggtgg gatcataatg gaccacgcac tggccggcca    20940
gattattgcc ttttctgcc ggcgtatttc ctgaccagat caatcgctcc gtgatacagg    21000
cgttctctcc ttttacctgc tcggtaatcg ttagcaatcg tcccggaagg ttatcacttt    21060
catactgaaa cgttcggcta acgccattgg cgctgacagc taaaacggga cgcccggcaa    21120
catcatgcag ggcgacacgg gttccggcat ccacactttg cgtacgcaat gccttcttac    21180
tgagtgatga caagagaata agattgggtg taatggcgtt cttgtcactc gctgtctgct    21240
ggcgttcata aaatcgcgga tcaatactct gagtcagaga tccttgagca tcatattgat    21300
aaccggtgat gcgttcatcg gttacctgag gtgtatcggg gtgccgatac caggctattt    21360
cgcgtactgt ctgaccacgg ttgtccagta cggtgacgaa tggcgtattg ctgtgaacga    21420
aattcttcat gattcattcc taaatggagt gatgtctgtt cagtgaacag gcatcactga    21480
gctttatgct gtcatttcac cggcagtgtc attttcatct tcattcacca caaaccaggg    21540
agtgaataag gatcgacgaa acccgccttt ggccgtgata acctgatatt cacgccccaa    21600
cggatcatag taatgggtat cggcatatat atcctgccgg gcactgtcat cactgacgta    21660
ctgccaacta ttcaggaaat acggttgata cttacgcagg gcttggcctt tccgtcata    21720 ttctgtacgt ccggaaactg cccaacggaa atctgtcatc gccgtttcag gcgcgccatg    21780
attttcagcc acaatggctc catactcatc acgtacccag gcttcaccac tttcatggcg    21840
tacggctgtt tgtaaggttc gcccaaaacc atcactaaac gtaaacgttt gacgtaattg    21900
ttgttccgga tcggcatcat agcggtcggt gatcacactc agtacatggg gtgggttctg    21960
tgaattgact tgctttggca tggcagcggc agggttattt tgttgccagc ggcgaaaagc    22020
aagcgacagg agataaccat cttcagtgat gatcccagcc ggtttcagct ctccataaag    22080
ctccccatca ttagaaaagc tggcctgaac catccagctc agagggcat aaaccatcag    22140 ccctgcaaca ggtataccgg gtttcaatgc cagagcatca tccaccgttg tggggacaat    22200 aaagggggaca gtttcatttt ccgcaggggt atatccttgt ttttcaccgt tttcagtccc    22260
ccagaaacgg aagctggtta ccctccccag tgcatcaaac gtcacggtgt gatagttatc    22320
attgacatct gtggtgttat ccgcaaccat aaatcgataa tcgtaatgcg cttgcatacg    22380
caggccagcc gcatcctctg ttgcggtgat aacacagtaa tggctatccc acgtgactgt    22440
cgttttacct gtaagcttgg tttcccgttg caccaatggc cgatagaatc cgtctgcacc    22500
ggcatattct gtaaattcct tttgtcccac ccagacatgg aaatctgtct tttcactgaa    22560
cggcactttt gccgtattcc agcccgcatc attcagctgt tttgtcagct cctgctcatc    22620
catcacctcc tcaaaagccg ccaacgatcg ttcatcaaac tctgcggttt caatgtatgc    22680
caccagcgga ggaatagcgg gttgttcttc tggaccggta tatgctacac gctgatgtcc    22740
```

```
cagataatcg gctgcggcat caggcaacaa caatgctcct gcacctgtgg cagaaaacca    22800
ttcaagggaa aatccaccgt ccggcacttt atcggcttga taaatacgtg cgtcactgcg    22860
tgaggtatcc ataagccctg tgatccacgt attatcatca tgattcagat gatgataaga    22920
agaacgctgg cgtgtcagac gaaggaacat ctgctgttcg tcgaaactgc tggtgaaaag    22980
tgtttcgggc agggtatccg gataaggcga gaactcaggc tgtggacgtc tcgaataggc    23040
aatctcaaga ttgtcctgcg gaaatcctaa cgcatcagat ttaaggacga tcttttggct    23100
gcactgtgga tcggtagcaa cccgttcata tcggtattgg cgggattcgg ccaccgaaac    23160
cagtaccgca ggcacgtccg ataccatcac cggtaacaaa cgtacttggg tgcgggattc    23220
atccactgaa taaggcgtac cggccagtat agaatcatca tccccataca gctcactgcg    23280
taaacgttgt ccttttaagg ctcgatgtaa ccagtattct tcctgttcgc tcggcgtgac    23340
cgtcatatca ccaccggatt tttcgtcata acgggtaaag cgtggggtaa aatgggggaaa   23400 tgcctgttga tcccctgcc aatattccgt gggcagaaga atatcgactt cccgtacgcc     23460
agtgccgtac caattaaccg tgcgcgaagg tgccggtggt tcagcatgtg tcccctgtgt    23520
cgcactcgcc cgtgaatcaa tatcagtttg tgtcacccgc ccaaaaccac gaaactcccg    23580
ttccagacca tcccaggcac catgtgagta atgataatgg ctggtcaatc ggttaccgga    23640
aatttcatcc agcacttccg tgcgccacaa cacatgcacc gggaacggta agtagctgac    23700
caccgtcatc ccggattcag aagcctgtaa tttctcatcc agccagaact gggcagagct    23760
gcgataatac agcgtggttt ctgttcccat attgttattg acggcattca gcagccaagg    23820
cttgaatatg gtcatatcca atcgccagtg ctgcaccttc atatggggga tcgtcaaaat    23880
aatgctggca gtccctaatc cttgtgtatc cgctatttgt aaccgacaag tatcatcaaa    23940 acgtaccca tccggcagat caatacgctg aggttcagca aaatgattgc cgctttcatt     24000
ggcatagagt tcaaggtaag tattgcgggc ataaataaaa tcggtggtgc ctgagccatc    24060
tatgtctacc atatacagtc tgtcggggtt aaacgtttcc ccgctaatct ggaagcctgt    24120
catcatcaga ggctcaccaa attttccatg ccccaggttc ggccagtagc gcacgctatc    24180
tgccgttact tccaccagat gtgattgccc ggagcctgtc atatcactga atgcgacaag    24240
atgacgctca tttctgccgg gaaccggcag tggcatatct gacaaatgaa tcacatcctg    24300
agcgcgatcc catcctgccc gattatttga ccagacacgt acactatttg gcccgataag    24360
cgctaagtca ggcagcccag ccccatcaat atcagccagt tttgcctgcg gatggaaata    24420
ttccattggc acagcggata atggaataaa gggtgtccat tcaccttccg gtgacatggt    24480
gtggtagccc cgtaaccctg atgccgtaat cacccaatcc agacgcccgt caccattgat    24540
gtccaacaac atcgcgcttt cctgttgtgc cggaatatgt ggcagtggtt tggcctcctc    24600
ataggtaacc gcattcgttc cttcggcagt gatatcccgt accggagcac ggtaccacca    24660
ggctttctga gtatcctgat aaagtacgcc ggaaattcct tctccatata aatcaaccaa    24720
ttggtatggc tgcaacgtgt tcattttttc taactgcggc atggactgcc agttcagatt    24780
cacgccatga ttaacacgtt gataatccat ttccagcggg gacatcatca ctggcgtacc    24840
gtccgtttca tgggccagtc tgcgggccgt ttgcagcaag gaaaccttgt tgttcaggtc    24900
ataatccaga ataagacggg aaaccagcgc cggtgtttct tctgcaacct tttcccctgc    24960
cagcgctttc agctgatgaa acatcagaac ttggcgacac aagcgacggg ttcgaattc     25020 aaacccatat tcatagcggg agaaactgtc cggacgacaa cgccattttt caggcacatt    25080
```

```
gttttcagac acattgtttt ctgacacatt gaattcgggt acagagttca gcgaagatga  25140
gcgctcaccg taatcaaata ccagatgaaa cagccagtca ttatcagcag gaatacctga  25200
ttttaccgcg aaaaagcgg tttccggctg agtattgcca tagctgactt ttgccagata  25260
acgctgggcc gtaacacctg aatgctgagc aagttcatgc tcatcacagt caagatcgtc  25320
ttctgcccga tagtgatagt aaatatgttc cccggtatgc gtgacggttt cctccatcag  25380
ccagcgggca attctggttt catcctgcgg gtcagcaata cgtgcatggt gatgcttacc  25440
gaataggtgc actaaaccat ccgcagtaaa aagtacccaa aaagacgtct cttcctcacg  25500
tctctgctgt ggctgccagt gttctaaacg aacgattttt tctgccacgc gggactgata  25560
gcgggtaaca gtatgcggct gtgtcagaac cgtccccaac agtgaggttg cggtgcgttg  25620
ctctggttgc ccttggctgt ccggcacaat actcaacact tccccatccg gcccgagata  25680
ctcatcttgt cccgtatagt gcggaacgcc cttggcggta cgcaggctga taaaaccaac  25740
cccacattgc caccccatcc cgaatgaccc attgccggca gtactgctgt aattcagtga  25800
tagcaccggc accagaccac gcccgacaga gatcggcaag ggcagtgaaa atgacgctcc  25860
cccttccgct ccgacggcat tgagtgcttc tcccattcct tttagtgatc cgccccaga  25920 gggcaatgac ggtatttcaa gtttcaaagg tgttgaaccc tgcataaaaa ctccttaaac  25980
aggctccctc aggagcctgc ctatcacaat gttttaatta agaacgaatg gtatagcgga  26040
tatgcagaat gatatcgctc aggctctcca gcagcgcttt ctgccgatca gtcgcatccg  26100
ggaaactcaa cgtcaggctg ccgctgtcat tcacggaaat accttcaaac ggcagataac  26160
gggaatcgtt gaaatccagc ataaattgac cactgtcatt cacgccgtgg gagagagcaa  26220
tagcactgca accgcgtggc atgacgatgc tgccccgta attcagcacc gcccgaatat  26280
cttcatacgg cccaaccagc gccggcaagg tgacactcac ctgtttcaac tgacgggtat  26340
tgccaaggct ttcggggtag tcgctgaaaa ttttcaaatc agacaatcgc actgaggctt  26400
ctatctgacg gttactgagt tttaattcat tgccggaagc tcctacgttg cctttccctt  26460
cacgcaggaa ttgcgtgagt ttttcggtca gattaaagtt gtctgatgat aaggcctgat  26520
agaactgtgc caacgagacg gtacgggtca cttccagtgc ccgctcatca cgctccagcc  26580 agacttttc catttctgcc agattcagca gcaacgtttc acccgccatc aaacccgcag  26640
tcgtaccgtt ccaggcccca ccccggataa aggtaacacc gttgtcggtc agctcgcggc  26700
gcagcgcttc ctgtgccatc aggcagaagg actgggtcag gtcaaagaac tggtaataga  26760
tagcactcag cttccgcgc atccaactgt aaagcgcttt gtttgtgaat ttacgctgta  26820
acagctctaa ctgagcctga gtatgggcct gctggtctc ctgatattcc acctgcatct  26880
gtgctgcttc gcggcggatt ttcaggcttt ccaactgggc atccatttgt ttgacttcac  26940
cgtcagcatt atcacgctga atttcccact cctgacggcg gcggcggtag gcttccgaac  27000
ggctgatttt gtctgcggaa tattgggaag ctgtggcaga aagcgacatc acggaggcgg  27060
aagcacgcag tgctgccccc caacgactgc cgccacaagc taaaccgaac acgtttggca  27120
ctaaatcggc caccccttcc gctattgaaa gcacctgccc ggccagagac tgacctgccg  27180
ctgcatcaag cagtgacatt gccgctgtt ctccgtggtt gatatcctcg tcatacagct  27240
gctggtattt ttccagacga ttttgtgcac tgcggcggct ctctgccaat acagcaatat  27300
cagcatccac ttcatcgaca gttcgttgct gaatacggat gctctgtgtc gccagttcca  27360
taccctgctg tagtagcagc gtggtgagtt catcggcatc atcatgctct gccatactga  27420
gcagagaggt gccgaactgg gttaattgcg ctaccagatt gcgggtccgc tccagcatca  27480
```

```
ccgggaagcg gtataacgac aatgtgccgg gcagcactgc actaccgccc tgagaggcct   27540
gtaccatact ggtgagcagc gctttcggat cggtaggctc ggcgtaaatc gccagcgata   27600
acggctgtcc gtcaatggaa agattatggc gcaggttaaa caggcgcaaa cgcagggttt   27660
gccagtaatc ggtgagcgcc gggttatatt ccggcaggaa caaacccacc aacgagttag   27720
cggtacggag attcttggaa accccaccac ggcccagcat cgtaagatcc tgctgataag   27780
ccgcctgcac ggtttgactc gccgccccgg aaagggacgg tgctgcccac tgttggctac   27840
cgtaatcctc cggctcatca ccgagcaatt ctaaagtacg cacataccac attttggctt   27900
cattcaacgc atcgcgggtc agttctcgat aggccatatc gccgcgcaga ataagttgat   27960
ccaacaggcg cataaaggtg gcaatcttgt agtgcattgg gtcatttttgg gcgacggcat   28020 ccggatcgat ggcatccagc ggattggcat tccaggaggt ggtctcttcc agcggccggc   28080
agttccagat ccaggggggcg atttctccgt taacgatata gccggcggga ttgtagacgt   28140
agtttatcca ttgtgtggct cgtcgaatt gttttttcctg tagcaaacgc tggaagcaca   28200
tcatcggggt gtaatagaac aattcccagt aatagagggc gctggcacta ttgaaatcca   28260
tcggggcgga atagcccgtt gcgatagaaa cattcaaaaa tcctttgtat ttcttgatat   28320
ttttcacgat cccctgttgc gtcattcctg aatcatgatc agcatcgtta attaatacaa   28380
attgctgttt tgtctcatca aaataaaaga aagcagattc ccaagtgttg tcataggtaa   28440
ttttctggta tccaaccccc aatctgacac cttcatgcat gtaataccct tcggcataag   28500
ggacaaacag tgtcatactg gtttccgacg tatcggataa cattccgctg taataaggct   28560
gccttcccgt gttaccgcca acattcccaa tatggatttt aaaccaccgc tcatcgccat   28620
gttcagcagg gtcatatttta ggcagaacaa agttggcaaa gaagccttct cccaacggag   28680
gttccggtaa ccgctgggtt tccattgtca ggatagtatc aatgcccgtg tttgctctgg   28740
ataccagttg agaagccagc agggtattaa gacgaatacg atacaccccg agctgcatat   28800
attgggcacc cgaatgagtt tcacgcagaa acagaatatc ttccggatta taatttaccc   28860
gtttcaccga taatgtttgc ttgatcttac ccagcactcg cccgtctttg ctttggtct   28920 caaaaacgat atccagagga gcaatattat tggtaaaggc caacgatgaa gcatcgatttt   28980 ccagtggctt aaaggtgtac ggcatagcat caaaactgtt tgccggcaag gaagcaatat   29040
ggtcactggc cgtaaaggtg tgggttttac tgccagccat caccgtaatt ttgatatcgg   29100
tattgttaat gcctgtatca atatccagcc agccggatga ttgataggaa ctaaatatct   29160
ggaagccctg agaattatta ccatcaacag cataactgca ctttttaaaa tcactggttt   29220
tattgctacc aaccgtgaaa acggtgttta aaattgtgtt tggagaaaat ggaaactcga   29280
acaatctggc ataataatta ttttcaactg gtgttagaat caaacgccta gtgtaatctg   29340
cgttcatcaa gtggcttga actgatgcaa tatagttttt cgtttttatta taaacggtga   29400 tcggcccccc cagatcagag taaccgccat aatgtttaac ggtatttgcg atgataaatg   29460
cattgccgta ctgggacttt ccatccaccc ccgtcagttt catggcgctg atttgttttgt   29520 ttctgatgac attgccactg ccatcatatc tgacagtgaa agcggcgtta tgtagcgtaa   29580
tagcaaggtt atcgctggag tatttactgg ttatctgcgg aatattcccg ttctccatca   29640
ccgtcagact atcatcaccg atggcagaac ccatattcaa cgaggcaggc acttcaaaat   29700
cctgcgcgaa acgatagctg gccttttctta ccaagtcgtt gccttgagta tgaatgatat   29760
caaaggtatt tttcagttgg ctgtaacggc tgagtgctgt gttctccatc ttttttgaagg   29820
```

```
agccatcgcc gtaaatggtc atgcctgcca cattttatt gctgccgcca aaatccgagt    29880
aactcttccc ggttttgtag acaaacacca gcagagtgtc ctcgccctga aagcctgatg    29940
cggccagcgc cagccgttca gtgtcaggtt ttttgtcagt gaccgcctcc acctgcgttg    30000
tgatatcgta agaccagggg gcactccaac tgccatcatg acgcagaaac gccagtttca    30060
gagtaaaacg gtcataggtt tccaccggat cagtaccatt tttcgccact tcctcttttt    30120
ctacccagat aaggtgcaaa cgttccctga atatgaccgg acgtattgca tccttgtagg    30180
ggttgaccgc tgtatcaatc ttcgtccact ctttccaggc attggcggcc agttcacccg    30240
cctgcatccg tgatatatcc acgttacgcc agtagtattc cggcaggttc tcccgcgttt    30300
ggccgacaaa ccaggtcagt ccggtgttgc tgttgacgtt gtcgtgatag gcgctgacaa    30360 cttttcagatc cgccacggtt tcaaagcggg tcaggtaagt tttaaaggca tcctccactg    30420
tgtcccggct aagtttactc tggctgatat tttccagcag ttcatccatc atccgggtct    30480
gcccgatacg ctgggttggg tcaatgtaat tttccggata taaaccagc cgcgacaccc    30540 cgccccaggt gctgtaacgg ttattcaccg tccagtcggt aaaaaactgg cgggttgaca    30600
catcggcacg ggcattaggc tctatccgat tcagcgcccg gttgatgtag agctgaatac    30660
cggcaatggc ctctgccagt cgggtggttt ttatggcaga agagacctga ttatcaatca    30720
ggaaatagct gtacaggtca tcccggctgt gcagggacac cccttctggc tggatattcg    30780
ccagaaacca attgcacagc acgctactca ggcgctccgc ggtataatcc gccagcgtct    30840
gagcctgttg tgtactgagt ccggcttcca tattttctgc cagtgtctgc cactcatccc    30900
aggaaggcag attcgactcg gctttgttta atgcagtcac gtaacggata ttcaccagcg    30960
tacggataac cgacggcatc gtgtgcagtg ctgatgccac atctatccac tgcaacacgg    31020
tgttgatatc ctgccaacac tgaagctggt tcacgccggc ggaaaccatg gcctgcgtta    31080
ccatactgat gtccagcccc atcacggagg ccagtctgtc ggccgtgagt gtctgctggc    31140
gcagcatatc cagcgtgtca gagccgggat tgcccagccc attaatccac tggtggaatc    31200
ggtagagtga aatagcgta tcaatattgt gctgtccggc aggttgattt tttgcccca    31260 gcacggcgaa tccggagatg accagcacgg atagctccgc ttcactgagg cgcagtgtct    31320
gtacggaaag cgataactgt gccatcacat ggcagaattg taccaattgg gtggtttcat    31380
tggcatttaa cgactctttc aataccagtg tcataaaccc ggcaatatct aagccacccg    31440
gccgcaggtt atcggtccac aacaggatat accgtgccat atccggtgac gccagatgca    31500
gcgttgcagc aataaacggc gcgagaattt cagcctgcag ctcccgattg tgactctgtg    31560
ccatatcttc actaatactc ggtcggaggt tattgagcag attactgatt ccggtgaaa    31620 tattcccgct aaactctggc gtacataata accagatcgc ttcagtggtg atttccgcct    31680
cagtcagcca ctgcgtcacc tgatacagcc agataaccag ccgtggcaac tccccggaag    31740
acaaagaagc cgttgttttg ccattgaacg gcgaaagacc ataaagcata cacagttcat    31800
tgaccgtcag ctgatggaca cgggccagta acgtgaggcg atacagtgaa gagataacga    31860
agacagaaag tgtgatggta ttttgggcgt ccagcacacc cgccagtttg cctaactgat    31920
acagttcacc actgttgacc cccagaccac gcatcagggc tgaacgggca aaggtagatt    31980
gctcttcatc cggatcaatg ctgaccgtgt tgccgtcggc ttcaaagatt ttccctttca    32040
gcggcggtgt attaaagaga cggttaaaat gactgacact gtcatcgtcg gcatattgat    32100
taatgaccga tccgttcagt acctgtgcat catcaaagct cagtgcataa cggtgactgt    32160
agaacagagt atagaaaact ttggtcagaa cggagtcgtt gatgatgcct tgtgcattgt    32220
```

```
cactgcgtac gatagtttgc agttcattcg gtgaaagccc gctagtcagg cacaagcgaa    32280
tggctttatt cagtttgagc gcaaatatag tcaggggata agactcaaaa gtgaatattc    32340
cgccgccctg atttgtggcg ctggtggaag acgtatagcg ataggcgtat atctttacac    32400 cgttttttgta ttcagaatca gatatgttac ttagataatt acttttaaaa ttcgtattgg   32460
ctattagagg accggaaagg ctgccgacaa tgccacttgg ccctgcgttt tttctaagag    32520
tagccccaaa ttctcttgat accttaaaat tagcacgtat aaagaactga ttatttcctt    32580
catacatcaa atcaaagtaa tttatatttt tatcataatc atctgttttt acacgtgtta    32640
ttttgtaagc ttcgagttta ctttcattat tgaccactaa acccgttgag atattatcca    32700
cataagcaga ggtgctgtca gaatagccat tctgcaacat cccgaggtat ttttgcacct    32760
cagaaagttc aagaccataa tacttggcta tccatgattg tgacgcgaaa ttttcgggcg    32820
tgatattttc actgaagttt tgcgcaaata aagcatcagc gttcttttcc gtaatctctt    32880
cggtcaaaat gttataaagc tccggagaaa tattggccag aatcgccagt aatgaagccc    32940
cttccgcctg ccccatcacc tcaggattac gggacagcgc tgacagtgta ctgtcatggg    33000
tcataatgac ctgacggata gtctcgtaag gctgatggta aggggtatca atggcctgac    33060
ggtaagttga caggctctcc atcaatgcgt ccgaatcacc tccggtcttg cgggtaatat    33120
gctccagcaa cagttcgtta gacagtgtca gggtggaaat ttctgtatcc atattactct    33180
ggctcagagt cagatcagcc agatccggac ggcgattatc aagatgataa gcagagcttg    33240
aaaaatgtaa gtccttcgct tcacgataca attcggtgag atagccagcc ggtgaaaaca    33300
tggaagccac tgaacccggt ttcacaaagg aagaagaacg ggcaccaaac atttcatcat    33360
aactgcgtga aacgctgtct cgttcaatac cgagtcggat agcaccggat aattgtgggt    33420
tggcacgggt aaaaatacgc gcttccagca agcgattatt ttttttctgc tctatagttt    33480
catgatagag atggcgagcc tctccccaac tgagctggtc atcaaagatt tttctcagtt    33540
cactgaagga taaatattgc agatccgcaa gagtcatcgt ctgaccgtcg cgagtgggac    33600
tgattttatt gagtaataca gccgtgctat acataataac ctcaattatt ttataaaata    33660
gtgttgtcag ttaagagttc atctgaagat ttagtgctta ttttgtaagt cattattcta    33720
ttcacattgt aattatttgt tttatctgag attaatgata ttaaagagga tgctattgta    33780
aatggcggaa tagaatacga ttttctactg aaatttcatt ttaatcataa aatttataac    33840
tgactttaat gttacagtcg taatcgatat tgtgtcatgt tggcatcctc ttcatctgcc    33900
ttaaaataaa gtagggtacc aaaaggaata catacttgaa tccaagattg agcacaaatc    33960
cacatattca gcttattaaa gataattaaa tttatttat cataaataaa taggataacg    34020
gccctggatt ctgaccaggc gaggccaaaa gtcgatgaag ctaagttacg gttgaacaaa    34080
tttgtttact ggtaaatgg gcacaaactc tttatataaa taaatagcat attgtaacga    34140
gtaattaaaa aatgaaaatc cagcttacct ggttattcat tcattaacaa acacaaaat    34200 atttatgcca acggcactta gaattaaata attttcttta tcaacttta cgttaacttc     34260 atttgataaa agtaagatcc catgattttt caagatcctt attcggttat aactgaccag    34320
attgggaaaa tcaaccttaa tgtctcatgt gaaataaaat attgtccaag tgatttattg    34380
ttttgtatta taattcagtc tcttttatca acatctaact taagtcctca agagaaatta    34440
attgcaaatc ggtcaccata accggctaat aatgtattga tctcatattc cattgtttcc    34500
tgagtccagg tgataaaacg tcgccagtgg tatttagcct ccctcagac gatttcaatc    34560
```

```
aaattcagtt ctgggctgta ggcgggaagg taaagtaaaa gcaggttgtg ctctcgtaac    34620
cagcgatttt taagtttttc atcgatccca tgatggatag gcgcattatc taacacgaca    34680
aatgtcaggc gatgctcgcc ttgttgggcg acctgctcta aaaaatcaat gacattactt    34740
cgcgtgacac tgcttgatat tatctgataa aacagcctgt tatcagtgta atttagcgca    34800
cctagcactg accgtctgac agagctttgc ggctctgctt catggggctt acctcgtgga    34860
ctccatccat attggaccgg tgggcaggcg gaaaaacccg cctcatcaag atagagcagc    34920
cgataatgac ctgcccgtgc gcccgcctta atttttattca gtaaggcggc ttttcagca    34980 aattccgttt tattgcgttt ttttaagcg acaggcgggg gcgttatag gggagtccct    35040 gttttttcag ggtattcgcc agcgtttcaa gcgtacaggg cagggaaccc tgcctggctt    35100
cgacgcacgt cagggactct gcgctggcgg cttcgagcgc agtggcaatc atgtcaggcg    35160
tcatggcgag ataccggcct ccggcatgac cccctaataa tcccgctatc cctgaatggt    35220
gccacatgtg aacccaatta tagataaccc ggagactgca tccgatttca gcggtgatct    35280
gggacggctt gatccctctg gcaagcatga gcaaacccgt tcctcgcgta cgaatgtccc    35340
ggtgtgggtg attcaaagcg agtggttgca atgtgattcg ttcaggctca gaaaggatta    35400
tcttcgagtt cataagaaca ggcagaaagt caggttatcg tgttatcgat ataacagta    35460 atgcagataa tttatctgat taacttaatt tattttttgca ataaacgttt ttagcaccat    35520
gaaaaataat aagaaagaat cctgattatg ttgagagagt atacaaaagt ataaaaatgg    35580
cgaattaaat caccattctg atagtgacaa ttattcccctt acttttatag tataatttt    35640 attgaactct ttccctgcgt acattgtacc caaagtaaat cctaccactt caattttat    35700 caattctgtc ttctttgggg tacctgttat atttatatga tgataatcctt ttcttatttc    35760 tttttttcca ccctatagga aagaactatc ttttggattc catgttagtc ctgagccagt    35820
aggatgaatt tttacccaaa cgcttttttc attcaatgca cctcctgtga tggtaattga    35880
tgcctgatat ggttcattta tcactgcatc aggaagaaac tctgattttg gtaaaactt    35940 tggcgttgga ttaccacaac cataaagtaa aaaataaaa ataattaata ttttttttcat    36000 gttatttcat tggtttaaaa accaaccctc aaaaaatatg gttgagtaca taatctagtg    36060
atttgttttt tttaatttga tgttccactt taccccatga aaacagattt aaatttacat    36120
attgattcag atctgaatta tttgtgatat tttctttctc atagttttct actactcctt    36180
cccaaactat ccaatgattt tttcctgatg tttctatgtc accaaaatct gataacattc    36240
ctgctgaaat caaagtaaca acatgatatc ctttgttata gtaatcacta agagttacta    36300
tgtcatttat attagaatgg gataagccga cattactaaa tacttttttca taccctgatt    36360 tttcaaacca ttctgtcaat tttccccaca ttgtaatacc agctacttca tcatcaacct    36420
catcataact catcatcata ttttctgaat ctcttaggct tgccaatgtc agccaatcta    36480
acccagatat tctttcacca tattgattat aaaaagtacc tttaggatgt cggcaaccct    36540
cacccagctt aatttccagt tgaccaattt tagttcggcc atattgccat aattctcgtg    36600
cagcttgctc ataaatatct ggtctatcta ttggcaggca ataaaaaaaa gcggcagggc    36660
cacataaact tgctccattt tgatccggat aagttctttt cgataccctg tcctgtattt    36720
atgattcaat tttacttttt tcaaatggat cgtgtgggtg accaatggga tattctttgg    36780
caataaaagt ccgttcagga atggtgattt ttaattcgac ggtattatcc ccgtcgctga    36840
caggttttgt ttcaactgta ctttcaaaat aacaggcatt ttcccgtttt ttctccgaac    36900
aggctttacc ggaagttaat tcaccgaggg tatacatttt cttaaaatgg gtttgcagtg    36960
```

```
ccggaaatat atttgagcca tgtttgcggt gaagcataat ttgcataata taaatcacag    37020
aaagatcgtc gtctatttcc tgcgtgatat gctgttgtgt ttcataatta ctctgtagtt    37080
tctcctgaaa acatcaagc aagatatgga aatttccttt tgcattctga cgataaatgg     37140
ttaagtcata aagcaggttt tcaacaggta cgttggattc tattttttgtc tgaacggtat   37200 aggctggcat ggtattaatc ctttaaaata tgaaattcaa gtttattttt gtcatccgta    37260
agatgccatt gggtgtaacc ttgtttatca gtctttcctt cttttatctg accatccggc    37320
aggcaaaccc gatacttgcg ttcgttaaa agattgccgt catcatccac acaacgataa     37380
cgggcatgat gtttagcggg ttttaccggg gtttcttcaa ccagcggctt cttaagtggc    37440
ttaacattcg agaccccaga taaaagcggc ttgccttctt cacttccggc taattgcgta    37500
atgctgtagc ccgaagtccc tgcggcgatg tggttgcatg aaatggactt ataatcgagc    37560
atcaccactt catggggtat cgcaccatta tcattgattg aatgcggata attataggaa    37620
atatccacaa tcgtggcact ggtcagcttg atttcataaa agaactccag ttgtcccatc    37680
tggcttgtcc tgtaatgcac aaaactggca tccagcaaac aggggagagg atttatcaat    37740
gggtttcaca aaactgacgg gttgatgatt aacattctgg tcacggctca tcgaatgatt    37800
caggctcaat acctgtattt gatcacacag gccagctggt ttgcccgttc gttaagctgg    37860
cggtaggtca gtgttgcgcc ttcaaacacc agtgccccgt tatccggtgt cctttccacc    37920
tgagcttcaa acagttgtgg cagggttttg tcctgtggat aaggcgcatc ggtctggttc    37980
caggtatgca gcagggtatg cgctcctgt gcggacagaa tatccagcgc ggacagcggt     38040
tgtttctggt ctgccacaaa ggcttccagt acccgttgat agctctctgt cagcctgacg    38100
atggtggttt cattaaacag gctgactgcg taattcaggc aaccggtaat ctcggtttgt    38160
ccgtcggaca taaacaggct gaggtcaaac ttggcggggc tgtatagcgg ctcatccaga    38220
gtcaccggcc tgaatggcag gcggttgtct gacggatttt ctccaaagct ctgtaaacca    38280
aacatgatct gaaaaatcgg gtggcgggcg gtatcacgtt caatattcag ggcatcaagg    38340
agctgttcaa acggcatatc ctgataggcc ttggcttcgg caacctgttt atgggtctgc    38400
tcaatcaggg cttccacgct gacagtctgt tgcaactgtg cccttaagac cagtgaattg    38460
acaaacatcc caatcagggg ctgagtctgg gcatggtggc ggttatcggt tggcgtcccc    38520
agtacgatat cgttttgccc ggataatttt gccagcgtga cataaaaggc actgagcaac    38580
acggtataca gggtggtttc ctgtgttttt gccagactcc ttaactgttc agatagccgg    38640
gtattcagcc caaaactgaa attacatccc tgataattca cctgagccgg tctggggtaa    38700
tcggttggca aggccagtga ttcatagttg gctaaagcct gttgccagta agcgagttgg    38760
cgttcgcgcc ggtcccttg taaatagttg cgttgccatg cggcataatc gccataggtg     38820
atatccagcg ctgcaagctg gctgtcgcg ttttcccgca aggactggta aatttccgcc     38880
agttcagcca taaagatatc aattgaccag ccatcaatgg cgatatggtg ccataacaat    38940
aataaatagt ggctgtcaga aaccggatag tgacacaggc gcagactggg ttctgtggtc    39000
agatc                                                               39005
```

<210> SEQ ID NO 7
<211> LENGTH: 1533
<212> TYPE: DNA
<213> ORGANISM: Xenorhabdus nematophilus

<400> SEQUENCE: 7

```
gatcaggtat tcaatcaacc caaactgttt gatgaacctt tctttgttga taatcgtact      60
tttgattaca acgccattcg tggtaatgat gcacgaacaa ttaagcaact gtgcgccgga     120
ttgaaaatca ccgtagccac cttccaattg ttagctgagc aggtaaacac cgcctttcat     180
ctgccatccg gcaaattaac ctgttcactg cctgttattt cagcgcttta tcgtctggtg     240
actgttcctc ggttatttaa tttaaccgct gaacagggca tgatgctgat taacgcatta     300
aatgccagcg agaaattctc acctcatatt ctggctggtg agcctcgatt aagcctgtta     360
acaacagagg gttcagatac cacagaggtc gatttattgg atgttattct gatgttggaa     420
gaagttgctg tctggctgca acagagcaaa ctgaaaccgg aagaattctg cctgatgctg     480
caaagtgtta tgttgccggt ggttgccacg gacagcagtg tgacattctt cgacaacctg     540
ctgcaaggca ttcccaaaac cttactcaca gaagataact tcaacgcagg ggatatcccc     600
agactccctg aaggagaaac ctggtttgac aaactttcga tgctgataac cagcgatgga     660
ctcgtcaacg tttaccctct cagttggggc cagagtgatg aagattatct gaaatcagta     720
ttgacacctg tcgtcgaaaa aatcattagc gatccaaaca gtgtgattat cactgttttcc    780 gcattaacac aggtcattac tcaggcgaaa actgcgcagg aagatctggt ttccgccagc     840
gtgacacggg aatacggtac tggacgtgat atcgttcctt ggttattacg ctggattggc     900
agcagtgttc ccgatttcct tggcaaaatt tatatacaag cgcaaccag aggcggacac     960 ttgcgcactc cgccggatat cagcgctgaa ttactgcata tcacctatca tctggcgatg    1020
aataacatgc tgattaagca gttacgactc aaagctcaaa tcatttcatt acgtatcatc    1080
atgcctgaat ggctcggatt accaacgata gatggcagtc cgctatccgt gcatgaaatt    1140
tgggcactga ccggttccg taactgggcg accagctcat tgttcagtga agacgagtta    1200
atcgagtatt ttgcttttgc caatcagccg gagcaggacg ttcgtaacga tgaagatttt    1260
aatcgggact gtgctgaaaa gcttgccgac atactggaat gggatgccga tgaaattgag    1320
ctggcaaccc gacattttga tcctgcccca gcacgtgcca gaaatatggg acaaattgac    1380
tggctgcgtc gtgtcatggc gttgtcgcgt cagactggcc tgtcagtgac accgttaatg    1440
acagccgcaa cgttaccgcc tttcccgccc tatgaccaga taacccatgt cggtgaagcg    1500
gtgattgcgg caacccagta cccatcagag gag                                 1533
```

<210> SEQ ID NO 8
<211> LENGTH: 511
<212> TYPE: PRT
<213> ORGANISM: Xenorhabdus nematophilus

<400> SEQUENCE: 8

```
Asp Gln Val Phe Asn Gln Pro Lys Leu Phe Asp Glu Pro Phe Val
1               5                   10                  15

Asp Asn Arg Thr Phe Asp Tyr Asn Ala Ile Arg Gly Asn Asp Ala Arg
            20                  25                  30

Thr Ile Lys Gln Leu Cys Ala Gly Leu Lys Ile Thr Val Ala Thr Phe
        35                  40                  45

Gln Leu Leu Ala Glu Gln Val Asn Thr Ala Phe His Leu Pro Ser Gly
    50                  55                  60

Lys Leu Thr Cys Ser Leu Pro Val Ile Ser Ala Leu Tyr Arg Leu Val
65                  70                  75                  80

Thr Val Pro Arg Leu Phe Asn Leu Thr Ala Glu Gln Gly Met Met Leu
                85                  90                  95

Ile Asn Ala Leu Asn Ala Ser Glu Lys Phe Ser Pro His Ile Leu Ala
```

```
                    100                 105                 110
Gly Glu Pro Arg Leu Ser Leu Leu Thr Thr Glu Gly Ser Asp Thr Thr
            115                 120                 125

Glu Val Asp Leu Leu Asp Val Ile Leu Met Leu Glu Glu Val Ala Val
130                 135                 140

Trp Leu Gln Gln Ser Lys Leu Lys Pro Glu Glu Phe Cys Leu Met Leu
145                 150                 155                 160

Gln Ser Val Met Leu Pro Val Ala Thr Asp Ser Val Thr Phe
                165                 170                 175

Phe Asp Asn Leu Leu Gln Gly Ile Pro Lys Thr Leu Leu Thr Glu Asp
            180                 185                 190

Asn Phe Asn Ala Gly Asp Ile Pro Arg Leu Pro Glu Gly Glu Thr Trp
            195                 200                 205

Phe Asp Lys Leu Ser Met Leu Ile Thr Ser Asp Gly Leu Val Asn Val
            210                 215                 220

Tyr Pro Leu Ser Trp Gly Gln Ser Asp Glu Asp Tyr Leu Lys Ser Val
225                 230                 235                 240

Leu Thr Pro Val Val Glu Lys Ile Ile Ser Asp Pro Asn Ser Val Ile
                245                 250                 255

Ile Thr Val Ser Ala Leu Thr Gln Val Ile Thr Gln Ala Lys Thr Ala
            260                 265                 270

Gln Glu Asp Leu Val Ser Ala Ser Val Thr Arg Glu Tyr Gly Thr Gly
            275                 280                 285

Arg Asp Ile Val Pro Trp Leu Leu Arg Trp Ile Gly Ser Ser Val Pro
290                 295                 300

Asp Phe Leu Gly Lys Ile Tyr Ile Gln Gly Ala Thr Arg Gly Gly His
305                 310                 315                 320

Leu Arg Thr Pro Pro Asp Ile Ser Ala Glu Leu Leu His Ile Thr Tyr
                325                 330                 335

His Leu Ala Met Asn Asn Met Leu Ile Lys Gln Leu Arg Leu Lys Ala
            340                 345                 350

Gln Ile Ile Ser Leu Arg Ile Ile Met Pro Glu Trp Leu Gly Leu Pro
            355                 360                 365

Thr Ile Asp Gly Ser Pro Leu Ser Val His Glu Ile Trp Ala Leu Ser
370                 375                 380

Arg Phe Arg Asn Trp Ala Thr Ser Ser Leu Phe Ser Glu Asp Glu Leu
385                 390                 395                 400

Ile Glu Tyr Phe Ala Phe Ala Asn Gln Pro Glu Gln Asp Val Arg Asn
                405                 410                 415

Asp Glu Asp Phe Asn Arg Asp Cys Ala Glu Lys Leu Ala Asp Ile Leu
            420                 425                 430

Glu Trp Asp Ala Asp Glu Ile Glu Leu Ala Thr Arg His Phe Asp Pro
            435                 440                 445

Ala Pro Ala Arg Ala Arg Asn Met Gly Gln Ile Asp Trp Leu Arg Arg
            450                 455                 460

Val Met Ala Leu Ser Arg Gln Thr Gly Leu Ser Val Thr Pro Leu Met
465                 470                 475                 480

Thr Ala Ala Thr Leu Pro Pro Phe Pro Pro Tyr Asp Gln Ile Thr His
                485                 490                 495

Val Gly Glu Ala Val Ile Ala Ala Thr Gln Tyr Pro Ser Glu Glu
            500                 505                 510

<210> SEQ ID NO 9
```

<211> LENGTH: 4173
<212> TYPE: DNA
<213> ORGANISM: Xenorhabdus nematophilus

<400> SEQUENCE: 9

| | | | | | |
|---|---|---|---|---|---|
| atgagttcag | ttacccaacc | tattgaagag | cgtttactgg | aatcacagcg | cgacgcactg | 60 |
| ctggatttct | atctcggaca | ggtcgttgcc | tattcacctg | acatgacaag | tcagcgcgac | 120 |
| aaaattaagg | atattgacga | tgcctgcgac | tacctcctgc | tggatctgct | gacttccgcc | 180 |
| aaagtcaaag | cgacacgact | ttcacttgcg | accaattcat | tgcagcaatt | tgtgaaccgc | 240 |
| gtgtcactga | atattgaacc | cggtttgttt | atgaccgcgg | aagagagcga | aaattggcag | 300 |
| gaatttgcga | tcgttataa | ttactggtct | gcggatcgct | tattacggac | ttatccggaa | 360 |
| agctatctgg | aacccctgtt | acgcctgaat | aaaacagaat | tcttcttcca | actgaaaagt | 420 |
| gcccttaatc | agggaaaaat | taccgaagat | tccgtacaac | aagcggtgct | cggttatctg | 480 |
| aataattttg | aagatgtcag | taacctgaaa | gttatcgcag | gttatgaaga | tggtgttaac | 540 |
| atcaaacgcg | ataagttctt | ctttgtcgga | cgtacccgta | cacagccata | ccaatattac | 600 |
| tggcgttcac | tgaatctttc | gatacgccat | cctgataccg | atgcgttatc | tcccaatgcc | 660 |
| tggagcgagt | ggaaacctat | tgacctgcca | ttgggcagcg | tagaccccaa | tttgatacgc | 720 |
| cccatttttcc | tgaataatcg | cctgtatatt | gcctggacgg | aagttgaaga | acagtctgaa | 780 |
| actaaagata | caactgcgtt | atcactgcat | aaccaaaacg | ttgagcctag | tgcgggtgat | 840 |
| tgggttcctc | ccacaccgtt | cctgacccgg | atcaaaatcg | cttatgccaa | atatgatggc | 900 |
| agctggagta | cacccaccat | tctgcgcgaa | gacaatctgc | aataccggat | ggcccagatg | 960 |
| gttgctgtga | tggatataca | gcaagacccg | cataacccgt | ttctggctct | ggttccgttt | 1020 |
| gtccgtcttc | agggggacaga | taagaaaggt | aaggattatg | attatgacga | agccttcggt | 1080 |
| tatgtctgcg | atacactgct | ggtagaaatt | actgatttgc | cggatgacga | atatgctgat | 1140 |
| ggacgaaaag | gaaaatatgt | cggcaacctg | gtctggtatt | actcacgtga | acacaaggat | 1200 |
| gcagaaggca | atcctatcga | ttaccgtact | atggtgctct | atccggcaac | ccggaagaa | 1260 |
| cgctttccta | ttgccggaga | agccaaaccg | gaaggaagcc | ctgattttgg | caaagacagt | 1320 |
| atcaaactga | ttgtcaattt | tgttcatggc | actgatgaca | cactggagat | tgtcgctcaa | 1380 |
| tctgactta | agtttggtgc | gatagaagat | catcaatatt | acaacggttc | tttccggctg | 1440 |
| atgcacgata | atactgtctt | ggatgaacaa | ccactggtac | tgaacgaaaa | agttcctgat | 1500 |
| ttaacctatc | catcaatcaa | gctggggtcg | gataatcgaa | tcaccctgaa | agccgaactt | 1560 |
| ctctttaagc | ccaaaggtgg | tgttggcaat | gaaagtgcca | gctgtactca | agagttcaga | 1620 |
| atcggtatgc | acattcgcga | actgattaaa | ctcaatgaac | aggatcaggt | gcaattcctt | 1680 |
| tccttccccg | cagatgaaac | tggtaacgcg | ccacaaaaca | ttcgccttaa | tacactgttt | 1740 |
| gcaaaaaaac | tgatcgccat | tgccagtcag | ggtatcccgc | aggtactgag | ctggaataca | 1800 |
| cagcttatta | ctgaacaacc | catacccggt | tcattcccta | cgccgattga | tttaaatggc | 1860 |
| gcaaatggga | tctatttctg | ggaactgttt | ttccatatgc | catttctggt | cgcgtggcga | 1920 |
| ctgaatatcg | aacaacgatt | aaaagaggcc | accgaatggc | tgcactatat | ttttaatccg | 1980 |
| ctggaagatg | aacttgttca | ggccagcaac | caagtaaac | cgcgttactg | gaattcacgg | 2040 |
| ccaattattg | atcctccacc | caccgtgtac | cggatgttaa | ttgaaccaac | cgatccggat | 2100 |
| gccattgcag | ccagtgaacc | cattcactac | cggaaagcaa | tattccgttt | ctatgtcaag | 2160 |
| aatctgttag | atcagggaga | catggaatac | cgtaagctga | catccagtgc | acgtactgtc | 2220 |

-continued

```
gccaagcaga tctatgactc cgtcaatatg ttactgggta ccagccctga tattctgctc    2280
gcggcaaact ggcaaccccg tacgctgcaa gatgtggctc tgtatgaaaa cagtgaagca    2340
cgggcacagg agttaatgct tactgtcagc agcgtgccac ttctgcctgt gacatatgat    2400
acatccgtct ctgccgcacc gtctgattta tttgtcaaac ctgttgatac ggaatatctc    2460
aaactgtggc aaatgttgga tcagcgtcta taaacttac gtcataacct gaccttggat     2520
ggtaaagagt ttccggccgg attatacgat gaacccatca gcccgcaaga tctgctcagg    2580
cagcgttacc agcgtgttgt ggctaatcgt atggcgggca tgaaacgccg gcaatcccg     2640 aattatcgtt tcaccccgat catgagccgg gcaaagagg ccgcagaaac gctgattcag     2700
tacggcagca cgttactgag tttgctggag aaaaaagaca ataccgattt tgaacacttc    2760
cgtatgcagc agcaactggg gctgtacagc tttacccgca atctgcaaca gcaagcgatt    2820
gacatgcaac aggcttcatt ggatgcactg accatcagcc gacgggccgc tcaggagcgc    2880
cagcaacact ataaatcgct ctatgatgaa acatctcca tcaccgagca ggaagttatc     2940
gcattacaat caagagcggc tgaaggtgtg atcgctgccc agtcagccgc cactgcggcc    3000
gctgtggcgg atatggttcc caatattttc ggtctggccg tcgggggat ggtctttggc     3060 ggtatgcttc gggcaatcgg tgaaggaata cgcattgacg ttgaaagtaa aaatgccaaa    3120
gccaccagcc tgagcgtgtc agaaaattac cgtcgccgtc agcaagaatg ggagctgcaa    3180
tacaaacagg cggatatcaa cattgaggag atcgacgcac agattggtat ccagcaacgc    3240
caactgaata tcagcacaac ccaactggca caattggaag cccagcatga gcaggatcaa    3300
gtcctgctgg agtactattc aaaccgtttt accaatgatg cgttatacat gtggatgatc    3360
agccaaatct ccgggcttta cctgcaagcc tatgatgcgg ttaattccct ctgtttactg    3420
gccgaagcct cctggcagta cgaaacaggt cagtatgata tgaatttcgt ccaaagtggt    3480
ctctggaatg atctttatca ggggctgctg gtcggagaac atctgaaatt agccttacaa    3540
cggatggatc aggcgtattt gcaacataac accagacgtc tggagatcat aaaaaccata    3600
tcggtaaaat cattactgac atcatcacag tgggaaattg caagagtac gggttcattc     3660 actttcttac tgagcgccga aatgttcttg cgcgattatc cgacccacgc tgatcggcgt    3720
ataaaaaccg tagcgctgtc attgcccgca ttgctgggc cttatgaaga tgtacgggct     3780
tcactggtac aactcagcaa tacgctttac agtactgctg acttaaaaac tatcgattat    3840
ttgcttaacc ccttggaata caccaaaccc gaaaacgttt tgctgaacgt acaggctaat    3900
caaggtgtgg tgatttcaac ggccatggaa gacagcggca tgttcaggct caattttgat    3960
gatgaacttt tcctgccttt tgaagggaca ggcgccattt cacagtggaa gttggaattc    4020
ggttccgatc aggatcagct gctggagtcg ctgagcgata ttatcctcca tctgcgttat    4080
accgcgcgtg atgtgagtgg cggaagtaat gagttcagcc agcaggttcg tagccgtctg    4140
aataaacatc aattaaaaca agacaattct aac                                 4173
```

<210> SEQ ID NO 10
<211> LENGTH: 1391
<212> TYPE: PRT
<213> ORGANISM: Xenorhabdus nematophilus

<400> SEQUENCE: 10

Met Ser Ser Val Thr Gln Pro Ile Glu Glu Arg Leu Leu Glu Ser Gln
1               5                   10                  15

Arg Asp Ala Leu Leu Asp Phe Tyr Leu Gly Gln Val Val Ala Tyr Ser

-continued

```
                  20                  25                  30
Pro Asp Met Thr Ser Gln Arg Asp Lys Ile Lys Asp Ile Asp Asp Ala
             35                  40                  45
Cys Asp Tyr Leu Leu Leu Asp Leu Leu Thr Ser Ala Lys Val Lys Ala
 50                  55                  60
Thr Arg Leu Ser Leu Ala Thr Asn Ser Leu Gln Gln Phe Val Asn Arg
 65                  70                  75                  80
Val Ser Leu Asn Ile Glu Pro Gly Leu Phe Met Thr Ala Glu Glu Ser
                 85                  90                  95
Glu Asn Trp Gln Glu Phe Ala Asn Arg Tyr Asn Tyr Trp Ser Ala Asp
            100                 105                 110
Arg Leu Leu Arg Thr Tyr Pro Glu Ser Tyr Leu Glu Pro Leu Leu Arg
            115                 120                 125
Leu Asn Lys Thr Glu Phe Phe Gln Leu Glu Ser Ala Leu Asn Gln
            130                 135                 140
Gly Lys Ile Thr Glu Asp Ser Val Gln Gln Ala Val Leu Gly Tyr Leu
145                 150                 155                 160
Asn Asn Phe Glu Asp Val Ser Asn Leu Lys Val Ile Ala Gly Tyr Glu
                165                 170                 175
Asp Gly Val Asn Ile Lys Arg Asp Lys Phe Phe Val Gly Arg Thr
            180                 185                 190
Arg Thr Gln Pro Tyr Gln Tyr Trp Arg Ser Leu Asn Leu Ser Ile
            195                 200                 205
Arg His Pro Asp Thr Asp Ala Leu Ser Pro Asn Ala Trp Ser Glu Trp
            210                 215                 220
Lys Pro Ile Asp Leu Pro Leu Gly Ser Val Asp Pro Asn Leu Ile Arg
225                 230                 235                 240
Pro Ile Phe Leu Asn Asn Arg Leu Tyr Ile Ala Trp Thr Glu Val Glu
                245                 250                 255
Glu Gln Ser Glu Thr Lys Asp Thr Thr Ala Leu Ser Leu His Asn Gln
            260                 265                 270
Asn Val Glu Pro Ser Ala Gly Asp Trp Val Pro Pro Thr Pro Phe Leu
            275                 280                 285
Thr Arg Ile Lys Ile Ala Tyr Ala Lys Tyr Asp Gly Ser Trp Ser Thr
            290                 295                 300
Pro Thr Ile Leu Arg Glu Asp Asn Leu Gln Tyr Arg Met Ala Gln Met
305                 310                 315                 320
Val Ala Val Met Asp Ile Gln Gln Asp Pro His Asn Pro Phe Leu Ala
                325                 330                 335
Leu Val Pro Phe Val Arg Leu Gln Gly Thr Asp Lys Gly Lys Asp
            340                 345                 350
Tyr Asp Tyr Asp Glu Ala Phe Gly Tyr Val Cys Asp Thr Leu Leu Val
            355                 360                 365
Glu Ile Thr Asp Leu Pro Asp Asp Glu Tyr Ala Asp Gly Arg Lys Gly
            370                 375                 380
Lys Tyr Val Gly Asn Leu Val Trp Tyr Tyr Ser Arg Glu His Lys Asp
385                 390                 395                 400
Ala Glu Gly Asn Pro Ile Asp Tyr Arg Thr Met Val Leu Tyr Pro Ala
                405                 410                 415
Thr Arg Glu Glu Arg Phe Pro Ile Ala Gly Glu Ala Lys Pro Glu Gly
            420                 425                 430
Ser Pro Asp Phe Gly Lys Asp Ser Ile Lys Leu Ile Val Asn Phe Val
            435                 440                 445
```

```
His Gly Thr Asp Asp Thr Leu Glu Ile Val Ala Gln Ser Asp Phe Lys
        450                 455                 460

Phe Gly Ala Ile Glu Asp His Gln Tyr Tyr Asn Gly Ser Phe Arg Leu
465                 470                 475                 480

Met His Asp Asn Thr Val Leu Asp Glu Gln Pro Leu Val Leu Asn Glu
                485                 490                 495

Lys Val Pro Asp Leu Thr Tyr Pro Ser Ile Lys Leu Gly Ser Asp Asn
            500                 505                 510

Arg Ile Thr Leu Lys Ala Glu Leu Leu Phe Lys Pro Lys Gly Gly Val
        515                 520                 525

Gly Asn Glu Ser Ala Ser Cys Thr Gln Glu Phe Arg Ile Gly Met His
    530                 535                 540

Ile Arg Glu Leu Ile Lys Leu Asn Glu Gln Asp Gln Val Gln Phe Leu
545                 550                 555                 560

Ser Phe Pro Ala Asp Glu Thr Gly Asn Ala Pro Gln Asn Ile Arg Leu
                565                 570                 575

Asn Thr Leu Phe Ala Lys Lys Leu Ile Ala Ile Ala Ser Gln Gly Ile
            580                 585                 590

Pro Gln Val Leu Ser Trp Asn Thr Gln Leu Ile Thr Glu Gln Pro Ile
        595                 600                 605

Pro Gly Ser Phe Pro Thr Pro Ile Asp Leu Asn Gly Ala Asn Gly Ile
    610                 615                 620

Tyr Phe Trp Glu Leu Phe Phe His Met Pro Phe Leu Val Ala Trp Arg
625                 630                 635                 640

Leu Asn Ile Glu Gln Arg Leu Lys Glu Ala Thr Glu Trp Leu His Tyr
                645                 650                 655

Ile Phe Asn Pro Leu Glu Asp Glu Leu Val Gln Ala Ser Asn Gln Gly
            660                 665                 670

Lys Pro Arg Tyr Trp Asn Ser Arg Pro Ile Ile Asp Pro Pro Pro Thr
        675                 680                 685

Val Tyr Arg Met Leu Ile Glu Pro Thr Asp Pro Asp Ala Ile Ala Ala
    690                 695                 700

Ser Glu Pro Ile His Tyr Arg Lys Ala Ile Phe Arg Phe Tyr Val Lys
705                 710                 715                 720

Asn Leu Leu Asp Gln Gly Asp Met Glu Tyr Arg Lys Leu Thr Ser Ser
                725                 730                 735

Ala Arg Thr Val Ala Lys Gln Ile Tyr Asp Ser Val Asn Met Leu Leu
            740                 745                 750

Gly Thr Ser Pro Asp Ile Leu Leu Ala Ala Asn Trp Gln Pro Arg Thr
        755                 760                 765

Leu Gln Asp Val Ala Leu Tyr Glu Asn Ser Glu Ala Arg Ala Gln Glu
    770                 775                 780

Leu Met Leu Thr Val Ser Ser Val Pro Leu Leu Pro Val Thr Tyr Asp
785                 790                 795                 800

Thr Ser Val Ser Ala Ala Pro Ser Asp Leu Phe Val Lys Pro Val Asp
                805                 810                 815

Thr Glu Tyr Leu Lys Leu Trp Gln Met Leu Asp Gln Arg Leu Tyr Asn
            820                 825                 830

Leu Arg His Asn Leu Thr Leu Asp Gly Lys Glu Phe Pro Ala Gly Leu
        835                 840                 845

Tyr Asp Glu Pro Ile Ser Pro Gln Asp Leu Leu Arg Gln Arg Tyr Gln
    850                 855                 860
```

```
Arg Val Val Ala Asn Arg Met Ala Gly Met Lys Arg Ala Ile Pro
865                 870                 875                 880

Asn Tyr Arg Phe Thr Pro Ile Met Ser Arg Ala Lys Glu Ala Ala Glu
                885                 890                 895

Thr Leu Ile Gln Tyr Gly Ser Thr Leu Leu Ser Leu Leu Glu Lys Lys
            900                 905                 910

Asp Asn Thr Asp Phe Glu His Phe Arg Met Gln Gln Gln Leu Gly Leu
        915                 920                 925

Tyr Ser Phe Thr Arg Asn Leu Gln Gln Gln Ala Ile Asp Met Gln Gln
    930                 935                 940

Ala Ser Leu Asp Ala Leu Thr Ile Ser Arg Arg Ala Ala Gln Glu Arg
945                 950                 955                 960

Gln Gln His Tyr Lys Ser Leu Tyr Asp Glu Asn Ile Ser Ile Thr Glu
                965                 970                 975

Gln Glu Val Ile Ala Leu Gln Ser Arg Ala Ala Glu Gly Val Ile Ala
            980                 985                 990

Ala Gln Ser Ala Ala Thr Ala Ala  Ala Val Ala Asp Met  Val Pro Asn
        995             1000                 1005

Ile Phe Gly Leu Ala Val Gly  Gly Met Val Phe  Gly Gly Met Leu
    1010                1015                1020

Arg Ala Ile Gly Glu Gly Ile  Arg Ile Asp Val Glu  Ser Lys Asn
    1025                1030                1035

Ala Lys Ala Thr Ser Leu Ser  Val Ser Glu Asn Tyr  Arg Arg Arg
    1040                1045                1050

Gln Gln  Glu Trp Glu Leu Gln  Tyr Lys Gln Ala Asp  Ile Asn Ile
    1055                1060                1065

Glu Glu  Ile Asp Ala Gln Ile  Gly Ile Gln Arg  Gln Leu Asn
    1070                1075                1080

Ile Ser  Thr Thr Gln Leu Ala  Gln Leu Glu Ala Gln  His Glu Gln
    1085                1090                1095

Asp Gln  Val Leu Leu Glu Tyr  Tyr Ser Asn Arg Phe  Thr Asn Asp
    1100                1105                1110

Ala Leu  Tyr Met Trp Met Ile  Ser Gln Ile Ser Gly  Leu Tyr Leu
    1115                1120                1125

Gln Ala  Tyr Asp Ala Val Asn  Ser Leu Cys Leu Leu  Ala Glu Ala
    1130                1135                1140

Ser Trp  Gln Tyr Glu Thr Gly  Gln Tyr Asp Met Asn  Phe Val Gln
    1145                1150                1155

Ser Gly  Leu Trp Asn Asp Leu  Tyr Gln Gly Leu Leu  Val Gly Glu
    1160                1165                1170

His Leu  Lys Leu Ala Leu Gln  Arg Met Asp Gln Ala  Tyr Leu Gln
    1175                1180                1185

His Asn  Thr Arg Arg Leu Glu  Ile Ile Lys Thr Ile  Ser Val Lys
    1190                1195                1200

Ser Leu  Leu Thr Ser Ser Gln  Trp Glu Ile Gly Lys  Ser Thr Gly
    1205                1210                1215

Ser Phe  Thr Phe Leu Leu Ser  Ala Glu Met Phe Leu  Arg Asp Tyr
    1220                1225                1230

Pro Thr  His Ala Asp Arg Arg  Ile Lys Thr Val Ala  Leu Ser Leu
    1235                1240                1245

Pro Ala  Leu Leu Gly Pro Tyr  Glu Asp Val Arg Ala  Ser Leu Val
    1250                1255                1260

Gln Leu  Ser Asn Thr Leu Tyr  Ser Thr Ala Asp Leu  Lys Thr Ile
```

```
                              1265                1270                 1275
          Asp Tyr Leu Leu Asn Pro Leu Glu Tyr Thr Lys Pro Glu Asn Val
              1280                1285                1290

Leu Leu Asn Val Gln Ala Asn Gln Gly Val Val Ile Ser Thr Ala
              1295                1300                1305

Met Glu Asp Ser Gly Met Phe Arg Leu Asn Phe Asp Asp Glu Leu
              1310                1315                1320

Phe Leu Pro Phe Glu Gly Thr Gly Ala Ile Ser Gln Trp Lys Leu
              1325                1330                1335

Glu Phe Gly Ser Asp Gln Asp Gln Leu Leu Glu Ser Leu Ser Asp
              1340                1345                1350

Ile Ile Leu His Leu Arg Tyr Thr Ala Arg Asp Val Ser Gly Gly
              1355                1360                1365

Ser Asn Glu Phe Ser Gln Gln Val Arg Ser Arg Leu Asn Lys His
              1370                1375                1380

Gln Leu Lys Gln Asp Asn Ser Asn
              1385                1390

<210> SEQ ID NO 11
<211> LENGTH: 1944
<212> TYPE: DNA
<213> ORGANISM: Xenorhabdus nematophilus

<400> SEQUENCE: 11
atgtctcaaa atgtttatcg ataccctttca attaaagcga tgtctgacgc cagcagcgaa       60
gtaggcgcat ctctggttgc ctggcagaat caatctggtg gtcaaacctg gtatgtcatt      120
tatgatagcg cggttttttaa aaacatcggc tgggttgaac gctggcatat tcccgaccgc      180
aatatttcac ctgatttacc ggtttatgag aatgcctggc aatatgtccg tgaggcgaca      240
ccggaagaaa ttgccgatca cggtaacccc aatacgcctg atgtaccgcc gggagaaaaa      300
accgaggtat tgcaatatga tgcactcaca gaagaaacct atcagaaggt gggatataaa      360
cctgacggca gcggaactcc tttgagttat tcttcagcac gtgttgccaa gtccctgtac      420
aacgaatatg aagttgatcc ggaaaataca gaaccgctgc ctaaagtctc tgcctatatt      480
actgactggt gccagtatga tgcgcgtttg tcgccagaaa cccaggataa cactgcgctg      540
accagcgacg atgcccccgg ccgtggtttt gatctggaaa aaatcccgcc taccgcctac      600
gaccgcctga ttttcagttt tatggccgtc aacggtgata aaggcaagtt atccgaacgg      660
attaatgagg ttgttgacgg gtggaaccgg caagcagaag ccagcagtgg ccagattgcc      720
cctattacat taggccatat tgtacccgtt gatccttatg gtgatttagg caccacacgc      780
aatgtcggtc tggacgcgga tcagcgccgt gatgccagcc cgaagaattt cttgcaatat      840
tacaatcagg atgcagcctc cggtttactg ggggattgc gtaatctgaa agcgcgagca      900
aaacaggcag ggcacaagct ggaactcgca ttcagtatcg gcggctggag tatgtcaggg      960
tatttctctg tgatggccaa agatcctgag caacgtgcta catttgtgag tagcatcgtc     1020
gacttcttcc ggcgttttcc catgtttact gcggtggata tcgactggga ataccccggc     1080
gccacaggtg aagaaggtaa tgaattcgac ccggaacatg atggcccaaa ctatgttttg     1140
ttagtgaaag agctgcgtga agcactgaac atcgcctttg aacccgggcc cgtaaagaa      1200 atcacgatag cctgtagcgc cgtcgttgcc aaaatggaga gtccagcttc aaagaaatc     1260 gcaccttatt tagacaatat ctttgtgatg acctacgact tctttggtac cggttgggca     1320
gaatacatcg gtcaccatac taacctgtat cccccccagat atgaatatga cggcgataac     1380
```

```
cctcctccgc ccaatcctga tcgggacatg gattactcgg ctgatgaggc gatccgcttt    1440
ttactgtcac aaggtgtaca accggagaaa attcacctcg gatttgctaa ctatggacgt    1500
tcatgtctgg gtgctgatct gacaactcgc cgctataaca aacaggaga gccactgggc     1560 acgatggaaa aagtgctcc ggaattcttc tgtctgctga ataaccaata cgatgcggaa    1620
tatgaaattg cacgcgggaa aaatcagttt gaactggtga cagacacgga aaccgacgct    1680
gacgcactct ttaatgctga cggtggtcac tggatttcac tggatacgcc ccgcactgtg    1740
ctgcataagg gaatttatgc aaccaaaatg aaattgggcg ggatcttctc ttggtcaggc    1800
gatcaggatg atggcctgtt ggcaaatgct gctcacgaag gtttgggtta cttacctgta    1860
cgcggaaaag agaagattga tatgggaccg ttatataaca aaggacgtct cattcagctt    1920
cctaaagtaa cccgtcgtaa atcg                                           1944
```

<210> SEQ ID NO 12
<211> LENGTH: 648
<212> TYPE: PRT
<213> ORGANISM: Xenorhabdus nematophilus

<400> SEQUENCE: 12

```
Met Ser Gln Asn Val Tyr Arg Tyr Pro Ser Ile Lys Ala Met Ser Asp
1               5                   10                  15

Ala Ser Ser Glu Val Gly Ala Ser Leu Val Ala Trp Gln Asn Gln Ser
            20                  25                  30

Gly Gly Gln Thr Trp Tyr Val Ile Tyr Asp Ser Ala Val Phe Lys Asn
        35                  40                  45

Ile Gly Trp Val Glu Arg Trp His Ile Pro Asp Arg Asn Ile Ser Pro
    50                  55                  60

Asp Leu Pro Val Tyr Glu Asn Ala Trp Gln Tyr Val Arg Glu Ala Thr
65                  70                  75                  80

Pro Glu Glu Ile Ala Asp His Gly Asn Pro Asn Thr Pro Asp Val Pro
                85                  90                  95

Pro Gly Glu Lys Thr Glu Val Leu Gln Tyr Asp Ala Leu Thr Glu Glu
            100                 105                 110

Thr Tyr Gln Lys Val Gly Tyr Lys Pro Asp Gly Ser Gly Thr Pro Leu
        115                 120                 125

Ser Tyr Ser Ser Ala Arg Val Ala Lys Ser Leu Tyr Asn Glu Tyr Glu
    130                 135                 140

Val Asp Pro Glu Asn Thr Glu Pro Leu Pro Lys Val Ser Ala Tyr Ile
145                 150                 155                 160

Thr Asp Trp Cys Gln Tyr Asp Ala Arg Leu Ser Pro Glu Thr Gln Asp
                165                 170                 175

Asn Thr Ala Leu Thr Ser Asp Ala Pro Gly Arg Gly Phe Asp Leu
            180                 185                 190

Glu Lys Ile Pro Pro Thr Ala Tyr Asp Arg Leu Ile Phe Ser Phe Met
        195                 200                 205

Ala Val Asn Gly Asp Lys Gly Lys Leu Ser Glu Arg Ile Asn Glu Val
    210                 215                 220

Val Asp Gly Trp Asn Arg Gln Ala Glu Ala Ser Ser Gly Gln Ile Ala
225                 230                 235                 240

Pro Ile Thr Leu Gly His Ile Val Pro Val Asp Pro Tyr Gly Asp Leu
                245                 250                 255

Gly Thr Thr Arg Asn Val Gly Leu Asp Ala Asp Gln Arg Arg Asp Ala
            260                 265                 270
```

```
Ser Pro Lys Asn Phe Leu Gln Tyr Tyr Asn Gln Asp Ala Ala Ser Gly
        275                 280                 285

Leu Leu Gly Gly Leu Arg Asn Leu Lys Ala Arg Ala Lys Gln Ala Gly
    290                 295                 300

His Lys Leu Glu Leu Ala Phe Ser Ile Gly Gly Trp Ser Met Ser Gly
305                 310                 315                 320

Tyr Phe Ser Val Met Ala Lys Asp Pro Glu Gln Arg Ala Thr Phe Val
                325                 330                 335

Ser Ser Ile Val Asp Phe Phe Arg Arg Phe Pro Met Phe Thr Ala Val
            340                 345                 350

Asp Ile Asp Trp Glu Tyr Pro Gly Ala Thr Gly Glu Glu Gly Asn Glu
        355                 360                 365

Phe Asp Pro Glu His Asp Gly Pro Asn Tyr Val Leu Leu Val Lys Glu
    370                 375                 380

Leu Arg Glu Ala Leu Asn Ile Ala Phe Gly Thr Arg Ala Arg Lys Glu
385                 390                 395                 400

Ile Thr Ile Ala Cys Ser Ala Val Val Ala Lys Met Glu Lys Ser Ser
                405                 410                 415

Phe Lys Glu Ile Ala Pro Tyr Leu Asp Asn Ile Phe Val Met Thr Tyr
            420                 425                 430

Asp Phe Phe Gly Thr Gly Trp Ala Glu Tyr Ile Gly His His Thr Asn
        435                 440                 445

Leu Tyr Pro Pro Arg Tyr Glu Tyr Asp Gly Asp Asn Pro Pro Pro Pro
    450                 455                 460

Asn Pro Asp Arg Asp Met Asp Tyr Ser Ala Asp Glu Ala Ile Arg Phe
465                 470                 475                 480

Leu Leu Ser Gln Gly Val Gln Pro Glu Lys Ile His Leu Gly Phe Ala
                485                 490                 495

Asn Tyr Gly Arg Ser Cys Leu Gly Ala Asp Leu Thr Thr Arg Arg Tyr
            500                 505                 510

Asn Arg Thr Gly Glu Pro Leu Gly Thr Met Glu Lys Gly Ala Pro Glu
        515                 520                 525

Phe Phe Cys Leu Leu Asn Asn Gln Tyr Asp Ala Glu Tyr Glu Ile Ala
    530                 535                 540

Arg Gly Lys Asn Gln Phe Glu Leu Val Thr Asp Thr Glu Thr Asp Ala
545                 550                 555                 560

Asp Ala Leu Phe Asn Ala Asp Gly Gly His Trp Ile Ser Leu Asp Thr
                565                 570                 575

Pro Arg Thr Val Leu His Lys Gly Ile Tyr Ala Thr Lys Met Lys Leu
            580                 585                 590

Gly Gly Ile Phe Ser Trp Ser Gly Asp Gln Asp Asp Gly Leu Leu Ala
        595                 600                 605

Asn Ala Ala His Glu Gly Leu Gly Leu Tyr Leu Pro Val Arg Gly Lys Glu
    610                 615                 620

Lys Ile Asp Met Gly Pro Leu Tyr Asn Lys Gly Arg Leu Ile Gln Leu
625                 630                 635                 640

Pro Lys Val Thr Arg Arg Lys Ser
                645

<210> SEQ ID NO 13
<211> LENGTH: 7569
<212> TYPE: DNA
<213> ORGANISM: Xenorhabdus nematophilus
```

-continued

```
<400> SEQUENCE: 13
atgataaaag ttaatgaact gttagataag ataaatagaa aaggtctgg tgatacttta      60 ttattgacaa acatttcgtt tatgtctttc agcgaatttc gtcataggac aagtggaact    120
ctgacgtggc gagaaacaga ctttttatat caacaggctc atcaggaatc aaaacagaat    180
aaacttgaag aactgcgcat tttgtcccgt gctaatccac aactggctaa taccactaac    240
cttaatatta caccgtcaac cctaaacaat agttacaaca gttggtttta tggccgtgcc    300
caccgttttg taaaaccggg atcaattgct tccatatttt caccagcggc ttatttaaca    360
gaattatatc gggaagcgaa agattttcat cctgacaatt ctcaatatca cctgaataaa    420 cgacgcccg acattgcttc actggcactg acacagaata atatggatga agaaatttcc    480
acattatcct tatctaatga attactgctg cataatattc agacgttaga gaaaactgac    540
tataacggtg taatgaaaat gttgtccact taccggcaaa ccggcatgac accctatcat    600
ctgccgtatg agtcagcccg tcaggcaatt ttattgcaag ataaaaacct caccgcattt    660
agccgtaata cagacgtagc ggaattaatg gacccaacat cgctactggc tattaagact    720
gatatatcgc ctgaattgta tcaaatcctt gtagaagaaa ttcaccggaa aaattcaaca    780
gaactgatga agaaaaattt cggtacagat gatgtactga ttttttaagag ttatgcttct    840 ttggctcgct actacgattt gtcttatgat gaactcagtt tatttgtcaa tctctccttc    900
ggtaagaaaa atacaaatca acagtataag aatgagcaac tgataacatt ggtcaatgac    960
gggaatgata cggcaacggc aagattgatt aagcgaaccc gcaaagattt ctacgattca   1020
catttaaact atgcagaact aattccaatc aaagaaaatg aatacaaata taatttcagt   1080
gtaaaaaaaa cagaacctga ccacttggat tttcgtctcc agaatggaga taagaatat    1140 ataccaag ataaaaattt cgtccccatt gctaataccc attacagtat tcccattaaa     1200
ttgacgacag agcaaatcac caacggtata acactccgct tatggcgagt taaaccaaat   1260
ccgtcggatg ctatcaatgc caatgcatac tttaaaatga tggagttccc cggtgatata   1320
ttcctgttaa agctgaataa agcgattcgt ttgtataaag ccacaggcat atctccagaa   1380
gatatctggc aagtaataga aagtatttat gatgacttaa ccattgacag caatgtgttg   1440
ggtaagctgt tttatgttca atattatatg cagcactata atattagcgt cagcgatgcg   1500
ctggtattgt gtcattcaga tatcagccaa tattccacta acaacaacc cagtcatttt    1560 acaatactgt tcaatacacc gctattaaat ggccaagagt tttctgctga taataccaaa   1620
ctggatttaa cccccggtga atcaaaaaac catttttatt tgggaataat gaaacgtgct   1680
ttcagagtga atgatactga actgtataca ttatggaagc tggctaatgg cggaacaaat   1740
ccagaattta tgtgttccat cgagaacctg tctctgcttt atcgcgttcg tctgctggca   1800
gacattcatc atctgacagt gaatgaatta tccatgttgt tgtcggtttc tccctatgtg   1860
aacacgaaaa ttgcccttt ttctgataca gcattaacgc aattaatcag ctttctgttc    1920
caatgcaccc agtggctgac aacacagaaa tggtctgtca gtgatgtgtt tctgatgacc   1980
acggataatt acagcactgt ccttacgccg gatattgaaa accttatcac gacactaagt   2040
aatggattat caacactttc actcggtgat gacgaactga tccgtgcagc tgccccgctg   2100
attgctgcca gcattcaaat ggattcagcc aagacagcag aaactatttt gctgtggatt   2160
aatcagataa aaccacaagg actgacattc gatgatttca tgattattgc ggctaaccgt   2220
gatcgctcag agaatgaaac cagcaacatg gtggcttttt gtcaggtact ggggcaactt   2280
tctctgattg tgcgcaatat tggactcagc gaaaacgaac tgaccctgtt ggtgacaaaa   2340
```

-continued

```
ccggagaaat tccaatcaga aaccacagca ctgcaacatg atctccccac tttgcaagcg    2400
ctgacccgct tccatgctgt gatcatgcgt tgtggaagct acgcgacaga aatcttaaca    2460
gcattggaac taggagcgct gactgccgaa caattggcgg tggcgttaaa atttgatgct    2520
caggttgtga cacaagcatt gcaacagacc ggtttgggag tgaataccct taccaactgg    2580
agaactatag atgtcactct gcaatggctg gatgtcgctg ctacattggg tattaccccg    2640
gatggtgttg ctgcactcat aaaattaaaa tatatcggtg aaccagaaac cccgatgcca    2700
acatttgatg attggcaagc cgccagtact ttgttcagg cgggactgaa cagtcaacaa    2760
tccgaccagc ttcaggcatg gctggatgaa gccacgacga cagcggccag tgcttactac    2820
atcaaaaata gtgcacctca acagattaag agccgggatg agttgtacag ctatctgctg    2880
attgataacc aagtttctgc ccaagtgaaa accacccgtg tggcagaagc cattgccagc    2940
attcagttat atgtcaaccg ggcgttgaat aatgttgaag gaaaagtatc aaagccagtg    3000
aaaacccgtc agttcttctg cgactgggaa acctacaatc gacggtatag cacctgggcc    3060
ggcgtatctg aactggccta ttatccggaa aactatatcg accccacgat tcgtattggt    3120
cagacaggta tgatgaacaa cctgttacag caactttccc aaagtcagtt aaatatcgat    3180
accgttgaag atagctttaa aaattatctg accgcatttg aagatgtcgc taacttgcag    3240
gtgattagcg gatatcatga cagtatcaat gtcaatgagg gactcactta tttaattggt    3300
tatagccaga cagaacccag aatatattat tggcgcaatg tcgatcacca aaagtgccag    3360
cacggtcaat ttgctgccaa tgcctgggga gaatggaaaa aaattgaaat acccatcaat    3420
gtatggcagg aaaatatcag acctgttatt tacaagtctc gtttgtattt actgtggctg    3480
gaacaaaaag agctgaaaaa tgaaagtgaa gatggcaaga tagatatcac tgattatata    3540
ttaaaactgt cacatattcg ttatgatggc agctggagct caccgtttaa ttttaatgtg    3600
actgataaaa tagaaaacct gatcaataaa aaagccagca ttggtatgta ttgttcttct    3660
gattatgaaa aagacgtcat tattgtttat ttccatgaga aaaagacaa ttattctttt    3720 aatagtcttc ctgcaagaga agggatgacc attaaccctg atatgacatt atccattctc    3780
acagaaaatg atttagacgc cattgttaag agcacattat cagaacttga taccaggaca    3840
gaatacaaag tcaacaatca atttgctaca gattatttgg ccgaatataa ggaatctata    3900
accacaaaaa ataaattagc cagttttacc ggaaatattt ttgatctctc gtatatatca    3960
ccaggaaatg gtcatattaa tttaacgttc aatccttcaa tggaaattaa tttttcaaaa    4020
ggcaatatat ataatgatga ggttaaatac ctgttatcga tggtagaaga tgaaacggtt    4080 atttatttg attatgatag acatgatgaa atgcttggaa agaagaaga agttttttcat    4140 tatggaactt tggattttat tatttccatc gatcttaaaa atgccgaata ttttagagtg    4200
ttaatgcatc taagaaccaa ggaaaaaatt cctagaaaat cagaaattgg agttggtata    4260
aattatgatt atgaatcaaa tgatgctgaa ttcaaacttg atactaacat agtattagat    4320
tggaaagata acacaggagt atggcatact atatgtgaat catttactaa tgatgtttca    4380
atcattaata acatgggaaa tattgcggca ctgttccttc gcgaggatcc atgtgtgtat    4440
ttatgttcaa tagccacaga tataaaaatt gcttcatcta tgatcgaaca gatccaagat    4500
aaaaacatta gttttttatt aaaaaatggc tctgatattc tagtggagtt aaatgctgaa    4560
gaccatgtgg catctaaacc ttcacacgaa tctgacccta tggtatatga ttttaatcaa    4620
gtaaaagttg atattgaagg ctatgatatt cctctggtga gcgagtttat tattaagcaa    4680
```

```
cccgacggcg gttataacga tattgttatt gaatcgccaa ttcatataaa actaaaatcc   4740
aaagatacaa gtaacgttat atcactgcat aaaatgccat caggcacaca atatatgcag   4800
attggccctt acagaacccg gttaaatact ttattttcca gaaaattagc tgaaagagcc   4860
aatattggta ttgataatgt tttaagtatg gaaacgcaaa atttaccaga gccgcaatta   4920
ggtgaagggt tttatgcgac atttaagttg ccccctaca ataaagagga gcatggtgat   4980
gaacgttggt ttaagatcca tattgggaat attgatggca attctgccag acaaccttat   5040
tacgaaggaa tgttatctga tattgaaacc acagtaacgc tctttgttcc ctatgctaaa   5100
ggatattaca tacgtgaagg tgtcagatta ggggttgggg acaaaaaaat tatctatgac   5160
aaatcctggg aatctgcttt cttttatttt gatgagacga aaatcaatt tatattcatt   5220 aatgatgccg atcatgattc gggaatgaca caacagggga tagtaaaaaa tatcaaaaaa   5280
tataaagggt ttattcatgt cgttgtcatg aaaaataaca ctgaacccat ggatttcaac   5340
ggcgccaatg caatctattt ctgggaattg ttctattaca cgcccatgat ggtattccag   5400
cgcttattgc aagagcagaa ttttaccgaa tcgacacgct ggctgcgcta tatctggaac   5460
ccggccggat attcggttca gggtgaaatg caggattatt actggaacgt ccgcccattg   5520
gaggaagata cgtcctggaa tgccaatccg ctggattcgg tcgatcctga cgccgttgcc   5580
cagcatgatc cgatgcacta taaagtggct acctttatga aaatgctgga tttgttgatt   5640
acccgcggag atagcgccta tcgccagctt gaacgtgata ccttaaacga agctaaaatg   5700
tggtatgtac aggcgctcac tttattgggt gatgagcctt attttcatt ggataacgat   5760 tggtcagagc cacggctgga agaagctgcc agccaaacaa tgcggcatca ttatcaacat   5820
aaaatgctgc aactgcgtca gcgcgctgca ttacccacga aacgtacggc aaattcgtta   5880
accgcattgt tcctccctca aattaataaa aaactgcaag gttactggca gacattgacg   5940
caacgcctct ataacttacg ccataacctg acaatcgacg tcagccact gtcattatct   6000 ctctatgcca cgcccgcaga tccgtccatg ttactcagtg ctgccatcac tgcttcacaa   6060
ggcggcggcg atttacctca tgcagtgatg ccgatgtacc gttttccggt gattctggaa   6120
aatgccaagt gggggtaag ccagttgata caatttggca ataccctgct cagcattact   6180
gaacggcagg atgcagaagc cttggctgaa atactgcaaa ctcaaggcag tgagttagcc   6240
ctgcaaagta ttaaaatgca ggataaggtc atggctgaaa ttgatgctga taaattggcg   6300
cttcaagaaa gccgtcatgg tgcacagtct cgttttgaca gtttcaatac gctgtacgac   6360
gaagatgtta acgctggtga aaaacaagcg atggatcttt acctctcttc atcggtcttg   6420
agcaccagcg gcacagccct gcatatggcc gccgcgcgg cagatctcgt ccccaatatt   6480
tacggttttg ctgtgggagg ttcccgtttt ggggcgcttt tcaatgccag tgcgattggt   6540
atcgaaattt ctgcgtcagc aacacgtatt gccgcagaca aaatcagcca atcagaaata   6600
taccgtcgcc gtcggcaaga gtgggaaatt cagcgcaata atgcgaaagc tgagataaaa   6660
caaattgatg ctcaattagc gacgctggct gtacgtcgtg aagcggcagt attacaaaaa   6720
aactatctgg aaactcagca ggcacaaact caggcgcagt tagcctttct gcaaagtaaa   6780
ttcagtaatg cagcgctata caactggctc cgtggaaggt tgtccgctat ttattatcag   6840
ttttatgatt tggcggtctc actctgttta atggcagagc aaacttatca gtatgaattg   6900
aataatgcgg cagcacactt tattaaacca ggtgcctggc atgggactta tgcgggttta   6960
ttagcgggtg aaaccctgat gctgaattta gcacagatgg aaaaaagcta tttgaaaaa   7020 gatgaacggg cactggaggt caccagaacc gtttctctgg ctgaagtgta tgctggtctg   7080
```

-continued

```
acagaaaata gtttcatttt aaagataaa gtgactgagt tagtcaatgc aggtgaaggc      7140
agtgcaggca caacgcttaa cggtttgaac gtcgaaggga cacaactgca agccagcctc      7200
aaattatcgg atctgaatat tgctaccgat tatcctgacg gtttaggtaa tacacgccgt      7260
atcaaacaaa tcagtgtgac attacctgcc cttttagggc cttatcagga tgttcgggca      7320
atactaagtt atggcggcag cacaatgatg ccacgtggct gcaaagcgat tgcgatctca      7380
catggcatga atgacagtgg tcaattccag atggatttca atgatgccaa gtacctgcca      7440
tttgaagggc ttcctgtggc cgatacaggc acattaaccc tcagttttcc cggtatcagt      7500
ggtaaacaga aaagcttatt gctcagcctg agcgatatca ttctgcatat ccgttacacc      7560
attcgttct                                                              7569
```

```
<210> SEQ ID NO 14
<211> LENGTH: 2523
<212> TYPE: PRT
<213> ORGANISM: Xenorhabdus nematophilus

<400> SEQUENCE: 14

Met Ile Lys Val Asn Glu Leu Leu Asp Lys Ile Asn Arg Lys Arg Ser
1               5                   10                  15

Gly Asp Thr Leu Leu Thr Asn Ile Ser Phe Met Ser Phe Ser Glu
            20                  25                  30

Phe Arg His Arg Thr Ser Gly Thr Leu Thr Trp Arg Glu Thr Asp Phe
        35                  40                  45

Leu Tyr Gln Gln Ala His Gln Glu Ser Lys Gln Asn Lys Leu Glu Glu
    50                  55                  60

Leu Arg Ile Leu Ser Arg Ala Asn Pro Gln Leu Ala Asn Thr Thr Asn
65                  70                  75                  80

Leu Asn Ile Thr Pro Ser Thr Leu Asn Asn Ser Tyr Asn Ser Trp Phe
                85                  90                  95

Tyr Gly Arg Ala His Arg Phe Val Lys Pro Gly Ser Ile Ala Ser Ile
            100                 105                 110

Phe Ser Pro Ala Ala Tyr Leu Thr Glu Leu Tyr Arg Glu Ala Lys Asp
        115                 120                 125

Phe His Pro Asp Asn Ser Gln Tyr His Leu Asn Lys Arg Arg Pro Asp
    130                 135                 140

Ile Ala Ser Leu Ala Leu Thr Gln Asn Asn Met Asp Glu Glu Ile Ser
145                 150                 155                 160

Thr Leu Ser Leu Ser Asn Glu Leu Leu Leu His Asn Ile Gln Thr Leu
                165                 170                 175

Glu Lys Thr Asp Tyr Asn Gly Val Met Lys Met Leu Ser Thr Tyr Arg
            180                 185                 190

Gln Thr Gly Met Thr Pro Tyr His Leu Pro Tyr Glu Ser Ala Arg Gln
        195                 200                 205

Ala Ile Leu Leu Gln Asp Lys Asn Leu Thr Ala Phe Ser Arg Asn Thr
    210                 215                 220

Asp Val Ala Glu Leu Met Asp Pro Thr Ser Leu Ala Ile Lys Thr
225                 230                 235                 240

Asp Ile Ser Pro Glu Leu Tyr Gln Ile Leu Val Glu Glu Ile Thr Pro
                245                 250                 255

Glu Asn Ser Thr Glu Leu Met Lys Lys Asn Phe Gly Thr Asp Asp Val
            260                 265                 270

Leu Ile Phe Lys Ser Tyr Ala Ser Leu Ala Arg Tyr Tyr Asp Leu Ser
```

-continued

```
              275                 280                 285
Tyr Asp Glu Leu Ser Leu Phe Val Asn Leu Ser Phe Gly Lys Lys Asn
290                 295                 300

Thr Asn Gln Gln Tyr Lys Asn Glu Gln Leu Ile Thr Leu Val Asn Asp
305                 310                 315                 320

Gly Asn Asp Thr Ala Thr Ala Arg Leu Ile Lys Arg Thr Arg Lys Asp
                325                 330                 335

Phe Tyr Asp Ser His Leu Asn Tyr Ala Glu Leu Ile Pro Ile Lys Glu
                340                 345                 350

Asn Glu Tyr Lys Tyr Asn Phe Ser Val Lys Lys Thr Glu Pro Asp His
                355                 360                 365

Leu Asp Phe Arg Leu Gln Asn Gly Asp Lys Glu Tyr Ile Tyr Gln Asp
370                 375                 380

Lys Asn Phe Val Pro Ile Ala Asn Thr His Tyr Ser Ile Pro Ile Lys
385                 390                 395                 400

Leu Thr Thr Glu Gln Ile Thr Asn Gly Ile Thr Leu Arg Leu Trp Arg
                405                 410                 415

Val Lys Pro Asn Pro Ser Asp Ala Ile Asn Ala Asn Ala Tyr Phe Lys
                420                 425                 430

Met Met Glu Phe Pro Gly Asp Ile Phe Leu Leu Lys Leu Asn Lys Ala
                435                 440                 445

Ile Arg Leu Tyr Lys Ala Thr Gly Ile Ser Pro Glu Asp Ile Trp Gln
                450                 455                 460

Val Ile Glu Ser Ile Tyr Asp Asp Leu Thr Ile Asp Ser Asn Val Leu
465                 470                 475                 480

Gly Lys Leu Phe Tyr Val Gln Tyr Tyr Met Gln His Tyr Asn Ile Ser
                485                 490                 495

Val Ser Asp Ala Leu Val Leu Cys His Ser Asp Ile Ser Gln Tyr Ser
                500                 505                 510

Thr Lys Gln Gln Pro Ser His Phe Thr Ile Leu Phe Asn Thr Pro Leu
                515                 520                 525

Leu Asn Gly Gln Glu Phe Ser Ala Asp Asn Thr Lys Leu Asp Leu Thr
530                 535                 540

Pro Gly Glu Ser Lys Asn His Phe Tyr Leu Gly Ile Met Lys Arg Ala
545                 550                 555                 560

Phe Arg Val Asn Asp Thr Glu Leu Tyr Thr Leu Trp Lys Leu Ala Asn
                565                 570                 575

Gly Gly Thr Asn Pro Glu Phe Met Cys Ser Ile Glu Asn Leu Ser Leu
                580                 585                 590

Leu Tyr Arg Val Arg Leu Leu Ala Asp Ile His His Leu Thr Val Asn
                595                 600                 605

Glu Leu Ser Met Leu Leu Ser Val Ser Pro Tyr Val Asn Thr Lys Ile
610                 615                 620

Ala Leu Phe Ser Asp Thr Ala Leu Thr Gln Leu Ile Ser Phe Leu Phe
625                 630                 635                 640

Gln Cys Thr Gln Trp Leu Thr Thr Gln Lys Trp Ser Val Ser Asp Val
                645                 650                 655

Phe Leu Met Thr Thr Asp Asn Tyr Ser Thr Val Leu Thr Pro Asp Ile
                660                 665                 670

Glu Asn Leu Ile Thr Thr Leu Ser Asn Gly Leu Ser Thr Leu Ser Leu
                675                 680                 685

Gly Asp Asp Glu Leu Ile Arg Ala Ala Pro Leu Ile Ala Ala Ser
690                 695                 700
```

```
Ile Gln Met Asp Ser Ala Lys Thr Ala Glu Thr Ile Leu Leu Trp Ile
705                 710                 715                 720

Asn Gln Ile Lys Pro Gln Gly Leu Thr Phe Asp Asp Phe Met Ile Ile
                725                 730                 735

Ala Ala Asn Arg Asp Arg Ser Glu Asn Glu Thr Ser Asn Met Val Ala
                740                 745                 750

Phe Cys Gln Val Leu Gly Gln Leu Ser Leu Ile Val Arg Asn Ile Gly
                755                 760                 765

Leu Ser Glu Asn Glu Leu Thr Leu Leu Val Thr Lys Pro Glu Lys Phe
770                 775                 780

Gln Ser Glu Thr Thr Ala Leu Gln His Asp Leu Pro Thr Leu Gln Ala
785                 790                 795                 800

Leu Thr Arg Phe His Ala Val Ile Met Arg Cys Gly Ser Tyr Ala Thr
                805                 810                 815

Glu Ile Leu Thr Ala Leu Glu Leu Gly Ala Leu Thr Ala Glu Gln Leu
                820                 825                 830

Ala Val Ala Leu Lys Phe Asp Ala Gln Val Val Thr Gln Ala Leu Gln
                835                 840                 845

Gln Thr Gly Leu Gly Val Asn Thr Phe Thr Asn Trp Arg Thr Ile Asp
850                 855                 860

Val Thr Leu Gln Trp Leu Asp Val Ala Ala Thr Leu Gly Ile Thr Pro
865                 870                 875                 880

Asp Gly Val Ala Ala Leu Ile Lys Leu Lys Tyr Ile Gly Glu Pro Glu
                885                 890                 895

Thr Pro Met Pro Thr Phe Asp Asp Trp Gln Ala Ala Ser Thr Leu Leu
                900                 905                 910

Gln Ala Gly Leu Asn Ser Gln Ser Asp Gln Leu Gln Ala Trp Leu
                915                 920                 925

Asp Glu Ala Thr Thr Thr Ala Ala Ser Ala Tyr Tyr Ile Lys Asn Ser
930                 935                 940

Ala Pro Gln Gln Ile Lys Ser Arg Asp Glu Leu Tyr Ser Tyr Leu Leu
945                 950                 955                 960

Ile Asp Asn Gln Val Ser Ala Gln Val Lys Thr Thr Arg Val Ala Glu
                965                 970                 975

Ala Ile Ala Ser Ile Gln Leu Tyr Val Asn Arg Ala Leu Asn Asn Val
                980                 985                 990

Glu Gly Lys Val Ser Lys Pro Val  Lys Thr Arg Gln Phe  Phe Cys Asp
                995                 1000                1005

Trp Glu  Thr Tyr Asn Arg Arg  Tyr Ser Thr Trp Ala  Gly Val Ser
    1010                1015                1020

Glu Leu  Ala Tyr Tyr Pro Glu  Asn Tyr Ile Asp Pro  Thr Ile Arg
    1025                1030                1035

Ile Gly  Gln Thr Gly Met Met  Asn Asn Leu Leu Gln  Gln Leu Ser
    1040                1045                1050

Gln Ser  Gln Leu Asn Ile Asp  Thr Val Glu Asp Ser  Phe Lys Asn
    1055                1060                1065

Tyr Leu  Thr Ala Phe Glu Asp  Val Ala Asn Leu Gln  Val Ile Ser
    1070                1075                1080

Gly Tyr  His Asp Ser Ile Asn  Val Asn Glu Gly Leu  Thr Tyr Leu
    1085                1090                1095

Ile Gly  Tyr Ser Gln Thr Glu  Pro Arg Ile Tyr Tyr  Trp Arg Asn
    1100                1105                1110
```

-continued

```
Val Asp His Gln Lys Cys Gln His Gly Gln Phe Ala Ala Asn Ala
1115                1120                1125

Trp Gly Glu Trp Lys Lys Ile Glu Ile Pro Ile Asn Val Trp Gln
1130                1135                1140

Glu Asn Ile Arg Pro Val Ile Tyr Lys Ser Arg Leu Tyr Leu Leu
1145                1150                1155

Trp Leu Glu Gln Lys Glu Leu Lys Asn Glu Ser Glu Asp Gly Lys
1160                1165                1170

Ile Asp Ile Thr Asp Tyr Ile Leu Lys Leu Ser His Ile Arg Tyr
1175                1180                1185

Asp Gly Ser Trp Ser Ser Pro Phe Asn Phe Asn Val Thr Asp Lys
1190                1195                1200

Ile Glu Asn Leu Ile Asn Lys Lys Ala Ser Ile Gly Met Tyr Cys
1205                1210                1215

Ser Ser Asp Tyr Glu Lys Asp Val Ile Ile Val Tyr Phe His Glu
1220                1225                1230

Lys Lys Asp Asn Tyr Ser Phe Asn Ser Leu Pro Ala Arg Glu Gly
1235                1240                1245

Met Thr Ile Asn Pro Asp Met Thr Leu Ser Ile Leu Thr Glu Asn
1250                1255                1260

Asp Leu Asp Ala Ile Val Lys Ser Thr Leu Ser Glu Leu Asp Thr
1265                1270                1275

Arg Thr Glu Tyr Lys Val Asn Asn Gln Phe Ala Thr Asp Tyr Leu
1280                1285                1290

Ala Glu Tyr Lys Glu Ser Ile Thr Thr Lys Asn Lys Leu Ala Ser
1295                1300                1305

Phe Thr Gly Asn Ile Phe Asp Leu Ser Tyr Ile Ser Pro Gly Asn
1310                1315                1320

Gly His Ile Asn Leu Thr Phe Asn Pro Ser Met Glu Ile Asn Phe
1325                1330                1335

Ser Lys Gly Asn Ile Tyr Asn Asp Glu Val Lys Tyr Leu Leu Ser
1340                1345                1350

Met Val Glu Asp Glu Thr Val Ile Leu Phe Asp Tyr Asp Arg His
1355                1360                1365

Asp Glu Met Leu Gly Lys Glu Glu Val Phe His Tyr Gly Thr
1370                1375                1380

Leu Asp Phe Ile Ile Ser Ile Asp Leu Lys Asn Ala Glu Tyr Phe
1385                1390                1395

Arg Val Leu Met His Leu Arg Thr Lys Glu Lys Ile Pro Arg Lys
1400                1405                1410

Ser Glu Ile Gly Val Gly Ile Asn Tyr Asp Tyr Glu Ser Asn Asp
1415                1420                1425

Ala Glu Phe Lys Leu Asp Thr Asn Ile Val Leu Asp Trp Lys Asp
1430                1435                1440

Asn Thr Gly Val Trp His Thr Ile Cys Glu Ser Phe Thr Asn Asp
1445                1450                1455

Val Ser Ile Ile Asn Asn Met Gly Asn Ile Ala Ala Leu Phe Leu
1460                1465                1470

Arg Glu Asp Pro Cys Val Tyr Leu Cys Ser Ile Ala Thr Asp Ile
1475                1480                1485

Lys Ile Ala Ser Ser Met Ile Glu Gln Ile Gln Asp Lys Asn Ile
1490                1495                1500

Ser Phe Leu Leu Lys Asn Gly Ser Asp Ile Leu Val Glu Leu Asn
```

-continued

```
           1505                1510                1515

Ala Glu Asp His Val Ala Ser Lys Pro Ser His Glu Ser Asp Pro
    1520                1525                1530

Met Val Tyr Asp Phe Asn Gln Val Lys Val Asp Ile Glu Gly Tyr
    1535                1540                1545

Asp Ile Pro Leu Val Ser Glu Phe Ile Ile Lys Gln Pro Asp Gly
    1550                1555                1560

Gly Tyr Asn Asp Ile Val Ile Glu Ser Pro Ile His Ile Lys Leu
    1565                1570                1575

Lys Ser Lys Asp Thr Ser Asn Val Ile Ser Leu His Lys Met Pro
    1580                1585                1590

Ser Gly Thr Gln Tyr Met Gln Ile Gly Pro Tyr Arg Thr Arg Leu
    1595                1600                1605

Asn Thr Leu Phe Ser Arg Lys Leu Ala Glu Arg Ala Asn Ile Gly
    1610                1615                1620

Ile Asp Asn Val Leu Ser Met Glu Thr Gln Asn Leu Pro Glu Pro
    1625                1630                1635

Gln Leu Gly Glu Gly Phe Tyr Ala Thr Phe Lys Leu Pro Pro Tyr
    1640                1645                1650

Asn Lys Glu Glu His Gly Asp Glu Arg Trp Phe Lys Ile His Ile
    1655                1660                1665

Gly Asn Ile Asp Gly Asn Ser Ala Arg Gln Pro Tyr Tyr Glu Gly
    1670                1675                1680

Met Leu Ser Asp Ile Glu Thr Thr Val Thr Leu Phe Val Pro Tyr
    1685                1690                1695

Ala Lys Gly Tyr Tyr Ile Arg Glu Gly Val Arg Leu Gly Val Gly
    1700                1705                1710

Tyr Lys Lys Ile Ile Tyr Asp Lys Ser Trp Glu Ser Ala Phe Phe
    1715                1720                1725

Tyr Phe Asp Glu Thr Lys Asn Gln Phe Ile Phe Ile Asn Asp Ala
    1730                1735                1740

Asp His Asp Ser Gly Met Thr Gln Gln Gly Ile Val Lys Asn Ile
    1745                1750                1755

Lys Lys Tyr Lys Gly Phe Ile His Val Val Met Lys Asn Asn
    1760                1765                1770

Thr Glu Pro Met Asp Phe Asn Gly Ala Asn Ala Ile Tyr Phe Trp
    1775                1780                1785

Glu Leu Phe Tyr Tyr Thr Pro Met Met Val Phe Gln Arg Leu Leu
    1790                1795                1800

Gln Glu Gln Asn Phe Thr Glu Ser Thr Arg Trp Leu Arg Tyr Ile
    1805                1810                1815

Trp Asn Pro Ala Gly Tyr Ser Val Gln Gly Glu Met Gln Asp Tyr
    1820                1825                1830

Tyr Trp Asn Val Arg Pro Leu Glu Glu Asp Thr Ser Trp Asn Ala
    1835                1840                1845

Asn Pro Leu Asp Ser Val Asp Pro Asp Ala Val Ala Gln His Asp
    1850                1855                1860

Pro Met His Tyr Lys Val Ala Thr Phe Met Lys Met Leu Asp Leu
    1865                1870                1875

Leu Ile Thr Arg Gly Asp Ser Ala Tyr Arg Gln Leu Glu Arg Asp
    1880                1885                1890

Thr Leu Asn Glu Ala Lys Met Trp Tyr Val Gln Ala Leu Thr Leu
    1895                1900                1905
```

-continued

Leu Gly Asp Glu Pro Tyr Phe Ser Leu Asp Asn Asp Trp Ser Glu
1910                1915                1920

Pro Arg Leu Glu Glu Ala Ala Ser Gln Thr Met Arg His His Tyr
    1925            1930                1935

Gln His Lys Met Leu Gln Leu Arg Gln Arg Ala Ala Leu Pro Thr
    1940            1945                1950

Lys Arg Thr Ala Asn Ser Leu Thr Ala Leu Phe Leu Pro Gln Ile
    1955            1960                1965

Asn Lys Lys Leu Gln Gly Tyr Trp Gln Thr Leu Thr Gln Arg Leu
    1970            1975                1980

Tyr Asn Leu Arg His Asn Leu Thr Ile Asp Gly Gln Pro Leu Ser
    1985            1990                1995

Leu Ser Leu Tyr Ala Thr Pro Ala Asp Pro Ser Met Leu Leu Ser
    2000            2005                2010

Ala Ala Ile Thr Ala Ser Gln Gly Gly Gly Asp Leu Pro His Ala
    2015            2020                2025

Val Met Pro Met Tyr Arg Phe Pro Val Ile Leu Glu Asn Ala Lys
    2030            2035                2040

Trp Gly Val Ser Gln Leu Ile Gln Phe Gly Asn Thr Leu Leu Ser
    2045            2050                2055

Ile Thr Glu Arg Gln Asp Ala Glu Ala Leu Ala Glu Ile Leu Gln
    2060            2065                2070

Thr Gln Gly Ser Glu Leu Ala Leu Gln Ser Ile Lys Met Gln Asp
    2075            2080                2085

Lys Val Met Ala Glu Ile Asp Ala Asp Lys Leu Ala Leu Gln Glu
    2090            2095                2100

Ser Arg His Gly Ala Gln Ser Arg Phe Asp Ser Phe Asn Thr Leu
    2105            2110                2115

Tyr Asp Glu Asp Val Asn Ala Gly Glu Lys Gln Ala Met Asp Leu
    2120            2125                2130

Tyr Leu Ser Ser Ser Val Leu Ser Thr Ser Gly Thr Ala Leu His
    2135            2140                2145

Met Ala Ala Ala Ala Ala Asp Leu Val Pro Asn Ile Tyr Gly Phe
    2150            2155                2160

Ala Val Gly Gly Ser Arg Phe Gly Ala Leu Phe Asn Ala Ser Ala
    2165            2170                2175

Ile Gly Ile Glu Ile Ser Ala Ser Ala Thr Arg Ile Ala Ala Asp
    2180            2185                2190

Lys Ile Ser Gln Ser Glu Ile Tyr Arg Arg Arg Gln Glu Trp
    2195            2200                2205

Glu Ile Gln Arg Asn Asn Ala Glu Ala Glu Ile Lys Gln Ile Asp
    2210            2215                2220

Ala Gln Leu Ala Thr Leu Ala Val Arg Arg Glu Ala Ala Val Leu
    2225            2230                2235

Gln Lys Asn Tyr Leu Glu Thr Gln Gln Ala Gln Thr Gln Ala Gln
    2240            2245                2250

Leu Ala Phe Leu Gln Ser Lys Phe Ser Asn Ala Ala Leu Tyr Asn
    2255            2260                2265

Trp Leu Arg Gly Arg Leu Ser Ala Ile Tyr Tyr Gln Phe Tyr Asp
    2270            2275                2280

Leu Ala Val Ser Leu Cys Leu Met Ala Glu Gln Thr Tyr Gln Tyr
    2285            2290                2295

-continued

| | | | | | | | | | | | |
|---|---|---|---|---|---|---|---|---|---|---|---|
| Glu | Leu | Asn | Asn | Ala | Ala | Ala | His | Phe | Ile | Lys | Pro | Gly | Ala | Trp |
| | 2300 | | | | 2305 | | | | 2310 | | |
| His | Gly | Thr | Tyr | Ala | Gly | Leu | Leu | Ala | Gly | Glu | Thr | Leu | Met | Leu |
| 2315 | | | | | 2320 | | | | | 2325 | | |
| Asn | Leu | Ala | Gln | Met | Glu | Lys | Ser | Tyr | Leu | Glu | Lys | Asp | Glu | Arg |
| 2330 | | | | | 2335 | | | | | 2340 | | |
| Ala | Leu | Glu | Val | Thr | Arg | Thr | Val | Ser | Leu | Ala | Glu | Val | Tyr | Ala |
| 2345 | | | | | 2350 | | | | | 2355 | | |
| Gly | Leu | Thr | Glu | Asn | Ser | Phe | Ile | Leu | Lys | Asp | Lys | Val | Thr | Glu |
| | 2360 | | | | | 2365 | | | | | 2370 | | |
| Leu | Val | Asn | Ala | Gly | Glu | Gly | Ser | Ala | Gly | Thr | Thr | Leu | Asn | Gly |
| | 2375 | | | | | 2380 | | | | | 2385 | | |
| Leu | Asn | Val | Glu | Gly | Thr | Gln | Leu | Gln | Ala | Ser | Leu | Lys | Leu | Ser |
| | 2390 | | | | | 2395 | | | | | 2400 | | |
| Asp | Leu | Asn | Ile | Ala | Thr | Asp | Tyr | Pro | Asp | Gly | Leu | Gly | Asn | Thr |
| | 2405 | | | | | 2410 | | | | | 2415 | | |
| Arg | Arg | Ile | Lys | Gln | Ile | Ser | Val | Thr | Leu | Pro | Ala | Leu | Leu | Gly |
| | 2420 | | | | | 2425 | | | | | 2430 | | |
| Pro | Tyr | Gln | Asp | Val | Arg | Ala | Ile | Leu | Ser | Tyr | Gly | Gly | Ser | Thr |
| | 2435 | | | | | 2440 | | | | | 2445 | | |
| Met | Met | Pro | Arg | Gly | Cys | Lys | Ala | Ile | Ala | Ile | Ser | His | Gly | Met |
| | 2450 | | | | | 2455 | | | | | 2460 | | |
| Asn | Asp | Ser | Gly | Gln | Phe | Gln | Met | Asp | Phe | Asn | Asp | Ala | Lys | Tyr |
| | 2465 | | | | | 2470 | | | | | 2475 | | |
| Leu | Pro | Phe | Glu | Gly | Leu | Pro | Val | Ala | Asp | Thr | Gly | Thr | Leu | Thr |
| | 2480 | | | | | 2485 | | | | | 2490 | | |
| Leu | Ser | Phe | Pro | Gly | Ile | Ser | Gly | Lys | Gln | Lys | Ser | Leu | Leu | Leu |
| | 2495 | | | | | 2500 | | | | | 2505 | | |
| Ser | Leu | Ser | Asp | Ile | Ile | Leu | His | Ile | Arg | Tyr | Thr | Ile | Arg | Ser |
| | 2510 | | | | | 2515 | | | | | 2520 | | |

<210> SEQ ID NO 15
<211> LENGTH: 3048
<212> TYPE: DNA
<213> ORGANISM: Xenorhabdus nematophilus

<400> SEQUENCE: 15

| | |
|---|---|
| atgaagaatt tcgttcacag caatacgcca tccgtcaccg tactggacaa ccgtggtcag | 60 |
| acagtacgcg aaatagcctg gtatcggcac cccgatacac tcaggtaac cgatgaacgc | 120 |
| atcaccggtt atcaatatga tgctcaagga tctctgactc agagtattga tccgcgattt | 180 |
| tatgaacgcc agcagacagc gagtgacaag aacgccatta cacccaatct tattctcttg | 240 |
| tcatcactca gtaagaaggc attgcgtacg caaagtgtgg atgccggaac ccgtgtcgcc | 300 |
| ctgcatgatg ttgccgggcg tcccgttta gctgtcagcg ccaatggcgt tagccgaacg | 360 |
| tttcagtatg aaagtgataa ccttccggga cgattgctaa cgattaccga gcaggtaaaa | 420 |
| ggagagaacg cctgtatcac ggagcgattg atctggtcag gaaatacgcc ggcagaaaaa | 480 |
| ggcaataatc tggccggcca gtgcgtggtc cattatgatc ccaccggaat gaatcaaacc | 540 |
| aacagcatat cgttaaccag cataccctg tccatcacac agcaattact gaaagatgac | 600 |
| agcgaagccg attggcacgg tatggatgaa tctggctgga aaaacgcgct ggcgccggaa | 660 |
| agcttcactt ctgtcagcac aacgatgct accggcacgg tattaacgag tacagatgct | 720 |
| gccggaaaca agcaacgtat cgcctatgat gtggccggtc tgcttcaagg cagttggttg | 780 |

-continued

```
gcgctgaagg ggaaacaaga acaagttatc gtgaaatccc tgacctattc ggctgccagc      840
cagaagctac gggaggaaca tggtaacggg atagtgacta catataccta tgaacccgag      900
acgcaacgag ttattggcat aaaaacagaa cgtccttccg gtcatgccgc tgggagaaa       960 attttacaaa acctgcgtta tgaatatgat cctgtcggaa atgtgctgaa atcaactaat     1020
gatgctgaaa ttacccgctt ttggcgcaac cagaaaattg taccggaaaa tacttacacc     1080
tatgacagcc tgtaccagct ggtttccgtc actgggcgtg aaatggcgaa tattggccga     1140
caaaaaaacc agttacccat ccccgctctg attgataaca atacttatac gaattactct     1200
cgcacttacg actatgatcg tgggggaaat ctgaccagaa ttcgccataa ttcaccgatc     1260
accggtaata actatacaac gaacatgacc gtttcagatc acagcaaccg ggctgtactg     1320
gaagagctgg cgcaagatcc cactcaggtg gatatgttgt tcaccccgg cgggcatcag      1380 acccggcttg ttcccggtca ggatcttttc tggacacccc gtgacgaatt gcaacaagtg     1440
atattggtca atagggaaaa tacgacgcct gatcaggaat tctaccgtta tgatgcagac     1500
agtcagcgtg tcattaagac tcatattcag aagacaggta acagtgagca aatacagcga     1560
acattatatt tgccagagct ggaatggcgc acgacatata gcggcaatac attaaaagag     1620
tttttgcagg tcatcactgt cggtgaatcg ggtcaggcac aagtgcgggt gctgcattgg     1680
gaaacaggca aaccggcgga tatcagcaat gatcagctgc gctacagtta tggcaacctg     1740
attggcagta gcgggctgga attggacagt gacgggcaga tcattagtca ggaagaatat     1800 taccccctatg ggggaaccgc cgtgtgggca gcccgaagtc agtcagaagc tgattacaaa     1860
accgtgcgtt attctggcaa agagcgggat gcaacagggt tgtattacta cggttatcgt     1920
tattatcaat cgtggacagg gcgatggttg agtgtagatc ctgccggtga ggtcgatggt     1980
ctcaatttgt tccgaatgtg caggaataac cccatcgttt tttctgattc tgatggtcgt     2040
ttccccggtc agggtgtcct tgcctggata gggaaaaaag cgtatcgaaa ggcagtcaac     2100
atcacgacag aacacctgct tgaacaaggc gcttcctttg atacgttctt gaaattaaac     2160
cgaggattgc gaacgtttgt tttggtgtg ggggtagcaa gtctgggggt gaaggcggcc      2220
acgattgcag gagcgtcgcc ttgggggatt gtcgggctg ccattggtgg ttttgtctcc      2280
ggggcggtga tggggttttt cgcgaacaac atctcagaaa aaattgggga agttttaagt     2340
tatctgacgc gtaaacgttc tgttcctgtt caggttggcg cttttgttgt cacatcgctt     2400
gtgacgtctg cactatttaa cagctcttcg acaggtaccg ccatttccgc agcaacagcg     2460
gtcaccgttg gaggattaat ggctttagcc ggagagcata acacgggcat ggctatcagt     2520
attgccacac ccgccggaca aggtacgctc gatacgctca ggcccggtaa tgtcagcgcg     2580
ccagagcggt taggggcact atcaggcgca attattggcg gcatattact tggccgccat     2640
cagggaagtt ctgagctggg tgaacgggca gcgattggtg ctatgtatgg tgctcgatgg     2700
ggaaggatca ttggtaatct atgggatggc ccttatcggt ttatcggcag gttactgctc     2760
agaagaggca ttagctctgc catttccac gctgtcagtt ccaggagctg gtttggccga      2820
atgataggag aaagtgtcgg gagaaatatt tctgaagtat tattaccttla tagccgtaca    2880 cccggtgaat gggttggtgc agccattggc gggacagccg cggccgctca tcatgccgtt    2940
ggaggggaag ttgccaatgc cgctagccgg gttacctgga gcggctttaa gcgggcttt     3000 aataacttct tcttaacgc ctctgcacgt cataatgaat ccgaagca                   3048
```

<210> SEQ ID NO 16
<211> LENGTH: 1016

```
<212> TYPE: PRT
<213> ORGANISM: Xenorhabdus nematophilus

<400> SEQUENCE: 16

Met Lys Asn Phe Val His Ser Asn Thr Pro Ser Val Thr Val Leu Asp
1               5                   10                  15

Asn Arg Gly Gln Thr Val Arg Glu Ile Ala Trp Tyr Arg His Pro Asp
            20                  25                  30

Thr Pro Gln Val Thr Asp Glu Arg Ile Thr Gly Tyr Gln Tyr Asp Ala
        35                  40                  45

Gln Gly Ser Leu Thr Gln Ser Ile Asp Pro Arg Phe Tyr Glu Arg Gln
    50                  55                  60

Gln Thr Ala Ser Asp Lys Asn Ala Ile Thr Pro Asn Leu Ile Leu Leu
65                  70                  75                  80

Ser Ser Leu Ser Lys Lys Ala Leu Arg Thr Gln Ser Val Asp Ala Gly
                85                  90                  95

Thr Arg Val Ala Leu His Asp Val Ala Gly Arg Pro Val Leu Ala Val
            100                 105                 110

Ser Ala Asn Gly Val Ser Arg Thr Phe Gln Tyr Glu Ser Asp Asn Leu
        115                 120                 125

Pro Gly Arg Leu Leu Thr Ile Thr Glu Gln Val Lys Gly Glu Asn Ala
    130                 135                 140

Cys Ile Thr Glu Arg Leu Ile Trp Ser Gly Asn Thr Pro Ala Glu Lys
145                 150                 155                 160

Gly Asn Asn Leu Ala Gly Gln Cys Val Val His Tyr Asp Pro Thr Gly
                165                 170                 175

Met Asn Gln Thr Asn Ser Ile Ser Leu Thr Ser Ile Pro Leu Ser Ile
            180                 185                 190

Thr Gln Gln Leu Leu Lys Asp Asp Ser Glu Ala Asp Trp His Gly Met
        195                 200                 205

Asp Glu Ser Gly Trp Lys Asn Ala Leu Ala Pro Glu Ser Phe Thr Ser
    210                 215                 220

Val Ser Thr Thr Asp Ala Thr Gly Thr Val Leu Thr Ser Thr Asp Ala
225                 230                 235                 240

Ala Gly Asn Lys Gln Arg Ile Ala Tyr Asp Val Ala Gly Leu Leu Gln
                245                 250                 255

Gly Ser Trp Leu Ala Leu Lys Gly Lys Gln Glu Gln Val Ile Val Lys
            260                 265                 270

Ser Leu Thr Tyr Ser Ala Ala Ser Gln Lys Leu Arg Glu Glu His Gly
        275                 280                 285

Asn Gly Ile Val Thr Thr Tyr Thr Tyr Glu Pro Glu Thr Gln Arg Val
    290                 295                 300

Ile Gly Ile Lys Thr Glu Arg Pro Ser Gly His Ala Ala Gly Glu Lys
305                 310                 315                 320

Ile Leu Gln Asn Leu Arg Tyr Glu Tyr Asp Pro Val Gly Asn Val Leu
                325                 330                 335

Lys Ser Thr Asn Asp Ala Glu Ile Thr Arg Phe Trp Arg Asn Gln Lys
            340                 345                 350

Ile Val Pro Glu Asn Thr Tyr Thr Tyr Asp Ser Leu Tyr Gln Leu Val
        355                 360                 365

Ser Val Thr Gly Arg Glu Met Ala Asn Ile Gly Arg Gln Lys Asn Gln
    370                 375                 380

Leu Pro Ile Pro Ala Leu Ile Asp Asn Asn Thr Tyr Thr Asn Tyr Ser
385                 390                 395                 400
```

```
Arg Thr Tyr Asp Tyr Asp Arg Gly Gly Asn Leu Thr Arg Ile Arg His
            405                 410                 415
Asn Ser Pro Ile Thr Gly Asn Asn Tyr Thr Thr Asn Met Thr Val Ser
            420                 425                 430
Asp His Ser Asn Arg Ala Val Leu Glu Glu Leu Ala Gln Asp Pro Thr
            435                 440                 445
Gln Val Asp Met Leu Phe Thr Pro Gly Gly His Gln Thr Arg Leu Val
450                 455                 460
Pro Gly Gln Asp Leu Phe Trp Thr Pro Arg Asp Glu Leu Gln Gln Val
465                 470                 475                 480
Ile Leu Val Asn Arg Glu Asn Thr Thr Pro Asp Gln Glu Phe Tyr Arg
            485                 490                 495
Tyr Asp Ala Asp Ser Gln Arg Val Ile Lys Thr His Ile Gln Lys Thr
            500                 505                 510
Gly Asn Ser Glu Gln Ile Gln Arg Thr Leu Tyr Leu Pro Glu Leu Glu
            515                 520                 525
Trp Arg Thr Thr Tyr Ser Gly Asn Thr Leu Lys Glu Phe Leu Gln Val
            530                 535                 540
Ile Thr Val Gly Glu Ser Gly Gln Ala Gln Val Arg Val Leu His Trp
545                 550                 555                 560
Glu Thr Gly Lys Pro Ala Asp Ile Ser Asn Asp Gln Leu Arg Tyr Ser
            565                 570                 575
Tyr Gly Asn Leu Ile Gly Ser Ser Gly Leu Glu Leu Asp Ser Asp Gly
            580                 585                 590
Gln Ile Ile Ser Gln Glu Glu Tyr Tyr Pro Tyr Gly Gly Thr Ala Val
            595                 600                 605
Trp Ala Ala Arg Ser Gln Ser Glu Ala Asp Tyr Lys Thr Val Arg Tyr
            610                 615                 620
Ser Gly Lys Glu Arg Asp Ala Thr Gly Leu Tyr Tyr Tyr Gly Tyr Arg
625                 630                 635                 640
Tyr Tyr Gln Ser Trp Thr Gly Arg Trp Leu Ser Val Asp Pro Ala Gly
            645                 650                 655
Glu Val Asp Gly Leu Asn Leu Phe Arg Met Cys Arg Asn Asn Pro Ile
            660                 665                 670
Val Phe Ser Asp Ser Asp Gly Arg Phe Pro Gly Gln Gly Val Leu Ala
            675                 680                 685
Trp Ile Gly Lys Lys Ala Tyr Arg Lys Ala Val Asn Ile Thr Thr Glu
            690                 695                 700
His Leu Leu Glu Gln Gly Ala Ser Phe Asp Thr Phe Leu Lys Leu Asn
705                 710                 715                 720
Arg Gly Leu Arg Thr Phe Val Leu Gly Val Gly Val Ala Ser Leu Gly
            725                 730                 735
Val Lys Ala Ala Thr Ile Ala Gly Ala Ser Pro Trp Gly Ile Val Gly
            740                 745                 750
Ala Ala Ile Gly Gly Phe Val Ser Gly Ala Val Met Gly Phe Phe Ala
            755                 760                 765
Asn Asn Ile Ser Glu Lys Ile Gly Glu Val Leu Ser Tyr Leu Thr Arg
            770                 775                 780
Lys Arg Ser Val Pro Gln Val Gly Ala Phe Val Val Thr Ser Leu
785                 790                 795                 800
Val Thr Ser Ala Leu Phe Asn Ser Ser Ser Thr Gly Thr Ala Ile Ser
            805                 810                 815
```

-continued

Ala Ala Thr Ala Val Thr Val Gly Gly Leu Met Ala Leu Ala Gly Glu
            820                 825                 830

His Asn Thr Gly Met Ala Ile Ser Ile Ala Thr Pro Ala Gly Gln Gly
        835                 840                 845

Thr Leu Asp Thr Leu Arg Pro Gly Asn Val Ser Ala Pro Glu Arg Leu
    850                 855                 860

Gly Ala Leu Ser Gly Ala Ile Ile Gly Gly Ile Leu Leu Gly Arg His
865                 870                 875                 880

Gln Gly Ser Ser Glu Leu Gly Glu Arg Ala Ala Ile Gly Ala Met Tyr
                885                 890                 895

Gly Ala Arg Trp Gly Arg Ile Ile Gly Asn Leu Trp Asp Gly Pro Tyr
            900                 905                 910

Arg Phe Ile Gly Arg Leu Leu Leu Arg Arg Gly Ile Ser Ser Ala Ile
        915                 920                 925

Ser His Ala Val Ser Ser Arg Ser Trp Phe Gly Arg Met Ile Gly Glu
    930                 935                 940

Ser Val Gly Arg Asn Ile Ser Glu Val Leu Leu Pro Tyr Ser Arg Thr
945                 950                 955                 960

Pro Gly Glu Trp Val Gly Ala Ala Ile Gly Gly Thr Ala Ala Ala Ala
                965                 970                 975

His His Ala Val Gly Gly Glu Val Ala Asn Ala Ser Arg Val Thr
            980                 985                 990

Trp Ser Gly Phe Lys Arg Ala Phe Asn Asn Phe Phe Phe Asn Ala Ser
        995                 1000                1005

Ala Arg His Asn Glu Ser Glu Ala
    1010                1015

<210> SEQ ID NO 17
<211> LENGTH: 4479
<212> TYPE: DNA
<213> ORGANISM: Xenorhabdus nematophilus

<400> SEQUENCE: 17
atgcagggtt caacaccttt gaaacttgaa ataccgtcat tgccctctgg gggcggatca        60
ctaaaaggaa tgggagaagc actcaatgcc gtcggagcgg aagggggagc gtcattttca       120
ctgcccttgc cgatctctgt cgggcgtggt ctggtgccgg tgctatcact gaattacagc       180
agtactgccg gcaatgggtc attcgggatg ggtggcaat gtggggttgg ttttatcagc        240
ctgcgtaccg ccaagggcgt tccgcactat acgggacaag atgagtatct cgggccggat       300
ggggaagtgt tgagtattgt gccggacagc caagggcaac cagagcaacg caccgcaacc       360
tcactgttgg ggacggttct gacacagccg catactgtta cccgctatca gtcccgcgtg       420
gcagaaaaaa tcgttcgttt agaacactgg cagccacagc agagacgtga ggaagagacg       480
tcttttttggg tacttttttac tgcggatggt ttagtgcacc tattcggtaa gcatcaccat       540
gcacgtattg ctgacccgca ggatgaaacc agaattgccc gctggctgat ggaggaaacc       600
gtcacgcata ccggggaaca tatttactat cactatcggg cagaagacga tcttgactgt       660
gatgagcatg aacttgctca gcattcaggt gttacggccc agcgttatct ggcaaaagtc       720
agctatggca atactcagcc ggaaaccgct tttttcgcgg taaatcagg tattcctgct         780
gataatgact ggctgtttca tctggtatttt gattacggtg agcgctcatc ttcgctgaac      840
tctgtacccg aattcaatgt gtcagaaaac aatgtgtctg aaacaatgt gcctgaaaaa        900
tggcgttgtc gtccggacag tttctcccgc tatgaatatg ggtttgaaat tcgaacccgt       960

-continued

```
cgcttgtgtc gccaagttct gatgtttcat cagctgaaag cgctggcagg ggaaaaggtt    1020
gcagaagaaa caccggcgct ggtttcccgt cttattctgg attatgacct gaacaacaag    1080
gtttccttgc tgcaaacggc cgcagactg gcccatgaaa cggacggtac gccagtgatg     1140
atgtccccgc tggaaatgga ttatcaacgt gttaatcatg gcgtgaatct gaactggcag    1200
tccatgccgc agttagaaaa aatgaacacg ttgcagccat accaattggt tgatttatat    1260
ggagaaggaa tttccggcgt actttatcag gatactcaga aagcctggtg gtaccgtgct    1320
ccggtacggg atatcactgc cgaaggaacg aatgcggtta cctatgagga ggccaaacca    1380
ctgccacata ttccggcaca acaggaaagc gcgatgttgt tggacatcaa tggtgacggg    1440
cgtctggatt gggtgattac ggcatcaggg ttacgggct accacaccat gtcaccggaa     1500
ggtgaatgga caccctttat tccattatcc gctgtgccaa tggaatattt ccatccgcag    1560
gcaaaactgg ctgatattga tggggctggg ctgcctgact tagcgcttat cgggccaaat    1620
agtgtacgtg tctggtcaaa taatcgggca ggatgggatc gcgctcagga tgtgattcat    1680
ttgtcagata tgccactgcc ggttcccggc agaaatgagc gtcatcttgt cgcattcagt    1740
gatatgacag gctccgggca atcacatctg gtggaagtaa cggcagatag cgtgcgctac    1800
tggccgaacc tggggcatgg aaaatttggt gagcctctga tgatgacagg cttccagatt    1860
agcggggaaa cgtttaaccc cgacagactg tatatggtag acatagatgg ctcaggcacc    1920
accgatttta tttatgcccg caatacttac cttgaactct atgccaatga agcggcaat    1980 cattttgctg aacctcagcg tattgatctg ccggatgggg tacgttttga tgatacttgt    2040
cggttacaaa tagcggatac acaaggatta gggactgcca gcattatttt gacgatcccc    2100
catatgaagg tgcagcactg gcgattggat atgaccatat tcaagccttg gctgctgaat    2160
gccgtcaata acaatatggg aacagaaacc acgctgtatt atcgcagctc tgcccagttc    2220
tggctggatg agaaattaca ggcttctgaa tccgggatga cggtggtcag ctacttaccg    2280
ttcccggtgc atgtgttgtg gcgcacggaa gtgctggatg aaatttccgg taaccgattg    2340
accagccatt atcattactc acatggtgcc tgggatggtc tggaacggga gtttcgtggt    2400
tttgggcggg tgacacaaac tgatattgat tcacgggcga gtgcgacaca ggggacacat    2460
gctgaaccac cggcaccttc gcgcacggtt aattggtacg gcactggcgt acgggaagtc    2520
gatattcttc tgcccacgga atattggcag ggggatcaac aggcatttcc ccattttacc    2580
ccacgcttta cccgttatga cgaaaaatcc ggtggtgata tgacggtcac gccgagcgaa    2640
caggaagaat actggttaca tcgagcctta aaaggacaac gtttacgcag tgagctgtat    2700
ggggatgatg attctatact ggccggtacg ccttattcag tggatgaatc ccgcacccaa    2760
gtacgtttgt taccggtgat ggtatcgac gtgcctgcgg tactggtttc ggtggccgaa     2820
tcccgccaat accgatatga acgggttgct accgatccac agtgcagcca aaagatcgtc    2880
cttaaatctg atgcgttagg atttccgcag gacaatcttg agattgccta ttcgagacgt    2940
ccacagcctg agttctcgcc ttatccggat accctgcccg aaacacttt caccagcagt     3000 ttcgacgaac agcagatgtt ccttcgtctg acacgccagc gttcttctta tcatcatctg    3060
aatcatgatg ataatacgtg gatcacaggg cttatggata cctcacgcag tgacgcacgt    3120
atttatcaag ccgataaagt gccggacggt ggatttccc ttgaatggtt ttctgccaca     3180
ggtgcaggag cattgttgtt gcctgatgcc gcagccgatt atctgggaca tcagcgtgta    3240
gcatataccg gtccagaaga acaacccgct attcctccgc tggtggcata cattgaaacc    3300
gcagagtttg atgaacgatc gttggcggct tttgaggagg tgatggatga gcaggagctg    3360
```

-continued

```
acaaaacagc tgaatgatgc gggctggaat acggcaaaag tgccgttcag tgaaaagaca    3420
gatttccatg tctgggtggg acaaaaggaa tttacagaat atgccggtgc agacggattc    3480
tatcggccat tggtgcaacg ggaaaccaag cttacaggta aaacgacagt cacgtgggat    3540
agccattact gtgttatcac cgcaacagag gatgcggctg gcctgcgtat gcaagcgcat    3600
tacgattatc gatttatggt tgcggataac accacagatg tcaatgataa ctatcacacc    3660
gtgacgtttg atgcactggg gagggtaacc agcttccgtt tctgggggac tgaaaacggt    3720 gaaaacaag gatataccc tgcggaaaat gaaactgtcc cctttattgt ccccacaacg      3780
gtggatgatg ctctggcatt gaaacccggt atacctgttg cagggctgat ggtttatgcc    3840
cctctgagct ggatggttca ggccagcttt tctaatgatg gggagcttta tggagagctg    3900
aaaccggctg gatcatcac tgaagatggt tatctcctgt cgcttgcttt tcgccgctgg     3960
caacaaaata accctgccgc tgccatgcca aagcaagtca attcacagaa cccacccat    4020 gtactgagtg tgatcaccga ccgctatgat gccgatccgg aacaacaatt acgtcaaacg    4080
tttacgttta gtgatggttt tgggcgaacc ttacaaacag ccgtacgcca tgaaagtggt    4140
gaagcctggg tacgtgatga gtatggagcc attgtggctg aaaatcatgg cgcgcctgaa    4200
acggcgatga cagatttccg ttgggcagtt tccggacgta cagaatatga cggaaaaggc    4260
caagccctgc gtaagtatca accgtatttc ctgaatagtt ggcagtacgt cagtgatgac    4320
agtgcccggc aggatatata tgccgatacc cattactatg atccgttggg gcgtgaatat    4380
caggttatca cggccaaagg cgggtttcgt cgatccttat tcactccctg gtttgtggtg    4440
aatgaagatg aaaatgacac tgccggtgaa atgacagca                            4479
```

```
<210> SEQ ID NO 18
<211> LENGTH: 1493
<212> TYPE: PRT
<213> ORGANISM: Xenorhabdus nematophilus

<400> SEQUENCE: 18
```

```
Met Gln Gly Ser Thr Pro Leu Lys Leu Glu Ile Pro Ser Leu Pro Ser
1               5                   10                  15

Gly Gly Gly Ser Leu Lys Gly Met Gly Glu Ala Leu Asn Ala Val Gly
            20                  25                  30

Ala Glu Gly Gly Ala Ser Phe Ser Leu Pro Leu Pro Ile Ser Val Gly
        35                  40                  45

Arg Gly Leu Val Pro Val Leu Ser Leu Asn Tyr Ser Ser Thr Ala Gly
    50                  55                  60

Asn Gly Ser Phe Gly Met Gly Trp Gln Cys Gly Val Gly Phe Ile Ser
65                  70                  75                  80

Leu Arg Thr Ala Lys Gly Val Pro His Tyr Thr Gly Gln Asp Glu Tyr
                85                  90                  95

Leu Gly Pro Asp Gly Glu Val Leu Ser Ile Val Pro Asp Ser Gln Gly
            100                 105                 110

Gln Pro Glu Gln Arg Thr Ala Thr Ser Leu Leu Gly Thr Val Leu Thr
        115                 120                 125

Gln Pro His Thr Val Thr Arg Tyr Gln Ser Arg Val Ala Glu Lys Ile
    130                 135                 140

Val Arg Leu Glu His Trp Gln Pro Gln Gln Arg Glu Glu Glu Thr
145                 150                 155                 160

Ser Phe Trp Val Leu Phe Thr Ala Asp Gly Leu Val His Leu Phe Gly
                165                 170                 175
```

```
Lys His His His Ala Arg Ile Ala Asp Pro Gln Asp Glu Thr Arg Ile
            180                 185                 190
Ala Arg Trp Leu Met Glu Glu Thr Val Thr His Thr Gly Glu His Ile
        195                 200                 205
Tyr Tyr His Tyr Arg Ala Glu Asp Asp Leu Asp Cys Asp Glu His Glu
    210                 215                 220
Leu Ala Gln His Ser Gly Val Thr Ala Gln Arg Tyr Leu Ala Lys Val
225                 230                 235                 240
Ser Tyr Gly Asn Thr Gln Pro Glu Thr Ala Phe Phe Ala Val Lys Ser
            245                 250                 255
Gly Ile Pro Ala Asp Asn Asp Trp Leu Phe His Leu Val Phe Asp Tyr
        260                 265                 270
Gly Glu Arg Ser Ser Ser Leu Asn Ser Val Pro Glu Phe Asn Val Ser
    275                 280                 285
Glu Asn Asn Val Ser Glu Asn Asn Val Pro Glu Lys Trp Arg Cys Arg
290                 295                 300
Pro Asp Ser Phe Ser Arg Tyr Glu Tyr Gly Phe Glu Ile Arg Thr Arg
305                 310                 315                 320
Arg Leu Cys Arg Gln Val Leu Met Phe His Gln Leu Lys Ala Leu Ala
            325                 330                 335
Gly Glu Lys Val Ala Glu Thr Pro Ala Leu Val Ser Arg Leu Ile
        340                 345                 350
Leu Asp Tyr Asp Leu Asn Asn Lys Val Ser Leu Leu Gln Thr Ala Arg
    355                 360                 365
Arg Leu Ala His Glu Thr Asp Gly Thr Pro Val Met Met Ser Pro Leu
    370                 375                 380
Glu Met Asp Tyr Gln Arg Val Asn His Gly Val Asn Leu Asn Trp Gln
385                 390                 395                 400
Ser Met Pro Gln Leu Glu Lys Met Asn Thr Leu Gln Pro Tyr Gln Leu
            405                 410                 415
Val Asp Leu Tyr Gly Glu Gly Ile Ser Gly Val Leu Tyr Gln Asp Thr
        420                 425                 430
Gln Lys Ala Trp Trp Tyr Arg Ala Pro Val Arg Asp Ile Thr Ala Glu
    435                 440                 445
Gly Thr Asn Ala Val Thr Tyr Glu Glu Ala Lys Pro Leu Pro His Ile
450                 455                 460
Pro Ala Gln Gln Glu Ser Ala Met Leu Leu Asp Ile Asn Gly Asp Gly
465                 470                 475                 480
Arg Leu Asp Trp Val Ile Thr Ala Ser Gly Leu Arg Gly Tyr His Thr
            485                 490                 495
Met Ser Pro Glu Gly Glu Trp Thr Pro Phe Ile Pro Leu Ser Ala Val
        500                 505                 510
Pro Met Glu Tyr Phe His Pro Gln Ala Lys Leu Ala Asp Ile Asp Gly
    515                 520                 525
Ala Gly Leu Pro Asp Leu Ala Leu Ile Gly Pro Asn Ser Val Arg Val
530                 535                 540
Trp Ser Asn Asn Arg Ala Gly Trp Asp Arg Ala Gln Asp Val Ile His
545                 550                 555                 560
Leu Ser Asp Met Pro Leu Pro Val Pro Gly Arg Asn Glu Arg His Leu
            565                 570                 575
Val Ala Phe Ser Asp Met Thr Gly Ser Gly Gln Ser His Leu Val Glu
        580                 585                 590
```

-continued

```
Val Thr Ala Asp Ser Val Arg Tyr Trp Pro Asn Leu Gly His Gly Lys
        595                 600                 605

Phe Gly Glu Pro Leu Met Met Thr Gly Phe Gln Ile Ser Gly Glu Thr
    610                 615                 620

Phe Asn Pro Asp Arg Leu Tyr Met Val Asp Ile Asp Gly Ser Gly Thr
625                 630                 635                 640

Thr Asp Phe Ile Tyr Ala Arg Asn Thr Tyr Leu Glu Leu Tyr Ala Asn
                645                 650                 655

Glu Ser Gly Asn His Phe Ala Glu Pro Gln Arg Ile Asp Leu Pro Asp
            660                 665                 670

Gly Val Arg Phe Asp Asp Thr Cys Arg Leu Gln Ile Ala Asp Thr Gln
        675                 680                 685

Gly Leu Gly Thr Ala Ser Ile Ile Leu Thr Ile Pro His Met Lys Val
    690                 695                 700

Gln His Trp Arg Leu Asp Met Thr Ile Phe Lys Pro Trp Leu Leu Asn
705                 710                 715                 720

Ala Val Asn Asn Asn Met Gly Thr Glu Thr Thr Leu Tyr Tyr Arg Ser
                725                 730                 735

Ser Ala Gln Phe Trp Leu Asp Glu Lys Leu Gln Ala Ser Glu Ser Gly
            740                 745                 750

Met Thr Val Val Ser Tyr Leu Pro Phe Pro Val His Val Leu Trp Arg
        755                 760                 765

Thr Glu Val Leu Asp Glu Ile Ser Gly Asn Arg Leu Thr Ser His Tyr
    770                 775                 780

His Tyr Ser His Gly Ala Trp Asp Gly Leu Glu Arg Glu Phe Arg Gly
785                 790                 795                 800

Phe Gly Arg Val Thr Gln Thr Asp Ile Asp Ser Arg Ala Ser Ala Thr
                805                 810                 815

Gln Gly Thr His Ala Glu Pro Pro Ala Pro Ser Arg Thr Val Asn Trp
            820                 825                 830

Tyr Gly Thr Gly Val Arg Glu Val Asp Ile Leu Leu Pro Thr Glu Tyr
        835                 840                 845

Trp Gln Gly Asp Gln Gln Ala Phe Pro His Phe Thr Pro Arg Phe Thr
    850                 855                 860

Arg Tyr Asp Glu Lys Ser Gly Gly Asp Met Thr Val Thr Pro Ser Glu
865                 870                 875                 880

Gln Glu Glu Tyr Trp Leu His Arg Ala Leu Lys Gly Gln Arg Leu Arg
                885                 890                 895

Ser Glu Leu Tyr Gly Asp Asp Asp Ser Ile Leu Ala Gly Thr Pro Tyr
            900                 905                 910

Ser Val Asp Glu Ser Arg Thr Gln Val Arg Leu Leu Pro Val Met Val
        915                 920                 925

Ser Asp Val Pro Ala Val Leu Val Ser Val Ala Glu Ser Arg Gln Tyr
    930                 935                 940

Arg Tyr Glu Arg Val Ala Thr Asp Pro Gln Cys Ser Gln Lys Ile Val
945                 950                 955                 960

Leu Lys Ser Asp Ala Leu Gly Phe Pro Gln Asp Asn Leu Glu Ile Ala
                965                 970                 975

Tyr Ser Arg Arg Pro Gln Pro Glu Phe Ser Pro Tyr Pro Asp Thr Leu
            980                 985                 990

Pro Glu Thr Leu Phe Thr Ser Ser  Phe Asp Glu Gln Gln  Met Phe Leu
        995                 1000                1005

Arg Leu  Thr Arg Gln Arg Ser  Ser Tyr His His Leu  Asn His Asp
```

-continued

```
                1010                    1015                    1020
Asp Asn Thr Trp Ile Thr Gly Leu Met Asp Thr Ser Arg Ser Asp
            1025                    1030                    1035
Ala Arg Ile Tyr Gln Ala Asp Lys Val Pro Asp Gly Gly Phe Ser
            1040                    1045                    1050
Leu Glu Trp Phe Ser Ala Thr Gly Ala Gly Ala Leu Leu Leu Pro
            1055                    1060                    1065
Asp Ala Ala Ala Asp Tyr Leu Gly His Gln Arg Val Ala Tyr Thr
            1070                    1075                    1080
Gly Pro Glu Glu Gln Pro Ala Ile Pro Pro Leu Val Ala Tyr Ile
            1085                    1090                    1095
Glu Thr Ala Glu Phe Asp Glu Arg Ser Leu Ala Ala Phe Glu Glu
            1100                    1105                    1110
Val Met Asp Glu Gln Glu Leu Thr Lys Gln Leu Asn Asp Ala Gly
            1115                    1120                    1125
Trp Asn Thr Ala Lys Val Pro Phe Ser Glu Lys Thr Asp Phe His
            1130                    1135                    1140
Val Trp Val Gly Gln Lys Glu Phe Thr Glu Tyr Ala Gly Ala Asp
            1145                    1150                    1155
Gly Phe Tyr Arg Pro Leu Val Gln Arg Glu Thr Lys Leu Thr Gly
            1160                    1165                    1170
Lys Thr Thr Val Thr Trp Asp Ser His Tyr Cys Val Ile Thr Ala
            1175                    1180                    1185
Thr Glu Asp Ala Ala Gly Leu Arg Met Gln Ala His Tyr Asp Tyr
            1190                    1195                    1200
Arg Phe Met Val Ala Asp Asn Thr Thr Asp Val Asn Asp Asn Tyr
            1205                    1210                    1215
His Thr Val Thr Phe Asp Ala Leu Gly Arg Val Thr Ser Phe Arg
            1220                    1225                    1230
Phe Trp Gly Thr Glu Asn Gly Glu Lys Gln Gly Tyr Thr Pro Ala
            1235                    1240                    1245
Glu Asn Glu Thr Val Pro Phe Ile Val Pro Thr Thr Val Asp Asp
            1250                    1255                    1260
Ala Leu Ala Leu Lys Pro Gly Ile Pro Val Ala Gly Leu Met Val
            1265                    1270                    1275
Tyr Ala Pro Leu Ser Trp Met Val Gln Ala Ser Phe Ser Asn Asp
            1280                    1285                    1290
Gly Glu Leu Tyr Gly Glu Leu Lys Pro Ala Gly Ile Ile Thr Glu
            1295                    1300                    1305
Asp Gly Tyr Leu Leu Ser Leu Ala Phe Arg Arg Trp Gln Gln Asn
            1310                    1315                    1320
Asn Pro Ala Ala Ala Met Pro Lys Gln Val Asn Ser Gln Asn Pro
            1325                    1330                    1335
Pro His Val Leu Ser Val Ile Thr Asp Arg Tyr Asp Ala Asp Pro
            1340                    1345                    1350
Glu Gln Gln Leu Arg Gln Thr Phe Thr Phe Ser Asp Gly Phe Gly
            1355                    1360                    1365
Arg Thr Leu Gln Thr Ala Val Arg His Glu Ser Gly Glu Ala Trp
            1370                    1375                    1380
Val Arg Asp Glu Tyr Gly Ala Ile Val Ala Glu Asn His Gly Ala
            1385                    1390                    1395
Pro Glu Thr Ala Met Thr Asp Phe Arg Trp Ala Val Ser Gly Arg
            1400                    1405                    1410
```

```
Thr Glu Tyr Asp Gly Lys Gly Gln Ala Leu Arg Lys Tyr Gln Pro
    1415                1420                1425

Tyr Phe Leu Asn Ser Trp Gln Tyr Val Ser Asp Asp Ser Ala Arg
    1430                1435                1440

Gln Asp Ile Tyr Ala Asp Thr His Tyr Tyr Asp Pro Leu Gly Arg
    1445                1450                1455

Glu Tyr Gln Val Ile Thr Ala Lys Gly Gly Phe Arg Arg Ser Leu
    1460                1465                1470

Phe Thr Pro Trp Phe Val Val Asn Glu Asp Glu Asn Asp Thr Ala
    1475                1480                1485

Gly Glu Met Thr Ala
    1490

<210> SEQ ID NO 19
<211> LENGTH: 7614
<212> TYPE: DNA
<213> ORGANISM: Xenorhabdus nematophilus

<400> SEQUENCE: 19
atgtatagca cggctgtatt actcaataaa atcagtccca ctcgcgacgg tcagacgatg      60
actcttgcgg atctgcaata tttatccttc agtgaactga gaaaaatctt tgatgaccag     120
ctcagttggg gagaggctcg ccatctctat catgaaacta tagagcagaa aaaaaataat     180
cgcttgctgg aagcgcgtat ttttacccgt gccaacccac aattatccgg tgctatccga     240
ctcggtattg aacgagacag cgtttcacgc agttatgatg aaatgtttgg tgcccgttct     300
tcttcctttg tgaaaccggg ttcagtggct tccatgtttt caccggctgg ctatctcacc     360
gaattgtatc gtgaagcgaa ggacttacat ttttcaagct ctgcttatca tcttgataat     420
cgccgtccgg atctggctga tctgactctg agccagagta atatggatac agaaatttcc     480
accctgacac tgtctaacga actgttgctg gagcatatta cccgcaagac cggaggtgat     540
tcggacgcat tgatggagag cctgtcaact taccgtcagg ccattgatac cccttaccat     600
cagccttacg agactatccg tcaggtcatt atgacccatg acagtacact gtcagcgctg     660
tcccgtaatc ctgaggtgat ggggcaggcg aagggggctt cattactggc gattctggcc     720
aatatttctc cggagcttta taacattttg accgaagaga ttacggaaaa gaacgctgat     780
gctttatttg cgcaaaactt cagtgaaaat atcacgcccg aaaatttcgc gtcacaatca     840
tggatagcca agtattatgg tcttgaactt tctgaggtgc aaaaataccc tgggatgttg     900
cagaatggct attctgacag cacctctgct tatgtggata atatctcaac gggtttagtg     960
gtcaataatg aaagtaaact cgaagcttac aaaataacac gtgtaaaaac agatgattat    1020
gataaaaata taaattactt tgatttgatg tatgaaggaa ataatcagtt ctttatacgt    1080 gctaattta aggtatcaag agaatttggg gctactctta aaaaaaacgc agggccaagt    1140
ggcattgtcg gcagcctttc cggtcctcta atagccaata cgaattttaa aagtaattat    1200
ctaagtaaca tatctgattc tgaatacaaa acggtgtaa agatatacgc ctatcgctat    1260
acgtcttcca ccagcgccac aaatcagggc ggcggaatat tcacttttga gtcttatccc    1320
ctgactatat ttgcgctcaa actgaataaa gccattcgct tgtgcctgac tagcgggctt    1380
tcaccgaatg aactgcaaac tatcgtacgc agtgacaatg cacaaggcat catcaacgac    1440
tccgttctga ccaaagtttt ctatactctg ttctacagtc accgttatgc actgagcttt    1500
gatgatgcac aggtactgaa cggatcggtc attaatcaat atgccgacga tgacagtgtc    1560
```

-continued

```
agtcatttta accgtctctt taatacaccg ccgctgaaag ggaaaatctt tgaagccgac    1620
ggcaacacgg tcagcattga tccggatgaa gagcaatcta cctttgcccg ttcagccctg    1680
atgcgtggtc tggggtcaa cagtggtgaa ctgtatcagt taggcaaact ggcgggtgtg    1740
ctggacgccc aaaataccat cacactttct gtcttcgtta tctcttcact gtatcgcctc    1800
acgttactgg cccgtgtcca tcagctgacg gtcaatgaac tgtgtatgct ttatggtctt    1860
tcgccgttca atggcaaaac aacggcttct ttgtcttccg gggagttgcc acggctggtt    1920
atctggctgt atcaggtgac gcagtggctg actgaggcgg aaatcaccac tgaagcgatc    1980
tggttattat gtacgccaga gtttagcggg aatatttcac cggaaatcag taatctgctc    2040
aataacctcc gaccgagtat tagtgaagat atggcacaga gtcacaatcg ggagctgcag    2100
gctgaaattc tcgcgccgtt tattgctgca acgctgcatc tggcgtcacc ggatatggca    2160
cggtatatcc tgttgtggac cgataacctg cggccgggtg gcttagatat tgccgggttt    2220
atgacactgg tattgaaaga gtcgttaaat gccaatgaaa ccacccaatt ggtacaattc    2280
tgccatgtga tggcacagtt atcgctttcc gtacagacac tgcgcctcag tgaagcggag    2340
ctatccgtgc tggtcatctc cggattcgcc gtgctggggg caaaaaatca acctgccgga    2400
cagcacaata ttgatacgct attctcactc taccgattcc accagtggat taatgggctg    2460
ggcaatcccg gctctgacac gctggatatg ctgcgccagc agacactcac ggccgacaga    2520
ctggcctccg tgatggggct ggacatcagt atggtaacgc aggccatggt tccgccggc    2580 gtgaaccagc ttcagtgttg gcaggatatc aacaccgtgt tgcagtggat agatgtggca    2640
tcagcactgc acacgatgcc gtcggttatc cgtacgctgg tgaatatccg ttacgtgact    2700
gcattaaaca aagccgagtc gaatctgcct tcctgggatg agtggcagac actggcagaa    2760
aatatggaag ccggactcag tacacaacag gctcagacgc tggcggatta taccgcggag    2820
cgcctgagta gcgtgctgtg caattggttt ctggcgaata tccagccaga gggggtgtcc    2880
ctgcacagcc gggatgacct gtacagctat ttcctgattg ataatcaggt ctcttctgcc    2940
ataaaaacca cccgactggc agaggccatt gccggtattc agctctacat caaccgggcg    3000
ctgaatcgga tagagcctaa tgcccgtgcc gatgtgtcaa cccgccagtt ttttaccgac    3060
tggacggtga ataaccgtta cagcacctgg ggcggggtgt cgcggctggt ttattatccg    3120
gaaaattaca ttgacccaac ccagcgtatc gggcagaccc ggatgatgga tgaactgctg    3180
gaaaatatca gccagagtaa acttagccgg gacacagtgg aggatgcctt taaaacttac    3240
ctgacccgct ttgaaaccgt ggcggatctg aaagttgtca gcgcctatca cgacaacgtc    3300
aacagcaaca ccggactgac ctggtttgtc ggccaaacgc gggagaacct gccggaatac    3360
tactggcgta acgtggatat atcacggatg caggcgggtg aactggccgc caatgcctgg    3420
aaagagtgga cgaagattga tacagcggtc aacccctaca aggatgcaat acgtccggtc    3480
atattcaggg aacgtttgca ccttatctgg gtagaaaaag aggaagtggc gaaaatggt    3540 actgatccgg tggaaaccta tgaccgtttt actctgaaac tggcgtttct cgtcatgat    3600 ggcagttgga gtgccccctg gtcttacgat atcacaacgc aggtggaggc ggtcactgac    3660
aaaaaacctg acactgaacg gctggcgctg ccgcatcag ctttcagggg cgaggacact    3720
ctgctggtgt ttgtctacaa aaccgggaag agttactcgg attttggcgg cagcaataaa    3780
aatgtggcag gcatgaccat ttacggcgat ggctccttca aaagatggag gaacacagca    3840
ctcagccgtt acagccaact gaaaaatacc tttgatatca ttcatactca aggcaacgac    3900
ttggtaagaa aggccagcta tcgtttcgcg caggattttg aagtgcctgc ctcgttgaat    3960
```

```
atgggttctg ccatcggtga tgatagtctg acggtgatgg agaacgggaa tattccgcag    4020
ataaccagta aatactccag cgataacctt gctattacgc tacataacgc cgctttcact    4080
gtcagatatg atggcagtgg caatgtcatc agaaacaaac aaatcagcgc catgaaactg    4140 acggggtgg  atggaaagtc ccagtacggc aatgcattta tcatcgcaaa taccgttaaa    4200
cattatggcg gttactctga tctggggggg ccgatcaccg tttataataa acgaaaaac    4260 tatattgcat cagttcaagg ccacttgatg aacgcagatt acactaggcg tttgattcta    4320
acaccagttg aaaataatta ttatgccaga ttgttcgagt ttccattttc tccaaacaca    4380
attttaaaca ccgttttcac ggttggtagc aataaaacca gtgattttaa aaagtgcagt    4440
tatgctgttg atggtaataa ttctcagggc ttccagatat ttagttccta tcaatcatcc    4500
ggctggctgg atattgatac aggcattaac aataccgata tcaaaattac ggtgatggct    4560
ggcagtaaaa cccacacctt tacgccagt  gaccatattg cttccttgcc ggcaaacagt    4620
tttgatgcta tgccgtacac ctttaagcca ctggaaatcg atgcttcatc gttggccttt    4680
accaataata ttgctcctct ggatatcgtt tttgagacca agccaaaga  cgggcgagtg    4740 ctgggtaaga tcaagcaaac attatcggtg aaacgggtaa attataatcc ggaagatatt    4800
ctgtttctgc gtgaaactca ttcgggtgcc caatatatgc agctcggggt gtatcgtatt    4860
cgtcttaata ccctgctggc ttctcaactg gtatccagag caaacacggg cattgatact    4920
atcctgacaa tggaaaccca gcggttaccg gaacctccgt tgggagaagg cttcttgcc    4980 aactttgttc tgcctaaata tgaccctgct gaacatggcg atgagcggtg gtttaaaatc    5040
catattggga atgttggcgg taacacggga aggcagcctt attacagcgg aatgttatcc    5100
gatacgtcgg aaaccagtat gacactgttt gtcccttatg ccgaagggta ttacatgcat    5160
gaaggtgtca gattgggggt tggataccag aaaattacct atgacaacac ttgggaatct    5220
gctttctttt attttgatga gacaaaaacag caatttgtat taattaacga tgctgatcat    5280
gattcaggaa tgacgcaaca ggggatcgtg aaaaatatca agaaatacaa aggattttg    5340 aatgttctcta tcgcaacggg ctattccgcc ccgatggatt tcaatagtgc cagcgccctc    5400
tattactggg aattgttcta ttacaccccg atgatgtgct tccagcgttt gctacaggaa    5460
aaacaattcg acgaagccac acaatggata aactacgtct acaatccgc  cggctatatc    5520 gttaacggag aaatcgcccc ctggatctgg aactgccggc cgctggaaga gaccacctcc    5580
tggaatgcca atccgctgga tgccatcgat ccggatgccg tcgcccaaaa tgacccaatg    5640
cactacaaga ttgccacctt tatgcgcctg ttggatcaac ttattctgcg cggcgatatg    5700
gcctatcgag aactgacccg cgatgcgttg aatgaagcca aatgtggta  tgtgcgtact    5760 ttagaattgc tcggtgatga gccggaggat tacggtagcc aacagtgggc agcaccgtcc    5820
ctttccgggg cggcgagtca aaccgtgcag gcggcttatc agcaggatct tacgatgctg    5880
ggccgtggtg gggttccaa  gaatctccgt accgctaact cgttggtggg tttgttcctg    5940
ccggaatata cccggcgct  caccgattac tggcaaaccc tgcgtttgcg cctgtttaac    6000
ctgcgccata atctttccat tgacggacag ccgttatcgc tggcgattta cgccgagcct    6060
accgatccga aagcgctgct caccagtatg gtacaggcct ctcagggcgg tagtgcagtg    6120
ctgcccggca cattgtcgtt ataccgcttc ccggtgatgc tggagcggac ccgcaatctg    6180
gtagcgcaat taacccagtt cggcacctct ctgctcagta tggcagagca tgatgatgcc    6240
gatgaactca ccacgctgct actacagcag ggtatggaac tggcgacaca gagcatccgt    6300
```

```
attcagcaac gaactgtcga tgaagtggat gctgatattg ctgtattggc agagagccgc   6360
cgcagtgcac aaaatcgtct ggaaaaatac cagcagctgt atgacgagga tatcaaccac   6420
ggagaacagc gggcaatgtc actgcttgat gcagcggcag gtcagtctct ggccgggcag   6480
gtgctttcaa tagcggaagg ggtggccgat ttagtgccaa acgtgttcgg tttagcttgt   6540
ggcggcagtc gttgggggc agcactgcgt gcttccgcct ccgtgatgtc gctttctgcc   6600
acagcttccc aatattccgc agacaaaatc agccgttcgg aagcctaccg ccgccgccgt   6660
caggagtggg aaattcagcg tgataatgct gacggtgaag tcaaacaaat ggatgcccag   6720
ttggaaagcc tgaaaatccg ccgcgaagca gcacagatgc aggtggaata tcaggagacc   6780
cagcaggccc atactcaggc tcagttagag ctgttacagc gtaaattcac aaacaaagcg   6840
ctttacagtt ggatgcgcgg caagctgagt gctatctatt accagttctt tgacctgacc   6900
cagtccttct gcctgatggc acaggaagcg ctgcgccgcg agctgaccga caacggtgtt   6960
acctttatcc ggggtgggc ctggaacggt acgactgcgg gtttgatggc gggtgaaacg   7020
ttgctgctga atctggcaga aatggaaaaa gtctggctgg agcgtgatga gcggcactg   7080 gaagtgaccc gtaccgtctc gttggcacag ttctatcagg ccttatcatc agacaacttt   7140
aatctgaccg aaaaactcac gcaattcctg cgtgaaggga aaggcaacgt aggagcttcc   7200
ggcaatgaat taaaactcag taaccgtcag atagaagcct cagtgcgatt gtctgatttg   7260
aaaattttca gcgactaccc cgaaagcctt ggcaatacc gtcagttgaa acaggtgagt   7320
gtcaccttgc cggcgctggt tgggccgtat gaagatattc gggcggtgct gaattacggg   7380
ggcagcatcg tcatgccacg cggttgcagt gctattgctc tctcccacgg cgtgaatgac   7440
agtggtcaat ttatgctgga tttcaacgat tcccgttatc tgccgtttga aggtatttcc   7500
gtgaatgaca gcggcagcct gacgttgagt ttcccggatg cgactgatcg gcagaaagcg   7560
ctgctggaga gcctgagcga tatcattctg catatccgct ataccattcg ttct         7614
```

<210> SEQ ID NO 20
<211> LENGTH: 2538
<212> TYPE: PRT
<213> ORGANISM: Xenorhabdus nematophilus

<400> SEQUENCE: 20

Met Tyr Ser Thr Ala Val Leu Leu Asn Lys Ile Ser Pro Thr Arg Asp
1               5                   10                  15

Gly Gln Thr Met Thr Leu Ala Asp Leu Gln Tyr Leu Ser Phe Ser Glu
            20                  25                  30

Leu Arg Lys Ile Phe Asp Asp Gln Leu Ser Trp Gly Glu Ala Arg His
        35                  40                  45

Leu Tyr His Glu Thr Ile Glu Gln Lys Lys Asn Asn Arg Leu Leu Glu
    50                  55                  60

Ala Arg Ile Phe Thr Arg Ala Asn Pro Gln Leu Ser Gly Ala Ile Arg
65                  70                  75                  80

Leu Gly Ile Glu Arg Asp Ser Val Ser Arg Ser Tyr Asp Glu Met Phe
                85                  90                  95

Gly Ala Arg Ser Ser Phe Val Lys Pro Gly Ser Val Ala Ser Met
            100                 105                 110

Phe Ser Pro Ala Gly Tyr Leu Thr Glu Leu Tyr Arg Glu Ala Lys Asp
        115                 120                 125

Leu His Phe Ser Ser Ala Tyr His Leu Asp Asn Arg Arg Pro Asp
    130                 135                 140

```
Leu Ala Asp Leu Thr Leu Ser Gln Ser Asn Met Asp Thr Glu Ile Ser
145                 150                 155                 160

Thr Leu Thr Leu Ser Asn Glu Leu Leu Glu His Ile Thr Arg Lys
            165                 170                 175

Thr Gly Gly Asp Ser Asp Ala Leu Met Glu Ser Leu Ser Thr Tyr Arg
            180                 185                 190

Gln Ala Ile Asp Thr Pro Tyr His Gln Pro Tyr Glu Thr Ile Arg Gln
            195                 200                 205

Val Ile Met Thr His Asp Ser Thr Leu Ser Ala Leu Ser Arg Asn Pro
210                 215                 220

Glu Val Met Gly Gln Ala Glu Gly Ala Ser Leu Leu Ala Ile Leu Ala
225                 230                 235                 240

Asn Ile Ser Pro Glu Leu Tyr Asn Ile Leu Thr Glu Glu Ile Thr Glu
                245                 250                 255

Lys Asn Ala Asp Ala Leu Phe Ala Gln Asn Phe Ser Glu Asn Ile Thr
            260                 265                 270

Pro Glu Asn Phe Ala Ser Gln Ser Trp Ile Ala Lys Tyr Tyr Gly Leu
            275                 280                 285

Glu Leu Ser Glu Val Gln Lys Tyr Leu Gly Met Leu Gln Asn Gly Tyr
290                 295                 300

Ser Asp Ser Thr Ser Ala Tyr Val Asp Asn Ile Ser Thr Gly Leu Val
305                 310                 315                 320

Val Asn Asn Glu Ser Lys Leu Glu Ala Tyr Lys Ile Thr Arg Val Lys
                325                 330                 335

Thr Asp Asp Tyr Asp Lys Asn Ile Asn Tyr Phe Asp Leu Met Tyr Glu
            340                 345                 350

Gly Asn Asn Gln Phe Phe Ile Arg Ala Asn Phe Lys Val Ser Arg Glu
            355                 360                 365

Phe Gly Ala Thr Leu Arg Lys Asn Ala Gly Pro Ser Gly Ile Val Gly
            370                 375                 380

Ser Leu Ser Gly Pro Leu Ile Ala Asn Thr Asn Phe Lys Ser Asn Tyr
385                 390                 395                 400

Leu Ser Asn Ile Ser Asp Ser Glu Tyr Lys Asn Gly Val Lys Ile Tyr
                405                 410                 415

Ala Tyr Arg Tyr Thr Ser Ser Thr Ser Ala Thr Asn Gln Gly Gly Gly
            420                 425                 430

Ile Phe Thr Phe Glu Ser Tyr Pro Leu Thr Ile Phe Ala Leu Lys Leu
            435                 440                 445

Asn Lys Ala Ile Arg Leu Cys Leu Thr Ser Gly Leu Ser Pro Asn Glu
            450                 455                 460

Leu Gln Thr Ile Val Arg Ser Asp Asn Ala Gln Gly Ile Ile Asn Asp
465                 470                 475                 480

Ser Val Leu Thr Lys Val Phe Tyr Thr Leu Phe Tyr Ser His Arg Tyr
                485                 490                 495

Ala Leu Ser Phe Asp Asp Ala Gln Val Leu Asn Gly Ser Val Ile Asn
            500                 505                 510

Gln Tyr Ala Asp Asp Ser Val Ser His Phe Asn Arg Leu Phe Asn
            515                 520                 525

Thr Pro Pro Leu Lys Gly Lys Ile Phe Glu Ala Asp Gly Asn Thr Val
            530                 535                 540

Ser Ile Asp Pro Asp Glu Gln Ser Thr Phe Ala Arg Ser Ala Leu
545                 550                 555                 560

Met Arg Gly Leu Gly Val Asn Ser Gly Glu Leu Tyr Gln Leu Gly Lys
```

```
                    565                 570                 575
Leu Ala Gly Val Leu Asp Ala Gln Asn Thr Ile Thr Leu Ser Val Phe
                580                 585                 590
Val Ile Ser Ser Leu Tyr Arg Leu Thr Leu Leu Ala Arg Val His Gln
            595                 600                 605
Leu Thr Val Asn Glu Leu Cys Met Leu Tyr Gly Leu Ser Pro Phe Asn
        610                 615                 620
Gly Lys Thr Thr Ala Ser Leu Ser Ser Gly Glu Leu Pro Arg Leu Val
    625                 630                 635                 640
Ile Trp Leu Tyr Gln Val Thr Gln Trp Leu Thr Glu Ala Glu Ile Thr
                645                 650                 655
Thr Glu Ala Ile Trp Leu Leu Cys Thr Pro Glu Phe Ser Gly Asn Ile
                660                 665                 670
Ser Pro Glu Ile Ser Asn Leu Leu Asn Asn Leu Arg Pro Ser Ile Ser
            675                 680                 685
Glu Asp Met Ala Gln Ser His Asn Arg Glu Leu Gln Ala Glu Ile Leu
        690                 695                 700
Ala Pro Phe Ile Ala Ala Thr Leu His Leu Ala Ser Pro Asp Met Ala
705                 710                 715                 720
Arg Tyr Ile Leu Leu Trp Thr Asp Asn Leu Arg Pro Gly Leu Asp
                725                 730                 735
Ile Ala Gly Phe Met Thr Leu Val Leu Lys Glu Ser Leu Asn Ala Asn
                740                 745                 750
Glu Thr Thr Gln Leu Val Gln Phe Cys His Val Met Ala Gln Leu Ser
            755                 760                 765
Leu Ser Val Gln Thr Leu Arg Leu Ser Glu Ala Glu Leu Ser Val Leu
        770                 775                 780
Val Ile Ser Gly Phe Ala Val Leu Gly Ala Lys Asn Gln Pro Ala Gly
785                 790                 795                 800
Gln His Asn Ile Asp Thr Leu Phe Ser Leu Tyr Arg Phe His Gln Trp
                805                 810                 815
Ile Asn Gly Leu Gly Asn Pro Gly Ser Asp Thr Leu Asp Met Leu Arg
            820                 825                 830
Gln Gln Thr Leu Thr Ala Asp Arg Leu Ala Ser Val Met Gly Leu Asp
        835                 840                 845
Ile Ser Met Val Thr Gln Ala Met Val Ser Ala Gly Val Asn Gln Leu
    850                 855                 860
Gln Cys Trp Gln Asp Ile Asn Thr Val Leu Gln Trp Ile Asp Val Ala
865                 870                 875                 880
Ser Ala Leu His Thr Met Pro Ser Val Ile Arg Thr Leu Val Asn Ile
                885                 890                 895
Arg Tyr Val Thr Ala Leu Asn Lys Ala Glu Ser Asn Leu Pro Ser Trp
            900                 905                 910
Asp Glu Trp Gln Thr Leu Ala Glu Asn Met Glu Ala Gly Leu Ser Thr
        915                 920                 925
Gln Gln Ala Gln Thr Leu Ala Asp Tyr Thr Ala Glu Arg Leu Ser Ser
    930                 935                 940
Val Leu Cys Asn Trp Phe Leu Ala Asn Ile Gln Pro Glu Gly Val Ser
945                 950                 955                 960
Leu His Ser Arg Asp Asp Leu Tyr Ser Tyr Phe Leu Ile Asp Asn Gln
                965                 970                 975
Val Ser Ser Ala Ile Lys Thr Thr Arg Leu Ala Glu Ala Ile Ala Gly
            980                 985                 990
```

-continued

```
Ile Gln Leu Tyr Ile Asn Arg Ala  Leu Asn Arg Ile Glu  Pro Asn Ala
        995              1000              1005

Arg Ala  Asp Val Ser Thr Arg  Gln Phe Phe Thr Asp  Trp Thr Val
    1010              1015              1020

Asn Asn  Arg Tyr Ser Thr Trp  Gly Gly Val Ser Arg  Leu Val Tyr
    1025              1030              1035

Tyr Pro  Glu Asn Tyr Ile Asp  Pro Thr Gln Arg Ile  Gly Gln Thr
    1040              1045              1050

Arg Met  Met Asp Glu Leu Leu  Glu Asn Ile Ser Gln  Ser Lys Leu
    1055              1060              1065

Ser Arg  Asp Thr Val Glu Asp  Ala Phe Lys Thr Tyr  Leu Thr Arg
    1070              1075              1080

Phe Glu  Thr Val Ala Asp Leu  Lys Val Val Ser Ala  Tyr His Asp
    1085              1090              1095

Asn Val  Asn Ser Asn Thr Gly  Leu Thr Trp Phe Val  Gly Gln Thr
    1100              1105              1110

Arg Glu  Asn Leu Pro Glu Tyr  Tyr Trp Arg Asn Val  Asp Ile Ser
    1115              1120              1125

Arg Met  Gln Ala Gly Glu Leu  Ala Ala Asn Ala Trp  Lys Glu Trp
    1130              1135              1140

Thr Lys  Ile Asp Thr Ala Val  Asn Pro Tyr Lys Asp  Ala Ile Arg
    1145              1150              1155

Pro Val  Ile Phe Arg Glu Arg  Leu His Leu Ile Trp  Val Glu Lys
    1160              1165              1170

Glu Glu  Val Ala Lys Asn Gly  Thr Asp Pro Val Glu  Thr Tyr Asp
    1175              1180              1185

Arg Phe  Thr Leu Lys Leu Ala  Phe Leu Arg His Asp  Gly Ser Trp
    1190              1195              1200

Ser Ala  Pro Trp Ser Tyr Asp  Ile Thr Thr Gln Val  Glu Ala Val
    1205              1210              1215

Thr Asp  Lys Lys Pro Asp Thr  Glu Arg Leu Ala Leu  Ala Ala Ser
    1220              1225              1230

Gly Phe  Gln Gly Glu Asp Thr  Leu Leu Val Phe Val  Tyr Lys Thr
    1235              1240              1245

Gly Lys  Ser Tyr Ser Asp Phe  Gly Gly Ser Asn Lys  Asn Val Ala
    1250              1255              1260

Gly Met  Thr Ile Tyr Gly Asp  Gly Ser Phe Lys Lys  Met Glu Asn
    1265              1270              1275

Thr Ala  Leu Ser Arg Tyr Ser  Gln Leu Lys Asn Thr  Phe Asp Ile
    1280              1285              1290

Ile His  Thr Gln Gly Asn Asp  Leu Val Arg Lys Ala  Ser Tyr Arg
    1295              1300              1305

Phe Ala  Gln Asp Phe Glu Val  Pro Ala Ser Leu Asn  Met Gly Ser
    1310              1315              1320

Ala Ile  Gly Asp Asp Ser Leu  Thr Val Met Glu Asn  Gly Asn Ile
    1325              1330              1335

Pro Gln  Ile Thr Ser Lys Tyr  Ser Ser Asp Asn Leu  Ala Ile Thr
    1340              1345              1350

Leu His  Asn Ala Ala Phe Thr  Val Arg Tyr Asp Gly  Ser Gly Asn
    1355              1360              1365

Val Ile  Arg Asn Lys Gln Ile  Ser Ala Met Lys Leu  Thr Gly Val
    1370              1375              1380
```

-continued

```
Asp Gly Lys Ser Gln Tyr Gly Asn Ala Phe Ile Ile Ala Asn Thr
1385                1390                1395

Val Lys His Tyr Gly Gly Tyr Ser Asp Leu Gly Gly Pro Ile Thr
1400                1405                1410

Val Tyr Asn Lys Thr Lys Asn Tyr Ile Ala Ser Val Gln Gly His
1415                1420                1425

Leu Met Asn Ala Asp Tyr Thr Arg Arg Leu Ile Leu Thr Pro Val
1430                1435                1440

Glu Asn Asn Tyr Tyr Ala Arg Leu Phe Glu Phe Pro Phe Ser Pro
1445                1450                1455

Asn Thr Ile Leu Asn Thr Val Phe Thr Val Gly Ser Asn Lys Thr
1460                1465                1470

Ser Asp Phe Lys Lys Cys Ser Tyr Ala Val Asp Gly Asn Asn Ser
1475                1480                1485

Gln Gly Phe Gln Ile Phe Ser Ser Tyr Gln Ser Ser Gly Trp Leu
1490                1495                1500

Asp Ile Asp Thr Gly Ile Asn Asn Thr Asp Ile Lys Ile Thr Val
1505                1510                1515

Met Ala Gly Ser Lys Thr His Thr Phe Thr Ala Ser Asp His Ile
1520                1525                1530

Ala Ser Leu Pro Ala Asn Ser Phe Asp Ala Met Pro Tyr Thr Phe
1535                1540                1545

Lys Pro Leu Glu Ile Asp Ala Ser Ser Leu Ala Phe Thr Asn Asn
1550                1555                1560

Ile Ala Pro Leu Asp Ile Val Phe Glu Thr Lys Ala Lys Asp Gly
1565                1570                1575

Arg Val Leu Gly Lys Ile Lys Gln Thr Leu Ser Val Lys Arg Val
1580                1585                1590

Asn Tyr Asn Pro Glu Asp Ile Leu Phe Leu Arg Glu Thr His Ser
1595                1600                1605

Gly Ala Gln Tyr Met Gln Leu Gly Val Tyr Arg Ile Arg Leu Asn
1610                1615                1620

Thr Leu Leu Ala Ser Gln Leu Val Ser Arg Ala Asn Thr Gly Ile
1625                1630                1635

Asp Thr Ile Leu Thr Met Glu Thr Gln Arg Leu Pro Glu Pro Pro
1640                1645                1650

Leu Gly Glu Gly Phe Phe Ala Asn Phe Val Leu Pro Lys Tyr Asp
1655                1660                1665

Pro Ala Glu His Gly Asp Glu Arg Trp Phe Lys Ile His Ile Gly
1670                1675                1680

Asn Val Gly Gly Asn Thr Gly Arg Gln Pro Tyr Tyr Ser Gly Met
1685                1690                1695

Leu Ser Asp Thr Ser Glu Thr Ser Met Thr Leu Phe Val Pro Tyr
1700                1705                1710

Ala Glu Gly Tyr Tyr Met His Glu Gly Val Arg Leu Gly Val Gly
1715                1720                1725

Tyr Gln Lys Ile Thr Tyr Asp Asn Thr Trp Glu Ser Ala Phe Phe
1730                1735                1740

Tyr Phe Asp Glu Thr Lys Gln Gln Phe Val Leu Ile Asn Asp Ala
1745                1750                1755

Asp His Asp Ser Gly Met Thr Gln Gln Gly Ile Val Lys Asn Ile
1760                1765                1770

Lys Lys Tyr Lys Gly Phe Leu Asn Val Ser Ile Ala Thr Gly Tyr
```

-continued

|  | 1775 |  |  |  | 1780 |  |  |  | 1785 |  |  |
|---|---|---|---|---|---|---|---|---|---|---|---|
| Ser | Ala | Pro | Met | Asp | Phe | Asn | Ser | Ala | Ser | Ala | Leu | Tyr | Tyr | Trp |
|  | 1790 |  |  |  | 1795 |  |  |  | 1800 |  |  |

Ser Ala Pro Met Asp Phe Asn Ser Ala Ser Ala Leu Tyr Tyr Trp
         1790                1795                1800

Glu Leu Phe Tyr Tyr Thr Pro Met Met Cys Phe Gln Arg Leu Leu
         1805                1810                1815

Gln Glu Lys Gln Phe Asp Glu Ala Thr Gln Trp Ile Asn Tyr Val
         1820                1825                1830

Tyr Asn Pro Ala Gly Tyr Ile Val Asn Gly Glu Ile Ala Pro Trp
         1835                1840                1845

Ile Trp Asn Cys Arg Pro Leu Glu Glu Thr Thr Ser Trp Asn Ala
         1850                1855                1860

Asn Pro Leu Asp Ala Ile Asp Pro Asp Ala Val Ala Gln Asn Asp
         1865                1870                1875

Pro Met His Tyr Lys Ile Ala Thr Phe Met Arg Leu Leu Asp Gln
         1880                1885                1890

Leu Ile Leu Arg Gly Asp Met Ala Tyr Arg Glu Leu Thr Arg Asp
         1895                1900                1905

Ala Leu Asn Glu Ala Lys Met Trp Tyr Val Arg Thr Leu Glu Leu
         1910                1915                1920

Leu Gly Asp Glu Pro Glu Asp Tyr Gly Ser Gln Gln Trp Ala Ala
         1925                1930                1935

Pro Ser Leu Ser Gly Ala Ala Ser Gln Thr Val Gln Ala Ala Tyr
         1940                1945                1950

Gln Gln Asp Leu Thr Met Leu Gly Arg Gly Gly Val Ser Lys Asn
         1955                1960                1965

Leu Arg Thr Ala Asn Ser Leu Val Gly Leu Phe Leu Pro Glu Tyr
         1970                1975                1980

Asn Pro Ala Leu Thr Asp Tyr Trp Gln Thr Leu Arg Leu Arg Leu
         1985                1990                1995

Phe Asn Leu Arg His Asn Leu Ser Ile Asp Gly Gln Pro Leu Ser
         2000                2005                2010

Leu Ala Ile Tyr Ala Glu Pro Thr Asp Pro Lys Ala Leu Leu Thr
         2015                2020                2025

Ser Met Val Gln Ala Ser Gln Gly Gly Ser Ala Val Leu Pro Gly
         2030                2035                2040

Thr Leu Ser Leu Tyr Arg Phe Pro Val Met Leu Glu Arg Thr Arg
         2045                2050                2055

Asn Leu Val Ala Gln Leu Thr Gln Phe Gly Thr Ser Leu Leu Ser
         2060                2065                2070

Met Ala Glu His Asp Asp Ala Asp Glu Leu Thr Thr Leu Leu Leu
         2075                2080                2085

Gln Gln Gly Met Glu Leu Ala Thr Gln Ser Ile Arg Ile Gln Gln
         2090                2095                2100

Arg Thr Val Asp Glu Val Asp Ala Asp Ile Ala Val Leu Ala Glu
         2105                2110                2115

Ser Arg Arg Ser Ala Gln Asn Arg Leu Glu Lys Tyr Gln Gln Leu
         2120                2125                2130

Tyr Asp Glu Asp Ile Asn His Gly Glu Gln Arg Ala Met Ser Leu
         2135                2140                2145

Leu Asp Ala Ala Ala Gly Gln Ser Leu Ala Gly Gln Val Leu Ser
         2150                2155                2160

Ile Ala Glu Gly Val Ala Asp Leu Val Pro Asn Val Phe Gly Leu
         2165                2170                2175

```
Ala Cys Gly Gly Ser Arg Trp Gly Ala Ala Leu Arg Ala Ser Ala
    2180                2185                2190

Ser Val Met Ser Leu Ser Ala Thr Ala Ser Gln Tyr Ser Ala Asp
    2195                2200                2205

Lys Ile Ser Arg Ser Glu Ala Tyr Arg Arg Arg Gln Glu Trp
    2210                2215                2220

Glu Ile Gln Arg Asp Asn Ala Asp Gly Glu Val Lys Gln Met Asp
    2225                2230                2235

Ala Gln Leu Glu Ser Leu Lys Ile Arg Arg Glu Ala Ala Gln Met
    2240                2245                2250

Gln Val Glu Tyr Gln Glu Thr Gln Gln Ala His Thr Gln Ala Gln
    2255                2260                2265

Leu Glu Leu Leu Gln Arg Lys Phe Thr Asn Lys Ala Leu Tyr Ser
    2270                2275                2280

Trp Met Arg Gly Lys Leu Ser Ala Ile Tyr Tyr Gln Phe Phe Asp
    2285                2290                2295

Leu Thr Gln Ser Phe Cys Leu Met Ala Gln Glu Ala Leu Arg Arg
    2300                2305                2310

Glu Leu Thr Asp Asn Gly Val Thr Phe Ile Arg Gly Gly Ala Trp
    2315                2320                2325

Asn Gly Thr Thr Ala Gly Leu Met Ala Gly Glu Thr Leu Leu Leu
    2330                2335                2340

Asn Leu Ala Glu Met Glu Lys Val Trp Leu Glu Arg Asp Glu Arg
    2345                2350                2355

Ala Leu Glu Val Thr Arg Thr Val Ser Leu Ala Gln Phe Tyr Gln
    2360                2365                2370

Ala Leu Ser Ser Asp Asn Phe Asn Leu Thr Glu Lys Leu Thr Gln
    2375                2380                2385

Phe Leu Arg Glu Gly Lys Gly Asn Val Gly Ala Ser Gly Asn Glu
    2390                2395                2400

Leu Lys Leu Ser Asn Arg Gln Ile Glu Ala Ser Val Arg Leu Ser
    2405                2410                2415

Asp Leu Lys Ile Phe Ser Asp Tyr Pro Glu Ser Leu Gly Asn Thr
    2420                2425                2430

Arg Gln Leu Lys Gln Val Ser Val Thr Leu Pro Ala Leu Val Gly
    2435                2440                2445

Pro Tyr Glu Asp Ile Arg Ala Val Leu Asn Tyr Gly Gly Ser Ile
    2450                2455                2460

Val Met Pro Arg Gly Cys Ser Ala Ile Ala Leu Ser His Gly Val
    2465                2470                2475

Asn Asp Ser Gly Gln Phe Met Leu Asp Phe Asn Asp Ser Arg Tyr
    2480                2485                2490

Leu Pro Phe Glu Gly Ile Ser Val Asn Asp Ser Gly Ser Leu Thr
    2495                2500                2505

Leu Ser Phe Pro Asp Ala Thr Asp Arg Gln Lys Ala Leu Leu Glu
    2510                2515                2520

Ser Leu Ser Asp Ile Ile Leu His Ile Arg Tyr Thr Ile Arg Ser
    2525                2530                2535

<210> SEQ ID NO 21
<211> LENGTH: 1947
<212> TYPE: DNA
<213> ORGANISM: Xenorhabdus nematophilus
```

<400> SEQUENCE: 21

```
atgtctcaaa atgtttatcg ataccottca attaaagcga tgtctgacgc cagcagcgaa      60
gtaggcgcat ctctggttgc ctggcagaat caatctggtg gtcaaacctg gtatgtcatt     120
tatgatagcg cggtttttaa aaacatcggc tgggttgaac gctggcatat tcccgaccgc     180
aatatttcac ctgatttacc ggtttatgag aatgcctggc aatatgtccg tgaggcgaca     240
ccggaagaaa ttgccgatca cggtaacccc aatacgcctg atgtaccgcc gggagaaaaa     300
accgaggtat tgcaatatga tgcactcaca gaagaaacct atcagaaggt gggatataaa     360
cctgacggca gcggaactcc tttgagttat tcttcagcac gtgttgccaa gtccctgtac     420
aacgaatatg aagttgatcc ggaaaataca gaaccgctgc ctaaagtctc tgcctatatt     480
actgactggt gccagtatga tgcgcgtttg tcgccagaaa cccaggataa cactgcgctg     540
accagcgacg atgcccccgg ccgtggtttt gatctggaaa aaatcccgcc taccgcctac     600
gaccgcctga ttttcagttt tatggccgtc aacggtgata aggcaagtt atccgaacgg     660
attaatgagg ttgttgacgg gtggaaccgg caagcagaag ccagcagtgg ccagattgcc     720
cctattacat taggccatat tgtacccgtt gatccttatg gtgatttagg caccacacgc     780
aatgtcggtc tggacgcgga tcagcgccgt gatgccagcc cgaagaattt cttgcaatat     840
tacaatcagg atgcagcctc cggtttactg ggggattgc gtaatctgaa agcgcgagca     900
aaacaggcag ggcacaagct ggaactcgca ttcagtatcg gcggctggag tatgtcaggg     960
tatttctctg tgatggccaa agatcctgag caacgtgcta catttgtgag tagcatcgtc    1020
gacttcttcc ggcgttttcc catgtttact gcggtggata tcgactggga ataccccggc    1080
gccacaggtg aagaaggtaa tgaattcgac ccggaacatg atggcccaaa ctatgttttg    1140
ttagtgaaag agctgcgtga agcactgaac atcgcctttg gaacccgggc ccgtaaagaa    1200
atcacgatag cctgtagcgc cgtcgttgcc aaaatggaga gtccagctt caaagaaatc    1260
gcaccttatt tagacaatat cttttgtgatg acctacgact tctttggtac cggttgggca    1320
gaatacatcg gtcaccatac taacctgtat ccccccagat atgaatatga cggcgataac    1380
cctcctccgc ccaatcctga tcgggacatg gattactcgg ctgatgaggc gatccgcttt    1440
ttactgtcac aaggtgtaca accggagaaa attcacctcg gatttgctaa ctatggacgt    1500
tcatgtctgg gtgctgatct gacaactcgc cgctataaca gaacaggaga gccactgggc    1560
acgatggaaa aagtgctcc ggaattcttc tgtctgctga taaccaata cgatgcggaa    1620
tatgaaattg cacgcgggaa aaatcagttt gaactggtga cagacacgga aaccgacgct    1680
gacgcactct ttaatgctga cggtggtcac tggatttcac tggatacgcc ccgcactgtg    1740
ctgcataagg gaatttatgc aaccaaaatg aaattgggcg ggatcttctc ttggtcaggc    1800
gatcaggatg atggcctgtt ggcaaatgct gctcacgaag gtttgggtta cttacctgta    1860
cgcggaaaag agaagattga tatgggaccg ttatataaca aggacgtct cattcagctt    1920
cctaaagtaa cccgtcgtaa atcgtag                                         1947
```

<210> SEQ ID NO 22
<211> LENGTH: 648
<212> TYPE: PRT
<213> ORGANISM: Xenorhabdus nematophilus

<400> SEQUENCE: 22

```
Met Ser Gln Asn Val Tyr Arg Tyr Pro Ser Ile Lys Ala Met Ser Asp
 1               5                  10                  15
```

-continued

```
Ala Ser Ser Glu Val Gly Ala Ser Leu Val Ala Trp Gln Asn Gln Ser
         20                  25                  30
Gly Gly Gln Thr Trp Tyr Val Ile Tyr Asp Ser Ala Val Phe Lys Asn
         35                  40                  45
Ile Gly Trp Val Glu Arg Trp His Ile Pro Asp Arg Asn Ile Ser Pro
 50                  55                  60
Asp Leu Pro Val Tyr Glu Asn Ala Trp Gln Tyr Val Arg Glu Ala Thr
 65                  70                  75                  80
Pro Glu Glu Ile Ala Asp His Gly Asn Pro Asn Thr Pro Asp Val Pro
                 85                  90                  95
Pro Gly Glu Lys Thr Glu Val Leu Gln Tyr Asp Ala Leu Thr Glu Glu
                100                 105                 110
Thr Tyr Gln Lys Val Gly Tyr Lys Pro Asp Gly Ser Gly Thr Pro Leu
            115                 120                 125
Ser Tyr Ser Ser Ala Arg Val Ala Lys Ser Leu Tyr Asn Glu Tyr Glu
    130                 135                 140
Val Asp Pro Glu Asn Thr Glu Pro Leu Pro Lys Val Ser Ala Tyr Ile
145                 150                 155                 160
Thr Asp Trp Cys Gln Tyr Asp Ala Arg Leu Ser Pro Glu Thr Gln Asp
                165                 170                 175
Asn Thr Ala Leu Thr Ser Asp Ala Pro Gly Arg Gly Phe Asp Leu
            180                 185                 190
Glu Lys Ile Pro Pro Thr Ala Tyr Asp Arg Leu Ile Phe Ser Phe Met
        195                 200                 205
Ala Val Asn Gly Asp Lys Gly Lys Leu Ser Glu Arg Ile Asn Glu Val
    210                 215                 220
Val Asp Gly Trp Asn Arg Gln Ala Glu Ala Ser Ser Gly Gln Ile Ala
225                 230                 235                 240
Pro Ile Thr Leu Gly His Ile Val Pro Val Asp Pro Tyr Gly Asp Leu
                245                 250                 255
Gly Thr Thr Arg Asn Val Gly Leu Asp Ala Asp Gln Arg Arg Asp Ala
            260                 265                 270
Ser Pro Lys Asn Phe Leu Gln Tyr Tyr Asn Gln Asp Ala Ala Ser Gly
    275                 280                 285
Leu Leu Gly Gly Leu Arg Asn Leu Lys Ala Arg Ala Lys Gln Ala Gly
290                 295                 300
His Lys Leu Glu Leu Ala Phe Ser Ile Gly Gly Trp Ser Met Ser Gly
305                 310                 315                 320
Tyr Phe Ser Val Met Ala Lys Asp Pro Glu Gln Arg Ala Thr Phe Val
                325                 330                 335
Ser Ser Ile Val Asp Phe Phe Arg Arg Phe Pro Met Phe Thr Ala Val
            340                 345                 350
Asp Ile Asp Trp Glu Tyr Pro Gly Ala Thr Gly Glu Glu Gly Asn Glu
    355                 360                 365
Phe Asp Pro Glu His Asp Gly Pro Asn Tyr Val Leu Leu Val Lys Glu
370                 375                 380
Leu Arg Glu Ala Leu Asn Ile Ala Phe Gly Thr Arg Ala Arg Lys Glu
385                 390                 395                 400
Ile Thr Ile Ala Cys Ser Ala Val Val Ala Lys Met Glu Lys Ser Ser
                405                 410                 415
Phe Lys Glu Ile Ala Pro Tyr Leu Asp Asn Ile Phe Val Met Thr Tyr
            420                 425                 430
Asp Phe Phe Gly Thr Gly Trp Ala Glu Tyr Ile Gly His His Thr Asn
```

-continued

```
            435                 440                 445
Leu Tyr Pro Pro Arg Tyr Glu Tyr Asp Gly Asp Asn Pro Pro Pro
    450                 455                 460

Asn Pro Asp Arg Asp Met Asp Tyr Ser Ala Asp Glu Ala Ile Arg Phe
465                 470                 475                 480

Leu Leu Ser Gln Gly Val Gln Pro Glu Lys Ile His Leu Gly Phe Ala
                485                 490                 495

Asn Tyr Gly Arg Ser Cys Leu Gly Ala Asp Leu Thr Thr Arg Arg Tyr
                500                 505                 510

Asn Arg Thr Gly Glu Pro Leu Gly Thr Met Glu Lys Gly Ala Pro Glu
            515                 520                 525

Phe Phe Cys Leu Leu Asn Asn Gln Tyr Asp Ala Glu Tyr Glu Ile Ala
    530                 535                 540

Arg Gly Lys Asn Gln Phe Glu Leu Val Thr Asp Thr Glu Thr Asp Ala
545                 550                 555                 560

Asp Ala Leu Phe Asn Ala Asp Gly Gly His Trp Ile Ser Leu Asp Thr
                565                 570                 575

Pro Arg Thr Val Leu His Lys Gly Ile Tyr Ala Thr Lys Met Lys Leu
            580                 585                 590

Gly Gly Ile Phe Ser Trp Ser Gly Asp Gln Asp Asp Gly Leu Leu Ala
            595                 600                 605

Asn Ala Ala His Glu Gly Leu Gly Tyr Leu Pro Val Arg Gly Lys Glu
        610                 615                 620

Lys Ile Asp Met Gly Pro Leu Tyr Asn Lys Gly Arg Leu Ile Gln Leu
625                 630                 635                 640

Pro Lys Val Thr Arg Arg Lys Ser
                645
```

XENORHABDUS TC GENE FOR PEST CONTROL

CROSS-REFERENCE TO RELATED APPLICATIONS

This application claims priority to provisional application Ser. No. 60/441,717, filed Jan. 21, 2003.

BACKGROUND OF THE INVENTION

Insects and other pests cost farmers billions of dollars annually in crop losses and in the expense of keeping these pests under control. The losses caused by insect pests in agricultural production environments include decreases in crop yield, reduced crop quality, and increased harvesting costs. Insect pests are also a burden to vegetable and fruit growers, to producers of ornamental flowers, and to home gardeners and homeowners.

Cultivation methods, such as crop rotation and the application of high levels of nitrogen fertilizers, have partially addressed problems caused by agricultural pests. However, various demands on the utilization of farmland restrict the use of crop rotation. In addition, overwintering traits of some insects are disrupting crop rotations in some areas.

Thus, synthetic chemical insecticides are relied upon most heavily to achieve a sufficient level of control. However, the use of synthetic chemical insecticides has several drawbacks. For example, the use of these chemicals can adversely affect many beneficial insects. Target insects have also developed resistance to some chemical pesticides. Furthermore, rain and improper calibration of insecticide application equipment can result in poor control. The use of insecticides often raises environmental concerns such as contamination of soil and water supplies when not used properly, and residues can also remain on treated fruits and vegetables. Working with some insecticides can also pose hazards to the persons applying them. Stringent new restrictions on the use of pesticides and the elimination of some effective pesticides could limit effective options for controlling damaging and costly pests.

The replacement of synthetic chemical pesticides, or combination of these agents with biological pesticides, could reduce the levels of toxic chemicals in the environment. Some biological pesticidal agents that are now being used with some success are derived from the soil microbe *Bacillus thuringiensis* (B.t.). While most B.t. strains do not exhibit pesticidal activity, some B.t. strains produce proteins that are highly toxic to pests, such as insects, and are specific in their toxic activity. Genes that encode δ-endotoxin proteins have been isolated. Other species of *Bacillus* also produce pesticidal proteins.

Höfte and Whiteley classified B.t. crystal proteins into four major classes (Höfte, H., H. R. Whiteley [1989]*Microbiological Reviews* 52(2):242–255). The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. For example, CryV and CryVI have been proposed to designate a class of toxin genes that are nematode-specific.

The 1989 nomenclature and classification scheme of Höfte and Whiteley for crystal proteins was based on both the deduced amino acid sequence and the activity spectrum of the toxin. That system was adapted to cover 14 different types of toxin genes divided into five major classes. The 1989 nomenclature scheme became unworkable as more and more genes were discovered that encoded proteins with varying spectrums of pesticidal activity. Thus, a revised nomenclature scheme was adopted, which is based solely on amino acid identity (Crickmore et al., 1998, *Microbiology and Molecular Biology Reviews* 62:807–813).

Recombinant DNA-based B.t. products have been produced and approved for use. In addition, with the use of genetic engineering techniques, various approaches for delivering these toxins to agricultural environments are being perfected. These include the use of plants genetically engineered with toxin genes for insect resistance and the use of stabilized intact microbial cells as toxin delivery vehicles. Thus, isolated *Bacillus* toxin genes are becoming commercially valuable.

B.t. protein toxins were initially formulated as sprayable insect control agents. A relatively more recent application of B.t. technology has been to isolate and transform plants with genes that encode these toxins. Transgenic plants subsequently produce the toxins, thereby providing insect control. See U.S. Pat. Nos. 5,380,831; 5,567,600; and 5,567,862 to Mycogen Corporation. Transgenic B.t. plants are quite efficacious, and usage is predicted to be high in some crops and areas.

There are some obstacles to the successful agricultural use of *Bacillus* (and other biological) pesticidal proteins. Certain insects can be refractory to the effects of *Bacillus* toxins. Insects such as boll weevils, black cutworm, and *Helicoverpa zea*, as well as adult insects of most species, heretofore have demonstrated no significant sensitivity to many B.t. δ-endotoxins.

Another potential obstacle is the development of resistance to B.t. toxins by insects. The potential for wide-spread use of B.t. plants has caused some concern that resistance management issues may arise more quickly than with traditional sprayable applications. While a number of insects have been selected for resistance to B.t. toxins in the laboratory, only the diamondback moth (*Plutella xylostella*) has demonstrated resistance in a field setting (Ferre, J. and Van Rie, J., *Annu. Rev. Entomol.* 47:501–533, 2002).

Resistance management strategies in B.t. transgene plant technology have become of great interest. Several strategies have been suggested for preserving the ability to effectively use *B. thuringiensis* toxins. These strategies include high dose with refuge, and alternation with, or co-deployment of, different toxins (McGaughey et al. (1998), "B.t. Resistance Management," *Nature Biotechnol.* 16:144–146), as in a natural bacterium, for example.

Thus, there remains a great need for developing additional genes that can be expressed in plants in order to effectively control various insects. In addition to continually trying to discover new B.t. toxins (which is becoming increasingly difficult due to the numerous B.t. toxins that have already been discovered), it would be quite desirable to discover other bacterial sources (distinct from B.t.) that produce toxins that could be used in transgenic plant strategies.

The relatively more recent efforts to clone insecticidal toxin genes from the *Photorhabdus/Xenorhabdus* group of bacteria present potential alternatives to toxins derived from *B. thuringiensis*. The genus *Xenorhabdus* is taxonomically defined as a member of the Family Enterobacteriaceae, although it has certain traits atypical of this family. For example, strains of this genus are typically nitrate reduction negative and catalase negative. *Xenorhabdus* has only recently been subdivided to create a second genus, *Photorhabdus*, which is comprised of the single species *Photorhabdus luminescens* (previously *Xenorhabdus luminescens*) (Boemare et al., 1993*Int. J. Syst. Bacteriol.* 43, 249–255). This differentiation is based on several distinguishing characteristics easily identifiable by the skilled artisan. These differences include the following: DNA-DNA characterization studies; phenotypic presence (*Photorhabdus*) or absence (*Xenorhabdus*) of catalase activity; presence (*Photorhabdus*) or absence (*Xenorhabdus*) of bioluminescence; the Family of the nematode host in that *Xenorhabdus* is found in Steinernematidae and *Photorhabdus* is found in Heterorhabditidae); as well as comparative, cellular fatty-acid analyses (Janse et al. 1990, *Lett. Appl. Microbiol.* 10, 131–135; Suzuki et al. 1990, *J. Gen. Appl. Microbiol.*, 36, 393–401). In addition, recent molecular studies focused on sequence (Rainey et al. 1995, *Int. J. Syst. Bacteriol.*, 45, 379–381) and restriction analysis (Brunel et al., 1997, *App. Environ. Micro.*, 63, 574–580) of 16S rRNA genes also support the separation of these two genera.

The expected traits for *Xenorhabdus* are the following: Gram stain negative rods, white to yellow/brown colony pigmentation, presence of inclusion bodies, absence of catalase, inability to reduce nitrate, absence of bioluminescence, ability to uptake dye from medium, positive gelatin hydrolysis, growth on Enterobacteriaceae selective media, growth temperature below 37° C., survival under anaerobic conditions, and motility.

Currently, the bacterial genus *Xenorhabdus* is comprised of four recognized species, *Xenorhabdus nematophilus*, *Xenorhabdus poinarii*, *Xenorhabdus bovienii* and *Xenorhabdus beddingii* (Brunel et al., 1997, *App. Environ. Micro.*, 63, 574–580). A variety of related strains have been described in the literature (e.g., Akhurst and Boemare 1988 *J. Gen. Microbiol.*, 134, 1835–1845; Boemare et al. 1993 *Int. J. Syst. Bacteriol.* 43, pp. 249–255; Putz et al. 1990, *Appl. Environ. Microbiol.*, 56,181–186, Brunel et al., 1997, *App. Environ. Micro.*, 63,574–580, Rainey et al. 1995, *Int. J. Syst. Bacteriol.*, 45, 379–381).

*Photorhabdus* and *Xenorhabdus* spp. are Gram-negative bacteria that entomopathogenically and symbiotically associate with soil nematodes. These bacteria are found in the gut of entomopathogenic nematodes that invade and kill insects. When the nematode invades an insect host, the bacteria are released into the insect haemocoel (the open circulatory system), and both the bacteria and the nematode undergo multiple rounds of replication; the insect host typically dies. These bacteria can be cultured away from their nematode hosts. For a more detailed discussion of these bacteria, see Forst and Nealson, 60 *Microbiol. Rev.* 1 (1996), pp. 21–43. Unfortunately, as reported in a number of articles, the bacteria only had pesticidal activity when injected into insect larvae and did not exhibit biological activity when delivered orally.

*Xenorhabdus* and *Photorhabus* bacteria secrete a wide variety of substances into the culture medium. See R. H. ffrench-Constant et al. 66 AEM No. 8, pp. 3310–3329 (August 2000), for a review of various factors involved in *Photorhabdus* virulence of insects.

It has been difficult to effectively exploit the insecticidal properties of the nematode or its bacterial symbiont. Thus, proteinaceous agents from *Photorhabdus/Xenorhabdus* bacteria that have oral activity are desirable so that the products produced therefrom could be formulated as a sprayable insecticide, or the genes encoding said proteinaceous agents could be isolated and used in the production of transgenic plants.

There has been substantial progress in the cloning of genes encoding insecticidal toxins from both *Photorhabdus luminescens* and *Xenorhabdus nematophilus*. Toxin-complex encoding genes from *P. luminescens* were examined first. See WO 98/08932. Parallel genes were more recently cloned from *X. nematophilus*. Morgan et al., *Applied and Environmental Microbiology* 2001, 67:20062–69. WO 95/00647 relates to the use of *Xenorhabdus* protein toxin to control insects, but it does not recognize orally active toxins. WO 98/08388 relates to orally administered pesticidal agents from *Xenorhabdus*. U.S. Pat. No. 6,048,838 relates to protein toxins/toxin complexes, having oral activity, obtainable from *Xenorhabdus* species and strains.

Four different toxin complexes (TCs)—Tca, Tcb, Tcc and Tcd—have been identified in *Photorhabdus* spp. Each of these toxin complexes resolves as either a single or dimeric species on a native agarose gel but resolution on a denaturing gel reveals that each complex consists of a range of species between 25–280 kDa. The ORFs that encode the typical TCs from *Photorhabdus*, together with protease cleavage sites (vertical arrows), are illustrated in FIG. 5. See also R. H. ffrench-Constant and Bowen, 57 *Cell. Mol. Life Sci.* 828–833 (2000).

Genomic libraries of *P. luminescens* were screened with DNA probes and with monoclonal and/or polyclonal antibodies raised against the toxins. Four tc loci were cloned: tca, tcb, tcc and tcd. The tca locus is a putative operon of three open reading frames (ORFs), tcaA, tcaB, and tcaC, transcribed from the same DNA strand, with a smaller terminal ORF (tcaZ) transcribed in the opposite direction. The tcc locus also is comprised of three ORFs putatively transcribed in the same direction (tccA, tccB, and tccc). The tcb locus is a single large ORF (tcbA), and the tcd locus is composed of two ORFs (tcdA and tcdB); tcbA and tcdA, each about 7.5 kb, encode large insect toxins. TcdB has some level of homology to TcaC. It was determined that many of these gene products were cleaved by proteases. For example, both TcbA and TcdA are cleaved into three fragments termed i, ii and iii (e.g. TcbAi, TcbAii and TcbAiii). Products of the tca and tcc ORFs are also cleaved. See FIG. 5. See also R. H. ffrench-Constant and D. J. Bowen, *Current Opinions in Microbiology*, 1999, 12:284–288.

Bioassays of the Tca toxin complexes revealed them to be highly toxic to first instar tomato hornworms (*Manduca sexta*) when given orally ($LD_{50}$ of 875 ng per square centimeter of artificial diet). R. H. ffrench-Constant and Bowen 1999. Feeding was inhibited at Tca doses as low as 40 ng/cm$^2$. Given the high predicted molecular weight of Tca, on a molar basis, *P. luminescens* toxins are highly active and relatively few molecules appear to be necessary to exert a toxic effect. R. H. ffrench-Constant and Bowen, *Current Opinions in Micriobiology*, 1999, 12:284–288.

None of the four loci showed overall similarity to any sequences of known function in GenBank. Regions of sequence similarity raised some suggestion that these proteins (TcaC and TccA) may overcome insect immunity by attacking insect hemocytes. R. H. ffrench-Constant and Bowen, *Current Opinions in Microbiology*, 1999, 12:284–288.

TcaB, TcbA and TcdA all show amino acid conservation (~50% identity), compared with each other, immediately around their predicted protease cleavage sites. This conservation between three different Tc proteins suggests that they may all be processed by the same or similar proteases. TcbA and TcdA also share ~50% identity overall, as well as a similar predicted pattern of both carboxy- and amino-terminal cleavage. It was postulated that these proteins might thus be homologs of one another. Furthermore, the similar, large size of TcbA and TcdA, and also the fact that both toxins appear to act on the gut of the insect, may suggest similar modes of action. R. H. ffrench-Constant and Bowen, *Current Opinions in Microbiology*, 1999, 12:284–288.

Deletion/knock-out studies suggest that products of the tca and tcd loci account for the majority of oral toxicity to lepidopterans. Deletion of either of the tca or tcd genes greatly reduced oral activity against *Manduca sexta*. That is, products of the tca and tcd loci are oral lepidopteran toxins on their own; their combined effect contributed most of the secreted oral activity. R. H. ffrench-Constant and D. J. Bowen, 57 *Cell. Mol. Life. Sci.* 831 (2000). Interestingly, deletion of either of the tcb or tcc loci alone also reduces mortality, suggesting that there may be complex interactions among the different gene products. Thus, products of the tca locus may enhance the toxicity of tcd products. Alternatively, tcd products may modulate the toxicity of tca products and possibly other complexes. Noting that the above relates to oral activity against a single insect species, tcb or tcc loci may produce toxins that are more active against other groups of insects (or active via injection directly into the insect haemocoel—the normal route of delivery when secreted by the bacteria in vivo). R. H. ffrench-Constant and Bowen, *Current Opinions in Microbiology,* 1999, 12:284–288.

The insect midgut epithelium contains both columnar (structural) and goblet (secretory) cells. Ingestion of tca products by M sexta leads to apical swelling and blebbing of large cytoplasmic vesicles by the columnar cells, leading to the eventual extrusion of cell nuclei in vesicles into the gut lumen. Goblet cells are also apparently affected in the same fashion. Products of tca act on the insect midgut following either oral delivery or injection. R. H. ffrench-Constant and D. J. Bowen, *Current Opinions in Microbiology,* 1999, 12:284–288. Purified tca products have shown oral toxicity against *Manduca sexta* ($LD_{50}$ of 875 ng/cm$^2$). R. H. ffrench-Constant and D. J. Bowen, 57 *Cell. Mol. Life Sci.* 828–833 (2000).

WO 99/42589 and U.S. Pat. No. 6,281,413 disclose TC-like ORFs from *Photorhabdus luminescens*. WO 00/30453 and WO 00/42855 disclose TC-like proteins from *Xenorhabdus*. WO 99/03328 and WO 99/54472 (and U.S. Pat. Nos. 6,174,860 and 6,277,823) relate to other toxins from *Xenorhabdus* and *Photorhabdus*.

While the exact molecular interactions of the TCs with each other, and their mechanism(s) of action, are not currently understood, it is known, for example, that the Tca toxin complex of *Photorhabdus* is toxic to *Manduca sexta*. In addition, some TC proteins are known to have "stand alone" insecticidal activity, while other TC proteins are known to potentiate or enhance the activity of the stand-alone toxins. It is known that the TcdA protein is active, alone, against *Manduca sexta*, but that TcdB and TccC, together, can be used (in conjunction with TcdA) to greatly enhance the activity of TcdA. TcbA is the other main, stand-alone toxin from *Photorhabdus*. The activity of this toxin (TcbA) can also be greatly enhanced by TcdB- together with TccC-like proteins.

| Photorhabdus TC protein | Photorhabdus strain W14 nomenclature | Some homology to: |
|---|---|---|
| TcaA | Toxin C | TccA |
| TcaB | | TccB |
| TcaC | | TcdB |
| Tcb | Toxin B | |
| TccA | Toxin D | TcdA N terminus |
| TccB | | TcdA C terminus |
| TccC | | |
| TcdA | Toxin A | TccA + TccB |
| TcdB | | TcaC |

Some *Photorhabdus* TC proteins have some level of sequence homology with other *Photorhabdus* TC proteins. As indicated above, TccA has some level of homology with the N terminus of TcdA, and TccB has some level of homology with the C terminus of TcdA. Furthermore, TcdA is about 280 kDa, and TccA together with TccB are of about the same size, if combined, as that of TcdA. Though TccA and TccB are much less active on SCR than TcdA, TccA and TccB from *Photorhabdus* strain W14 are called "Toxin D." "Toxin A" (TcdA), "Toxin B" (Tcb or TcbA), and "Toxin C" (TcaA and TcaB) are also indicated above.

Furthermore, TcaA has some level of homology with TccA and likewise with the N terminus of TcdA. Still further, TcaB has some level of homology with TccB and likewise with the N terminus of TcdA. TcdB has a significant level of similarity to TcaC.

Relatively recent cloning efforts in *Xenorhabdus nematophilus* also appear to have identified novel insecticidal toxin genes with homology to the *P. luminescens* tc loci. See, e.g., WO 98/08388 and Morgan et al., *Applied and Environmental Microbiology* 2001, 67:20062–69. In R. H. ffrench-Constant and D. J. Bowen *Current Opinions in Micriobiology,* 1999,12:284–288, cosmid clones were screened directly for oral toxicity to another lepidopteran, Pieris brassicae. One orally toxic cosmid clone was sequenced. Analysis of the sequence in that cosmid suggested that there are five different ORF's with similarity to *Photorhabdus* tc genes; orf2 and orf5 both have some level of sequence relatedness to both tcbA and tcdA, whereas orf1 is similar to tccB, orf3 is similar to tccC and orf4 is similar to tca C. Importantly, a number of these predicted ORFs also share the putative cleavage site documented in *P. luminescens*, suggesting that active toxins may also be protealytically processed.

There are five typical *Xenorhabdus* TC proteins: XptA1, XptA2, XptB1, XptC1, and XptD1. XptA1 is a "stand-alone" toxin. XptA2 is the other TC protein from *Xenorhabdus* that has stand-alone toxin activity. XptB1 and XptC1 are the *Xenorhabdus* potentiators that can enhance the activity of either (or both) of the XptA toxins. XptD1 has some level of homology with TccB.

XptC1 was known to have some level of similarity to TcaC. The XptA2 protein of *Xenorhabdus* was known to have some degree of similarity to the TcdA protein. XptB 1 has some level of similarity to TccC.

The finding of somewhat similar, toxin-encoding loci in these two different bacteria is interesting in terms of the possible origins of these virulence genes. The *X. nematophilus* cosmid also appears to contain transposase-like sequences whose presence may suggest that these loci can be transferred horizontally between different strains or species of bacteria. A range of such transfer events may also explain the apparently different genomic organization of the tc operons in the two different bacteria. Further, only a subset of *X. nematophilus* and *P. luminescens* strains appear toxic to *M. sexta*, suggesting either that different strains lack the tc genes or that they carry a different tc gene compliment. Detailed analysis of both a strain and toxin phylogeny within, and between, these bacterial species should help clarify the likely origin of the toxin genes and how they are maintained in different bacterial populations. R. H. ffrench-Constant and Bowen, *Current Opinions in Microbiology*, 1999, 12:284–288.

TC proteins and genes have more recently been described from other insect-associated bacteria such as *Serratia entomophila*, an insect pathogen. Waterfield et al., *TRENDS in Microbiology*, Vol. 9, No. 4, April 2001.

In summary, toxin complex proteins from *P. luminescens* and *X. nematophilus* appear to have little homology to previously identified bacterial toxins and should provide useful alternatives to toxins derived from *B. thuringiensis*. Although they have similar toxic effects on the insect midgut to other orally active toxins, their precise mode of action remains obscure. Future work could clarify their mechanism of action.

Bacteria of the genus *Paenibacillus* are distinguishable from other bacteria by distinctive rRNA and phenotypic characteristics (C. Ash et al. (1993), "Molecular identification of rRNA group 3 bacilli (Ash, Farrow, Wallbanks and Collins) using a PCR probe test: Proposal for the creation of a new genus *Paenibacillus*," *Antonie Van Leeuwenhoek* 64:253–260). Some species in this genusare known to be pathogenic to honeybees (*Paenibacillus larvae*) and to scarab beetle grubs (*P. popilliae* and *P. lentimorbus*.) *P. larvae, P. popilliae,* and *P. lentimorbus* are considered obligate insect pathogens involved with milky disease of scarab beetles (D. P. Stahly et al. (1992), "The genus *Bacillus*: insect pathogens," p. 1697–1745, In A. Balows et al., ed., *The Procaryotes*, $2^{nd}$ Ed., Vol. 2, Springer-Verlag, New York, N.Y.).

A crystal protein, Cry18, has been identified in strains of *P. popilliae* and *P. lentimorbus*. Cry18 has scarab and grub toxicity, and has about 40% identity to Cry2 proteins (Zhang et al., 1997; Harrison et al., 2000).

TC proteins and lepidopteran-toxic Cry proteins have very recently been discovered in *Paenibacillus*. See U.S. Ser. No. 60/392,633 (Bintrim et al.), filed Jun. 28, 2002.

Although some *Xenorhabdus* TC proteins were found to "correspond" (have a similar function and some level of sequence homology) to some of the *Photorhabdus* TC proteins, the "corresponding" proteins share only about 40% (approximately) sequence identity with each other. This is also true for the more recently discovered TC proteins from *Paenibacillus* (those proteins and that discovery are the subject of co-pending U.S. Ser. No. 60/392,633).

In light of concerns about insects developing resistance to a given pesticidal toxin, and in light of other concerns— some of which are discussed above, there is a continuing need for the discovery of new insecticidal toxins and other proteins that can be used to control insects.

BRIEF SUMMARY OF THE INVENTION

The subject invention relates to novel *Xenorhabdus* toxin complex (TC) proteins and genes that encode these proteins. More specifically, the subject invention relates to TC proteins and genes obtainable from *Xenorhabdus* strain Xwi.

The subject invention also provides an exochitinase obtainable from the Xwi strain. This exochitinase can be used to control insects using methods known in the art.

BRIEF DESCRIPTION OF THE FIGURES

FIG. 5 shows the TC operon from *Photorhabdus*.

BRIEF DESCRIPTION OF THE SEQUENCES

Figure 1:
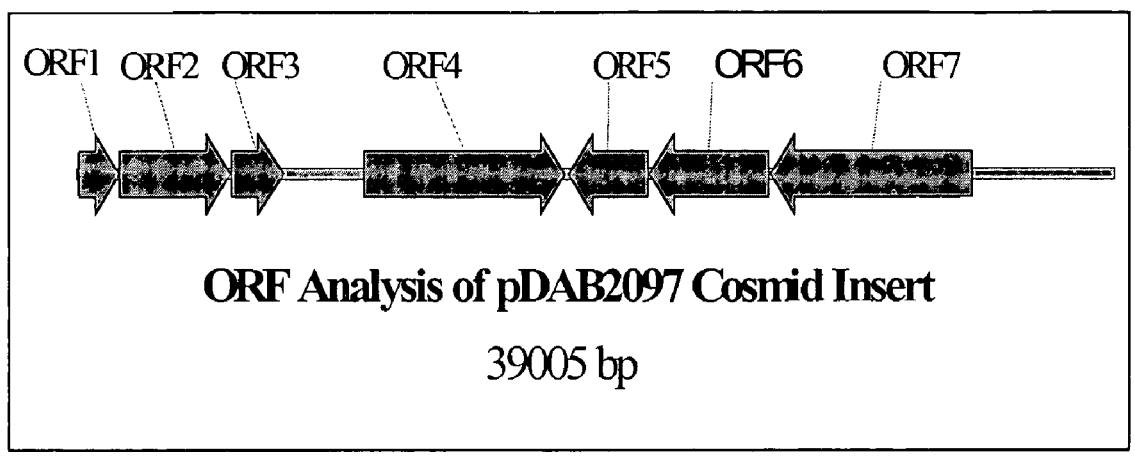
FIG. 1 shows the orientation of ORFs identified in pDAB2097.

SEQ ID NO:1 is the N-terminus of $Toxin_{XwiA}$ 220 kDa protein.
SEQ ID NO:2 is an internal peptide of $Toxin_{XwiA}$ purified toxin.
SEQ ID NO:3 is an internal peptide of $Toxin_{XwiA}$ purified toxin.
SEQ ID NO:4 is an internal peptide of $Toxin_{XwiA}$ purified toxin.
SEQ ID NO:5 is an internal peptide of $Toxin_{XwiA}$ purified toxin.
SEQ ID NO:6 is the pDAB2097 cosmid insert: 39,005 bp.
SEQ ID NO:7 is the pDAB2097 cosmid ORF1: nucleotides 1–1,533 of SEQ ID NO:6.
SEQ ID NO:8 is the pDAB2097 cosmid ORF1 deduced protein: 511 aa.
SEQ ID NO:9 is the pDAB2097 cosmid ORF2 (xptD1): nucleotides 1,543–5,715 of SEQ ID NO:6.
SEQ ID NO:10 is the pDAB2097 cosmid ORF2 deduced protein: 1,391 aa.
SEQ ID NO:11 is the pDAB2097 cosmid ORF3: nucleotides 5,764–7,707 of SEQ ID NO:6.
SEQ ID NO:12 is the pDAB2097 cosmid ORF3 deduced protein: 648 aa.
SEQ ID NO:13 is the pDAB2097 cosmid ORF4 (xptA1): nucleotides 10,709–18,277 of SEQ ID NO:6.
SEQ ID NO:14 is the pDAB2097 cosmid ORF4 deduced protein: 2,523 aa.
SEQ ID NO:15 is the pDAB2097 cosmid ORF5 (xptB1): nucleotides 18,383–21,430 (C) of SEQ ID NO:6.
SEQ ID NO:16 is the pDAB2097 cosmid ORF5 deduced protein: 1,016 aa.
SEQ ID NO:17 is the pDAB2097 cosmid ORF6 (xptC1): nucleotides 21,487–25,965 (C) of SEQ ID NO:6.
SEQ ID NO:18 is the pDAB2097 cosmid ORF6 deduced protein: 1,493 aa.
SEQ ID NO:19 is the pDAB2097 cosmid ORF7 (xptA2): nucleotides 26,021–33,634 (C) of SEQ ID NO:6.
SEQ ID NO:20 is the pDAB2097 cosmid ORF7 deduced protein: 2,538 aa.
SEQ ID NO:21 is the nucleotide sequence of the pDAB2097 cosmid insert that encodes an exochitinase.
SEQ ID NO:22 is the amino acid sequence of the exochitinase encodes by SEQ ID NO:21.
SEQ ID NO:23 is the deduced amino acid sequence from XptA2, residue numbers 0016–0034.
SEQ ID NO:24 is the deduced amino acid sequence from XptA2, residue numbers 0035–0047.
SEQ ID NO:25 is the deduced amino acid sequence from XptA2, residue numbers 0036–0047.
SEQ ID NO:26 is the deduced amino acid sequence from XptA2, residue numbers 0048–0057.
SEQ ID NO:27 is the deduced amino acid sequence from XptA2, residue numbers 0071–0080.
SEQ ID NO:28 is the deduced amino acid sequence from XptA2, residue numbers 009 1–0099.

SEQ ID NO:29 is the deduced amino acid sequence from XptA2, residue numbers 0100–0124.
SEQ ID NO:30 is the deduced amino acid sequence from XptA2, residue numbers 0128–0141.
SEQ ID NO:31 is the deduced amino acid sequence from XptA2, residue numbers 0 194–0208.
SEQ ID NO:32 is the deduced amino acid sequence from XptA2, residue numbers 0209–0223.
SEQ ID NO:33 is the deduced amino acid sequence from XptA2, residue numbers 0369–0375.
SEQ ID NO:34 is the deduced amino acid sequence from XptA2, residue numbers 0416–0420.
SEQ ID NO:35 is the deduced amino acid sequence from XptA2, residue numbers 0487–0496.
SEQ ID NO:36 is the deduced amino acid sequence from XptA2, residue numbers 0537–0558.
SEQ ID NO:37 is the deduced amino acid sequence from XptA2, residue numbers 0628–0639.
SEQ ID NO:38 is the deduced amino acid sequence from XptA2, residue numbers 0797–0813.
SEQ ID NO:39 is the deduced amino acid sequence from XptA2, residue numbers 0893–0898.
SEQ ID NO:40 is the deduced amino acid sequence from XptA2, residue numbers 0987–1000.
SEQ ID NO:41 is the deduced amino acid sequence from XptA2, residue numbers 1017–1027.
SEQ ID NO:42 is the deduced amino acid sequence from XptA2, residue numbers 1028–1036.
SEQ ID NO:43 is the deduced amino acid sequence from XptA2, residue numbers 1037–1050.
SEQ ID NO:44 is the deduced amino acid sequence from XptA2, residue numbers 1080–1092.
SEQ ID NO:45 is the deduced amino acid sequence from XptA2, residue numbers 1093–1115.
SEQ ID NO:46 is the deduced amino acid sequence from XptA2, residue numbers 1116–1124.
SEQ ID NO:47 is the deduced amino acid sequence from XptA2, residue numbers 1143–1166.
SEQ ID NO:48 is the deduced amino acid sequence from XptA2, residue numbers 1165–1179.
SEQ ID NO:49 is the deduced amino acid sequence from XptA2, residue numbers 1195–1199.
SEQ ID NO:50 is the deduced amino acid sequence from XptA2, residue numbers 1277–1284.
SEQ ID NO:51 is the deduced amino acid sequence from XptA2, residue numbers 1290–1304.
SEQ ID NO:52 is the deduced amino acid sequence from XptA2, residue numbers 1346–1363.
SEQ ID NO:53 is the deduced amino acid sequence from XptA2, residue numbers 1364–1372.
SEQ ID NO:54 is the deduced amino acid sequence from XptA2, residue numbers 1421–1437.
SEQ ID NO:55 is the deduced amino acid sequence from XptA2, residue numbers 1438–1451.
SEQ ID NO:56 is the deduced amino acid sequence from XptA2, residue numbers 1593–1605.
SEQ ID NO:57 is the deduced amino acid sequence from XptA2, residue numbers 1594–1605.
SEQ ID NO:58 is the deduced amino acid sequence from XptA2, residue numbers 1606–1620.
SEQ ID NO:59 is the deduced amino acid sequence from XptA2, residue numbers 1635–1649.
SEQ ID NO:60 is the deduced amino acid sequence from XptA2, residue numbers 1668–1677.
SEQ ID NO:61 is the deduced amino acid sequence from XptA2, residue numbers 1681–1692.
SEQ ID NO:62 is the deduced amino acid sequence from XptA2, residue numbers 1885–1890.
SEQ ID NO:63 is the deduced amino acid sequence from XptA2, residue numbers 1891–1898.
SEQ ID NO:64 is the deduced amino acid sequence from XptA2, residue numbers 1999–2003.
SEQ ID NO:65 is the deduced amino acid sequence from XptA2, residue numbers 2026–2050.
SEQ ID NO:66 is the deduced amino acid sequence from XptA2, residue numbers 2051–2057.
SEQ ID NO:67 is the deduced amino acid sequence from XptA2, residue numbers 2106–2121.
SEQ ID NO:68 is the deduced amino acid sequence from XptA2, residue numbers 2131–2145.
SEQ ID NO:69 is the deduced amino acid sequence from XptA2, residue numbers 2186–2191.
SEQ ID NO:70 is the deduced amino acid sequence from XptA2, residue numbers 2220–2228.
SEQ ID NO:71 is the deduced amino acid sequence from XptA2, residue numbers 2221–2228.
SEQ ID NO:72 is the deduced amino acid sequence from XptA2, residue numbers 2222–2228.
SEQ ID NO:73 is the deduced amino acid sequence from XptA2, residue numbers 2281–2287.
SEQ ID NO:74 is the deduced amino acid sequence from XptA2, residue numbers 2315–2325.
SEQ ID NO:75 is the deduced amino acid sequence from XptA2, residue numbers 2352–2359.
SEQ ID NO:76 is the deduced amino acid sequence from XptA2, residue numbers 2387–2392.
SEQ ID NO:77 is the deduced amino acid sequence from XptA2, residue numbers 2423–2435.
SEQ ID NO:78 is the deduced amino acid sequence from XptA2, residue numbers 2439–2455.
SEQ ID NO:79 is the deduced amino acid sequence from XptA2, residue numbers 2456–2468.
SEQ ID NO:80 is a forward primer sequence used to amplify XptA2.
SEQ ID NO:81 is a reverse primer sequence used to amplify XptA2.
SEQ ID NO:82 is a forward primer sequence used to amplify XptC1.
SEQ ID NO:83 is a reverse primer sequence used to amplify XptC1.
SEQ ID NO:84 is a forward primer sequence used to amplify XptB1.
SEQ ID NO:85 is a reverse primer sequence used to amplify XptB1.

DETAILED DESCRIPTION OF THE INVENTION

The subject invention relates to novel *Xenorhabdus* toxin complex (TC) proteins and genes that encode these proteins. More specifically, the subject invention relates to TC genes and proteins obtainable from *Xenorhabdus* strain Xwi.

The subject invention also provides an exochitinase obtainable from the Xwi strain. This exochitinase can be used to control insects using methods known in the art. See, e.g., U.S. Pat. No. 5,173,419. The polynucleotide of SEQ ID NO:21 can be inserted into the genome of a plant so that the plant produces the protein of SEQ ID NO:22. Insects consuming the plant tissues that produce (and contain) this protein thereby contact the protein and will be controlled in this manner. The TC protein genes can be used in similar manners (i.e., expression in plants) to control insects and other like pests. Preferably, a plant is produced that expresses the XptA1 and/or XptA2 gene of SEQ ID NOs:13 and 19 so that the subject XptA1 and/or XptA2 toxin proteins of the subject invention are produced by and preferably present in the cells of the plant. The plant can be constructed to co-express the XptC1 and XptB1 genes of SEQ ID NOs:17 and 15, respectively, so that the XptC1 and XptB1 proteins potentiate or enhance the XptA1 and/or XptA2 TC protein toxins. The XptD1 gene of the subject invention can also be used, similarly, as would be known in the art.

Other methods of administering the subject proteins to insects and other pests are well known in the art. Furthermore, the subject proteins are not limited to use with each other; they can be used individually (or in combination) with other proteins, as would be known in the art.

Proteins and toxins. The present invention provides easily administered, functional proteins. The present invention also provides a method for delivering insecticidal toxins that are functionally active and effective against many orders of insects, preferably lepidopteran insects. By "functional activity" (or "active against") it is meant herein that the protein toxins function as orally active insect control agents (alone or in combination with other proteins), that the proteins have a toxic effect (alone or in combination with other proteins), or are able to disrupt or deter insect- growth and/or feeding which may or may not cause death of the insect. When an insect comes into contact with an effective amount of a "toxin" of the subject invention delivered via transgenic plant expression, formulated protein composition(s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Functional proteins of the subject invention can also work together or alone to enhance or improve the activity of one or more other toxin proteins. The terms "toxic," "toxicity," or "toxin" as used herein are meant to convey that the subject "toxins" have "functional activity" as defined herein.

Complete lethality to feeding insects is preferred but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

There are many other ways in which toxins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding toxins can be transferred to plant material so that said plant material expresses the toxin of interest.

Transfer of the functional activity to plant or bacterial systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the bacterial species which produce the toxins, using information deduced from the toxin's amino acid sequence, as disclosed herein. The native sequences can be optimized for expression in plants, for example, as discussed in more detail below. Optimized polynucleotide can also be designed based on the protein sequence.

The subject invention provides new classes of toxins having advantageous pesticidal activities. One way to characterize these classes of toxins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining the pesticidal toxins of the instant invention.

For example, antibodies to the pesticidal toxins disclosed and claimed herein can be used to identify and isolate other toxins from a mixture of proteins. Specifically, antibodies may be raised to the portions of the toxins which are most constant and most distinct from other toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or to fragments of these toxins, can be readily prepared using standard procedures. Toxins of the subject invention can be obtained from a variety of sources/source microorganisms.

One skilled in the art would readily recognize that toxins (and genes) of the subject invention can be obtained from a variety of sources. A toxin "from" or "obtainable from" the subject Xwi isolate means that the toxin (or a similar toxin) can be obtained from Xwi or some other source, such as another bacterial strain or a plant. For example, one skilled in the art will readily recognize that, given the disclosure of a bacterial gene and toxin, a plant can be engineered to produce the toxin. Antibody preparations, nucleic acid probes (DNA and RNA), and the like may be prepared using the polynucleotide and/or amino acid sequences disclosed herein and used to screen and recover other toxin genes from other (natural) sources.

Polynucleotides and probes. The subject invention further provides nucleotide sequences that encode the toxins of the subject invention. The subject invention further provides methods of identifying and characterizing genes that encode pesticidal toxins. In one embodiment, the subject invention provides unique nucleotide sequences that are useful as hybridization probes and/or primers for PCR techniques. The primers produce characteristic gene fragments that can be used in the identification, characterization, and/or isolation of specific toxin genes. The nucleotide sequences of the subject invention encode toxins that are distinct from previously described toxins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

Further aspects of the subject invention include genes and isolates identified using the methods and nucleotide sequences disclosed herein. The genes thus identified encode toxins active against pests.

Toxins and genes of the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "n" is used generically, "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169–170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water to 1 liter, followed by adjusting pH to 7.0 with 10 N NaOH. 10% SDS can be prepared by dissolving 10 g of SDS in 50 ml of autoclaved water, diluting to 100 ml, and aliquotting.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein.

As used herein "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes was performed by standard methods (see, e.g., Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266–285):

$Tm=81.5°$ C.$+16.6$ Log[Na+]$+0.41$(% $G+C$)$-0.61$(% formamide)$-600$/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

$Tm(°$ C.$)=2$(number $T/A$ base pairs)$+4$(number $G/C$ base pairs)

(Suggs, S. V., T. Miyake, E. H. Kawashime, M. J. Johnson, K. Itakura, and R. B. Wallace [1981] *ICA-UCLA Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| Low: | 1 or 2x SSPE, room temperature |
| --- | --- |
| Low: | 1 or 2x SSPE, 42° C. |
| Moderate: | 0.2x or 1x SSPE, 65° C. |
| High: | 0.1x SSPE, 65° C. |

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," Science 230:1350–1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium Thermus aquaticus, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of genes and toxins. The genes and toxins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof. Proteins of the subject invention can have substituted amino acids so long as they retain the characteristic pesticidal/functional activity of the proteins specifically exemplified herein. "Variant" genes have nucleotide sequences that encode the same toxins or equivalent toxins having pesticidal activity equivalent to an exemplified protein. The terms "variant proteins" and "equivalent toxins" refer to toxins having the same or essentially the same biological/functional activity against the target pests and equivalent sequences as the exemplified toxins. As used herein, reference to an "equivalent" sequence refers to sequences having amino acid substitutions, deletions, additions, or insertions which improve or do not adversely affect pesticidal activity. Fragments retaining pesticidal activity are also included in this definition. Fragments and other equivalents that retain the same or similar function, or "toxin activity," as a corresponding fragment of an exemplified toxin are within the scope of the subject invention. Changes, such as amino acid substitutions or additions, can be made for a variety of purposes, such as increasing (or decreasing) protease stability of the protein (without materially/substantially decreasing the functional activity of the toxin).

Equivalent toxins and/or genes encoding these equivalent toxins can be obtained/derived from wild-type or recombinant bacteria and/or from other wild-type or recombinant organisms using the teachings provided herein. Other Bacillus, Paenibacillus, Photorhabdus, and Xenorhabdus species, for example, can be used as source isolates.

Variations of genes may be readily constructed using standard techniques for making point mutations, for example. In addition, U.S. Pat. No.5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97,98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445; 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 contiguous residues (amino acid or nucleotide), corresponding to a segment (of the same size) in any of the exemplified sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

It is within the scope of the invention as disclosed herein that toxins may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as E. coli, baculoviruses, plant-based viral systems, yeast and the like and then placed in insect assays as disclosed herein to determine activity. It is well-known in the art that truncated toxins can be successfully produced so that they retain functional activity while having less than the entire, full-length sequence. It is well known in the art that B.t. toxins can be used in a truncated (core toxin) form. See, e.g., Adang et al., Gene 36:289–300 (1985), "Characterized full-length and truncated plasmid clones of the crystal protein of Bacillus thuringiensis subsp kurstaki HD-73 and their toxicity to Manduca sexta." There are other examples of truncated proteins that retain insecticidal activity, including the insect juvenile hormone esterase (U.S. Pat. No.5,674,485 to the Regents of the University of California). As used herein, the term "toxin" is also meant to include functionally active truncations.

Certain toxins of the subject invention have been specifically exemplified herein. As these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid similarity (and/or homology) with an exemplified toxin. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity and/or similarity of two nucleic acids is determined using the algorithm of Karlin and Altschul (1990), Proc. Natl. Acad. Sci. USA 87:2264–2268, modified as in Karlin and Altschul (1993), Proc. Natl. Acad. Sci. USA 90:5873–5877. Such an algorithm is incorporated into the NBLAST and XBLAST programs of Altschul et al. (1990), J. Mol. Biol. 215:402–410. BLAST nucleotide searches are performed with the NBLAST program, score=100, wordlength=12. To obtain gapped alignments for comparison purposes, Gapped BLAST is used as described in Altschul et al. (1997), Nucl. Acids Res. 25:3389–3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above.

The amino acid homology/similarity/identity will be highest in critical regions of the toxin which account for biological activity or are involved in the determination of three-dimensional configuration which is ultimately responsible for the biological activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and three-dimensional features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological activity of the toxin.

As used herein, reference to "isolated" polynucleotides and/or "purified" toxins refers to these molecules when they are not associated with the other molecules with which they would be found in nature. Thus, reference to "isolated" and/or "purified" signifies the involvement of the "hand of man" as described herein. For example, a bacterial toxin "gene" of the subject invention put into a plant for expression is an "isolated polynucleotide." Likewise, a *Xenorhabdus* protein, exemplified herein, produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Optimization of sequence for expression in plants. To obtain high expression of heterologous genes in plants it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial toxin is reengineering of a heterologous gene for optimal expression.

One reason for the reengineering of a bacterial toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial toxin for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial toxin is to generate a DNA sequence in which the sequence modifications do not hinder translation.

The table below (Table 2) illustrates how high the G+C content is in maize. For the data in Table 2, coding regions of the genes were extracted from GenBank (Release 71) entries, and base compositions were calculated using the MacVector.™ program (IBI, New Haven, Conn.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial toxin for maize (or other plant, such as cotton or soybean) expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined as well as the second and third choice of preferred codons. Afterwards, the amino acid sequence of the bacterial toxin of interest is reverse translated so that the resulting nucleic acid sequence codes for exactly the same protein as the native gene wanting to be heterologously expressed. The new DNA sequence is designed using codon bias information so that it corresponds to the most preferred codons of the desired plant. The new sequence is then analyzed for restriction enzyme sites that might have been created by the modification. The identified sites are further modified by replacing the codons with second or third choice preferred codons. Other sites in the sequence which could affect transcription or translation of the gene of interest are the exon intronjunctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 2

Compilation of G + C contents of protein coding regions of maize genes

| Protein Class.sup.a | Range % G + C | Mean % G + C.sup.b |
|---|---|---|
| Metabolic Enzymes (76) | 44.4–75.3 | 59.0 (. + –.8.0) |
| Structural Proteins (18) | 48.6–70.5 | 63.6 (. + –.6.7) |
| Regulatory Proteins (5) | 57.2–68.8 | 62.0 (. + –.4.9) |
| Uncharacterized Proteins (9) | 41.5–70.3 | 64.3 (. + –.7.2) |
| All Proteins (108) | 44.4–75.3 | 60.8 (. + –.5.2) |

.sup.a Number of genes in class given in parentheses.
.sup.b Standard deviations given in parentheses.
.sup.c Combined groups mean ignored in mean calculation It is preferred that the plant optimized gene(s) encoding a bacterial toxin contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3. The method described above enables one skilled in the art to modify gene(s) that are foreign to a particular plant so that the genes are optimally expressed in plants. The method is further illustrated in PCT application WO 97/13402.

In order to design plant optimized genes encoding a bacterial toxin, the amino acid sequence of said protein is reverse translated into a DNA sequence utilizing a non-redundant genetic code established from a codon bias table compiled for the gene sequences for the particular plant, as shown in Table 2. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

TABLE 3

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

In some cases, especially for expression in plants, it can be advantageous to use truncated genes that express truncated proteins. Höfte et al. 1989, for example, discussed in the Background Section above, discussed protoxin and core toxin segments of B.t. toxins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length toxin.

Transgenic hosts. The toxin-encoding genes of the subject invention can be introduced into a wide variety of microbial or plant hosts. In preferred embodiments, transgenic plant cells and plants are used. Preferred plants (and plant cells) are corn, maize, and cotton.

In preferred embodiments, expression of the toxin gene results, directly or indirectly, in the intracellular production (and maintenance) of the pesticide proteins. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest.

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobirum melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Also of interest are pigmented microorganisms.

Insertion of genes to form transgenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. Nos. 4,945,050 to Cornell and U.S. Pat. No. 5,141,131 to Dow-Elanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149, 645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plant can be transformed with a viral vector using the methods described in U.S. Pat. Nos. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980) 77:7347–7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the Agrobacteria are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17–19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B.t. toxins. One strategy for insect resistance management would be to combine the TC toxins produced by *Xenorhabdus, Photorhabdus*, and the like with toxins such as B.t. crystal toxins, soluble insecticidal proteins from *Bacillus* stains (see, e.g., WO 98/18932 and WO 99/57282), or other insect toxins. The combinations could be formulated for a sprayable application or could be molecular combinations. Plants could be transformed with bacterial genes that produce two or more different insect toxins (see, e.g., Gould, 38 *Bioscience* 26–33 (1988) and U.S. Pat. No. 5,500,365; likewise, European Patent Application 0 400 246 A1 and U.S. Pat. Nos. 5,866,784; 5,908,970; and 6,172,281 also describe transformation of a plant with two B.t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing spores and/or crystals of the subject *Paenibacillus* isolate, or recombinant microbes comprising the genes obtainable from the isolate disclosed herein, can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The affect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express bacterial toxin. In so doing, the gene encoding a toxin can be inserted into the coat promoter region of a suitable plant virus which will infect the host plant of interest. The toxin can then be expressed thus providing protection of the plant from insect damage. Plant RNA viral based systems are described in U.S. Pat. Nos. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it maybe desirable to reengineer the bacterial gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of the *Xenorhabdus* Xwi isolate of the invention can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Growth and Characterization of *Xenorhabdus* Strain Xwi

It was shown previously (U.S. Pat. No. 6,048,838) that *Xenorhabdus* strain Xwi (NRRL B-21733, deposited Apr. 29, 1997) produced extracellular proteins with oral insecticidal activity against members of the insect orders Coleoptera, Lepidoptera, Diptera, and Acarina. Full-length gene and TC protein sequences obtainable from strain Xwi are disclosed herein.

Production and processing of *Xenorhabdus* fermentation broths. *Xenorhabdus* strain Xwi was grown on 2% proteose peptone #3 (hereafter designated as PP3) agar containing 0.0025% bromthymol blue (20 g/L proteose peptone #3, 0.025 g/L bromthymol blue, 15 g/L Bacto agar; Difco Laboratories, Detroit, Mich.) for 72 hours at 28° C. Seed flasks were produced by inoculating single, bromthymol blue-adsorbing colony into a 500 mL tri-baffled flask containing 175 mL of sterile PP3 plus 1.25% NaCl. Following 16 hr incubation at 28° C. on a rotary shaker at 150 rpm, seed cultures were transferred into production flasks. Two mL of the seed culture was inoculated into each production flask, which was a 500 mL tri-baffled flask containing 175 mL of sterile PP3 plus 1.25% NaCl. Production flasks were incubated at 28° C. and shaken on a rotary shaker at 150 rpm. After incubation for 48–72 hrs, the production fermentation broths were pooled, dispensed into sterile 1.0 L polyethylene bottles, centrifuged at 2,400×g for 1 hr at 10° C., and decanted from the cell and debris pellet. The fermentation broth was then either filter sterilized through a 0.22 µM filter, or further clarified using a tangential flow microfiltration device (Pall Filtron, Northborough, Mass.) using a 0.5 µM open channel poly-ether sulfone membrane filter. The filter-sterilized fermentation broths were then used as the starting material for the biochemical fractionation and purification of proteins responsible for the insecticidal activities observed in these broths.

Insect bioassay of biochemically fractionated and purified protein samples. To aid in the purification and specific activity determination of *Xenorhabdus* proteins possessing insecticidal activity, biochemically fractionated protein samples and serially diluted purified protein preparations were tested in insect feeding bioassays. The insect species used in these assays included *Diabrotica undecimpunctata howardi* (Barber) (southern corn rootworm, SCR), *Helicoverpa zea* (Boddie) (corn earworm, CEW), *Heliothis virescens* (Fabricius) (tobacco budworm, TBW), *Spodoptera exigua* (Hübner) (beet armyworm, BAW), *Manduca sexta* (Linnaeus) (tobacco hornworm, THW), and *Ostrinia nubilalis* (Hübner) (European corn borer, ECB). The artificial diet used to bioassay SCR was as described in Rose, R. I. & J. M. McCabe (1973), "Laboratory rearing techniques for the southern corn rootworm," *J. Econ. Entomol.* 66(2): 398–400. The Multiple Species Diet (Southland Products, Inc., Lake Village, Ark.) was used in bioassays with ECB, CEW, TBW, and THW.

Samples were bioassayed by applying 40 µL aliquots of each sample directly to the surface of the artificial diet (~1.5 cm$^2$) in 8 or 16 wells of a 128-well bioassay tray (BIO-BA-128, CD International, Pitman, N.J.). Treated diet wells were allowed to dry under a constant air flow in a biological safety cabinet, then each well was infested with a single, neonate insect hatched from surface sterilized eggs. Assay trays were sealed with a vented lid (BIO-CV, CD International), then placed in an environmentally controlled chamber [28° C., relative humidity of 40%, photoperiod of 16:8 (L:D)] for the duration of the assay. Mortality and growth inhibiton were assessed after 3–5 days.

Insect Bioassay of Expressed Toxin

Complex Genes. The biological activity of expressed toxin complex genes was tested in insect feeding assays. These assays were performed as described previously except that the artificial diets used were modified from those described by Marrone, P. G., F. D. Ferri, T. R. Mosely, & L. J. Meinke (1985), "Improvements in laboratory rearing of the southern corn rootworm, *Diabrotica undecimpunctata howardi* Barber (Coleoptera: Chrysomelidae), on artificial diets and corn," *J. Econ. Entomol.* 78(1):290–293, and King, E. G. & G. G. Hartley (1985), page 323 in P. Singh & R. F. Moore [eds.], *Handbook of Insect Rearing*, vol. 2, Elsevier, New York, and that mortality and growth inhibition were assessed after 5–7 days.

EXAMPLE 2

Purification and Initial Sequencing of an Insecticidal Toxin from *Xenorhabdus* Strain Xwi In summary, proteinaceous insecticidal actives with oral activity against Lepidoptera were biochemically-purified from *Xenorhabdus* strain Xwi and was designated as Toxin$_{XwiA}$. The purified active had an apparent native molecular weight of about 860 kDa as determined by gel filtration column chromatography. When examined by SDS-PAGE analysis, a Coomassie-staining band>220 kDa was observed for the purified toxin. These data indicate that the native toxin may exist as a tetramer of>220 kDa monomers. When tested for oral insecticidal activity in insect bioassay, this purified toxin exhibited mortality and/or growth inhibition against THW, TBW, CEW, and BAW.

More specifically, five liters of filter-sterilized of *Xenorhabdus* strain Xwi fermentation broth were concentrated using an Amicon (Beverly, Mass.) spiral ultrafiltration cartridge Type S1Y100 (100 kDa molecular weight cut off) attached to an Amicon M-12 filtration device according to the manufacturer's recommendations. The retentate material was diafiltered with 10 mM sodium phosphate, pH 7.0 (hereafter referred to as Buffer A) and applied at 5 mL/min to a Q Sepharose XL anion exchange column (1.6×10 cm, Amersham Biosciences Corp., Piscataway, N.J.). [For this and subsequent protein purification steps, all operations were performed at room temperature unless otherwise noted.] The column was washed with 5 bed volumes of Buffer A to remove unbound proteins. Protein fractions containing the THW activity were eluted by 0.4 M NaCl in Buffer A and loaded onto a gel filtration column (2.6×100 cm) of Sepharose CL-4B previously equilibrated with Buffer A. Protein was eluted in Buffer A at a flow rate of 0.75 mL/min. An activity peak against THW eluted between retention times 320 min to 450 min. Protein fractions with THW activitywere pooled and further purified.

The pooled protein fractions were applied at a flow rate of 1 mL/min to a Mono Q column (1.0×10 cm, Amersham Biosciences Corp.) previously equilibrated with 20 mM Tris-HCl, pH 7.0 (hereafter referred to as Buffer B). Bound proteins were eluted by a linear gradient of 0 to 1 M NaCl in Buffer B at 2 mL/min for 60 min. Two mL fractions were collected and THW activity was determined by testing a dilution series of each fraction in insect bioassay.

Solid $(NH_4)_2SO_4$ was added to those protein fractions containing THW activity to a final concentration of 1.7 M. The fractions were then applied at 1 mL/min to a phenyl- Superose column (1.0×10 cm, Amersham Biosciences Corp.) previously equilibrated with 1.7 M $(NH_4)_2SO_4$ in 50 mM potassium phosphate buffer, pH 7.0 (hereafter referred to as Buffer C). After washing the column with 10 mL of Buffer C, bound proteins were eluted with a linear gradient Buffer C to 5 mM potassium phosphate, pH 7.0 at 1 mL/min for 120 min. Protein fractions were then dialyzed overnight against Buffer A.

The protein fractions were assayed for THW activity and the most active fractions were pooled and applied at 1 mL/min to a Mono Q column (0.5×5 cm) that was previously equilibrated with Buffer B. Bound proteins were eluted at 1 mL/min by a linear gradient of 0 to 1 M NaCl in Buffer B.

The molecular weight of the purified insecticidal protein was examined by a gel-filtration column containing Superdex S-200, and it appeared to have a native molecular weight of approximately 860 kDa. SDS-PAGE analyses of this insecticidal protein showed a predominant Coomassie blue staining band of estimated size >220 kDa. The purified toxin was designated as $Toxin_{XwiA}$.

The $LD_{50}$s of $Toxin_{XwiA}$ were determined to be as follows: 50 $ng/cm^2$ against THW, 100 $ng/cm^2$ against ECB, 250 $ng/cm^2$ against TBW, and >1,000 $ng/cm^2$ against CEW.

The amino acid sequences of the N-terminal and some internal peptides of $Toxin_{XwiA}$ are given below. These sequences were obtained as described below.

N-terminal and internal amino acid sequence analysis of *Xenorhabdus* toxins. To facilitate the cloning and characterization of nucleotide sequences encoding insecticidal toxins, N-terminal and internal amino acid sequences were obtained for some of the toxin peptides identified. Two methods for the determination of amino acid sequences of the highly purified *Xenorhabdus* protein toxins are described.

N-terminal Sequence Analysis. Proteins described herein were electrophoresed by SDS PAGE and transblotted to Immuno Blot™ PVDF Membrane (Bio-Rad Laboratories, Hercules, Calif.). Proteins of interest were localized on the membrane by staining with 1×Amido Black Staining Solution (0.1% (w/v) amido black, 25% (v/v) isopropanol, and 10% (v/v) acetic acid, Sigma Chemical Co., St. Louis, Mo.) for approximately 3 min at room temperature followed by partial destaining in several changes of distilled water. The bands of interest were excised from the membrane and subjected to Edman degradation for amino acid sequence analysis at the Harvard University Microchemistry Facility (Cambridge, Mass.). The N-terminal sequences obtained for insecticidal protein toxins purified from *Xenorhabdus* Xwi are listed below.

Internal Peptide Sequence Analysis. Purified insecticidal protein toxins were resolved by SDS-PAGE, excised from gels, digested 'in-situ' with trypsin, and analyzed by MALDI-TOF . Approximately one picomole of the proteolytic digest was mixed with the matrix solution (α-cyano-4-hydroxycinnamic acid), and then air-dried. Positive-ion post source decay (PSD) MALDI-TOF MS was performed using a Voyager DE™-STR equipped with a delayed-extraction system (PerSeptive Biosystems, Framingham, Mass.) with a 3 meter flight tube in the reflectron mode. A specific peptide mass was analyzed from a mixed population of peptide masses by utilizing a timed ion selector. Fragment ions were generated as a result of metastable decay. The segments of the product ion spectra, measured successively at each potential on the reflectron, are stitched together to create a complete product ion spectrum. Internal amino acid sequences of insect active proteins from strain Xwi was determined by MALDI-PSD and are listed below.

| Derived N-terminal sequences of insecticidal protein purified from *Xenorhabdus* strain Xwi | | | |
|---|---|---|---|
| Purified toxin | Peptide size (kDa) | N-terminal sequence | Sequence ID No. |
| $Toxin_{XwiA}$ | 220 | MYSTAVLLNKISPTRDGQTM | 1 |

| Internal amino acid sequences of $Toxin_{XwiA}$ determined by MALDI-PSD MS | | |
|---|---|---|
| Purified Toxin | Amino Acid Sequence | Sequence ID No. |
| $Toxin_{XwiA}$ | MWYVR | 2 |
| $Toxin_{XwiA}$ | LTQFLR | 3 |
| $Toxin_{XwiA}$ | ANPQLSGAIR | 4 |
| $Toxin_{XwiA}$ | LLDQLILR | 5 |

EXAMPLE 3

Construction and Screening of Genomic Cosmid Libraries of *Xenorhabdus* Strains

As a prerequisite for the production of *Xenorhabdus* insect toxin proteins in heterologous hosts, and for other uses, it is necessary to isolate and characterize the genes that encode those peptides. One cloning approach is based on the use of N-terminal and internal amino acid sequence data to design degenerate oligonucleotides for use as hybridization probes, or in amplification reactions by polymerase chain reaction (PCR). Another approach, described in this example, involves the construction of a cosmid library and screening for heterologous expression of insect toxin proteins in an insect bioassay.

Isolation of total cellular DNA from *Xenorhabdus*. *Xenorhabdus* strain Xwi was grown on PP3 agar containing 0.0025% bromthymol blue for 72 hours at 28° C. A single bromthymol blue-adsorbing colony was selected and used to inoculate 500 mL tri-baffled flasks containing 175 mL of PP3. Shake flasks were shaken at 150 rpm and incubated at 28° C. for approximately 24 hrs. Fifty mL of this culture was centrifuged at 2,400×g to pellet the cells. The supernatant fluid was removed and the cell pellet was frozen at -20° C. until it was thawed for total cellular DNA isolation.

Total cellular DNA was isolated from the :strain using a Genomic DNA purification kit (Qiagen Inc., Valencia, Calif.). Frozen bacterial cell pellets were resuspended in 1 l mL of Buffer B1 (50.mM Tris/HCl, pH 8.0; 50 mM EDTA, pH 8.0; 0.5% Tween 20,0.5% Triton X-100) containing 11 μL of Qiagen RNase A solution (100 mg/mL) by vortexing. To this suspension, 300 μL of a lysozyme (100 mg/mL; Sigma Chemical Co.) stock solution and 500 μL of a proteinase K (50 mg/mL; Sigma Chemical Co.) stock solution were added. The suspension was mixed by vortexing and incubated at 37° C. for 30 min. Four mL of Buffer B2 (3 M guanidine HCl; 20% Tween 20) was added to the bacterial lysates and mixed into solution by gentle inversion of the tubes. The bacterial lysates were incubated at 50° C. for 30 min. Total cellular DNA was isolated from the bacterial lysates using Qiagen Genomic-tip 500/G tips as per manufacturer's instructions (Qiagen Genomic DNA Handbook). The resulting purified DNA was dissolved in 500 L TE buffer (10 mM Tris/HCl pH 8.0; 1 mM EDTA pH 8.0) and stored at 4° C.

Construction of cosmid libraries. Partial Sau3A I digests were made of the total cellular DNA isolated from the *Xenorhabdus* strain based on section 3.1.3 of Ausubel et al. (*Current Protocols in Molecular Biology*, John Wiley and Sons, Inc., New York, N.Y.). 400 µg of *Xenorhabdus* total cellular DNA was incubated with 9 units of Sau3A I (Invitrogen, Carlsbad, Calif.) for 15 min at 37° C. in 800 µL total volume of 1×React 4 Buffer (supplied as 10× by the manufacturer). The reaction was heated at 65° C. for 20 min to inactivate the enzyme. The partially digested *Xenorhabdus* total cellular DNA was dephosphorylated by incubating with 20 units of shrimp alkaline phosphatase (Roche Molecular Biochemicals, Indianapolis, Ind.) for 2 hrs at 37° C. in 1.2 mL total volume of 1×SAP buffer (supplied as 10× by the manufacturer). The dephosphorylated insert DNA was mixed with an equal volume of an equilibrated phenol-chloroform (50:50; v/v) solution, mixed by gentle inversion, centrifuged at 14,000×g for 15 min, and the aqueous phase was removed and mixed with an equal volume of a chloroform-isoamyl alcohol (24:1; v/v) solution. After mixing the two phases by gentle inversion, the solution was centrifuged at 14,000×g for 15 min, the aqueous phase was removed to a fresh tube, and 0.1 volume of 3 M sodium acetate (pH 5.2) was added. Two volumes of ice-cold 100% ethanol were added and the solution was mixed by inversion. and placed at −70° C. overnight. DNA was pelleted by centrifugation at 14,000×g for 20 min, and the DNA pellet was resuspended in 50 µL double-distilled water and stored at −20° C.

Cosmid vector SuperCos 1 (Stratagene, La Jolla, Calif.) was prepared as recommended by the manufacturer. Insert DNA was ligated [20 units of T4 DNA Ligase (New England BioLabs Inc., Beverly, MA) overnight at 16° C. in 1×T4 DNA Ligase Buffer (supplied as 10× by manufacturer)] into the BamHI site of SuperCos I using a 3:1 ratio of partially-digested insert to vector DNA. Ligation mixtures were packaged using Gigapack III Gold Packaging Extract (Stratagene) and recombinant phage were titered using *Escherichia coli* strain XL1-Blue MR cells as described in the supplier's instructions. Library source plates were prepared from aliquots (20–40 µL) of the recombinant phage plus host cell culture spread onto LB agar (10 g/L Bacto-tryptone, 10 g/L NaCl, 5 g/L Bacto-yeast extract, 15g/L Bacto agar; Difco Laboratories) containing ampicillin (100 mg/L; Sigma Chemical Co.) and incubated overnight at 37° C. Master plates of the cosmid libraries for freezer storage were prepared from single colonies inoculated into individual wells of sterile 96-well microwell plates containing 100–1000 µL of Terrific Broth (TB media: 12 g/L Bacto-tryptone, 24 g/L Bacto-yeast extract, 0.4% v/v glycerol, 17 mM $KH_2PO_4$, 72 mM $K_2HP_2O_4$) plus either 100 ampicillin or 50 mg/L kanamycin (Sigma Chemical Co.), incubated without shaking overnight at 37° C. Copy plates from the master plates were made using a 96-well microplate replicator (V & P Scientific, Inc., San Diego, Calif.) to inoculate wells of a sterile 96-well microplate containing 100–1000 µL of LB broth containing 100 mg/L ampicillin. Copy plates were incubated without shaking at 37° C. overnight. For both master and copy plates, an equal volume (100–1000 µL) of filter-sterilized TB:glycerol or LB:glycerol (1:4; v:v) was added to the plates and the cultures and glycerol solutions were mixed using a multichannel pipetter. Plates were sealed with Biomek Seal and Sample aluminum foil lids (Beckman Instruments, Inc., Fullerton, Calif.) and placed at −70° C. for storage.

The average insert size of selected recombinant cosmids was assessed by isolating cosmid DNA using the NucleoSpin Nucleic Acid Purification Kit (CLONTECH Laboratories, Inc., Palo Alto, Calif.). The recovered DNA was digested with 20 units of Eco RI (New England BioLabs) for 1 hr at 37° C. and fragments were separated through a 1.0% agarose gel. DNA fragments were visualized with UV light following 0.5% ethidium bromide (Sigma Chemical Co.) staining and the relative sizes of fragments were estimated by comparison with 1 Kb DNA ladder (Invitrogen). Average insert size of individual cosmids ranged from 30–45 Kb.

Screening of cosmid libraries and identification of cosmids expressing insecticidal activity. Fresh cultures of the cosmid libraries were screened in insect bioassay to identify clones that expressed insecticidal activity. Copy plates of the libraries were removed from storage at −70° C. and thawed at 25° C. A 96-well microplate replicator was used to inoculate wells of a sterile 96-well microwell plate containing 2 mL of LB broth containing 100 mg/L ampicillin. The newly-inoculated plates were incubated without shaking at 28° C. for 2 days. Cell pellets of the cultures were obtained by centrifugation of the plates at 2,200×g for 1 hr. After centrifugation, 1.8 mL of the supernatant fluid was removed and the cell pellet was resuspended in the remaining supernatant fluid (approximately 200 µL). This process concentrated the cell pellet about 10×relative to the original culture.

As shown previously, culture broths from *Xenorhabdus* strain Xwi showed differential insecticidal activity (mortality and/or growth inhibition) against a number of insects from the orders Coleoptera, Diptera, Arcina, and Lepidoptera. Recombinant cosmids that expressed insecticidal activity against THW larvae (Lepidoptera) were identified by testing aliquots of the concentrated cell pellets in an insect bioassay. Concentrated cell pellets of the recombinant cosmid clones were applied directly to the surface (approximately 1.5 $cm^2$) of Multiple Species Diet in 40–100 µL aliquots. Experimental controls included in the assays and treated analogously were: LB media plus 100 mg/L ampicillin; and concentrated cell pellets of the *E. coli* host strain XL1-Blue MR containing the SuperCos I vector without insert. The diet plates were allowed to air-dry in a sterile flow-hood and each well was infested with two neonate THW larvae. The plates were sealed, placed in a humidified growth chamber and maintained in the dark at 27° C. Mortality and visible growth inhibition relative to control treatments were scored after 5–7 days of incubation. Generally, 8 larva (4 wells containing two insects each) per treatment were assayed. Approximately 600–1200 recombinant clones were screened from each of the cosmid libraries tested.

Spectrum of activity of recombinant cosmid clones expressing insecticidal activity. The spectrum of insecticidal activity encoded by the clones identified in the cosmid screening was assayed against THW, TBW, CEW, ECB, and BAW using concentrated cell pellets of the clones, prepared and tested as described for the library screening. These assays showed that the recombinant cosmid clones obtained from the Xwi cosmid libraries had insecticidal activity (mortality and/or growth inhibition) against all species of insects tested (Table 4).

TABLE 4

Observed Insecticidal Activity of Recombinant Cosmid Clones

| Xenorhabdus cosmid library | Cosmid clone designation | Sensitive* insect species |
|---|---|---|
| Xwi | 8C3 (pDAB2097) | 1, 2, 3, 4, 5 |
| Xwi | 6A2 | 1, 2, 3, 4, 5 |

*> or = 30% mortality and/or growth inhibition relative to control
1 = THW;
2 = TBW;
3 = CEW;
4 = ECB;
5 = BAW

EXAMPLE 4

Analysis of Insert DNA Contained in the Recombinant Cosmid pDAB2097

To determine the open reading frame(s) (ORFs) responsible for the insecticidal activity observed from the recombinant cosmid pDAB2097 isolated in Example 3, the nucleotide sequence of the insert DNA in this cosmid was determined and analyzed.

Nucleotide Sequencing of pDAB2097 Insert DNA. Cosmid DNA was purified according to manufacturer's instructions using a NucleoSpin Nucleic Acid Purification Kit (CLONTECH). The DNA was partially digested in a series of enzyme dilutions as described in section 3.1.3 of Ausubel et al. (ibid.) to fragments ranging in size from 800–1,800 bp. Digestion reactions consisted of 20–40 µg cosmid DNA with 10 units/µL of diluted restriction enzyme HinPI (New England BioLabs) in 1×NEBuffer 2 (supplied as a 10×stock by the manufacturer) at 37° C. for approximately 12 minutes. Following incubation, reactions were heat inactivated by incubation at 65° C. for 30 minutes. Partial digests were gel purified using an 0.8% agarose gel (Invitrogen) and fragments were excised from the gel and purified using a QIAEX II Gel Extraction Kit, as described by the manufacturer (Qiagen).

Bacteriophage M13mp19RF vector (Roche Molecular Biochemicals) was prepared by completely digesting 5 µg of DNA with restriction enzyme AccI (10 units/µL) (New England BioLabs) in 1×NEBuffer 4 (supplied as a 10×stock by the manufacturer) at 37° C. The reaction was heat inactivated at 65° C. for 30 minutes, then the DNA was dephosphorylated using 1 unit of shrimp alkaline phosphatase (SAP) (Roche Molecular Biochemicals) in 1×SAP buffer (supplied as a 10×stock by the manufacturer) and incubation for 1 hr at 37° C. The vector DNA was then extracted once with 1 volume of phenol:chloroform:isoamyl (25:24:1; v/v/v) and once with 1 volume of chloroform: isoamyl (24:1; v/v) before precipitation by adding 0.1 volume of 3 M sodium acetate (pH 5.2) and 2 volumes of 100% ethanol, and incubating in a dry ice/ethanol bath for 30 minutes. The precipitated vector was spun at 14,000×g and the pellet washed with 1 volume of 70% ethanol before resuspending in 10 µL of distilled sterile water.

Partially digested HinPI cosmid fragments (0.2 µg) were ligated to AccI digested, dephosphorylated M13mp19RF fragments (0.2 µg) using 20 units of T4 DNA Ligase (New England BioLabs) in 1×T4 DNA Ligase Buffer with overnight incubation at room temperature. The ligation reaction was ethanol precipitated with 0.1 volume of 3 M sodium acetate (pH 5.2) and 2.5 volumes of 100% ethanol, then resuspended in a final volume of 20 µl TE buffer.

Transformation of host E. coli cells (electrocompetent XL1-Blue MRF', Stratagene) by electroporation was performed using a Bio-Rad Gene Pulser (200 ohms, 25 µF, 1.25 V) and 0.1 cm cuvette (Bio-Rad). Prior to transformation, 5 µL of ligation reaction mixture was added to 50 µL cells and incubated on ice. Immediately following electroporation, 1 mL of YT Broth [8 g/L Bacto tryptone, 5 g/L Bacto yeast extract, 5 g/L NaCl; pH 7.0] was added directly to the cuvette and then transferred to a 1.7 mL Eppendorf tube. Cells were pelleted by centrifuging for 30 sec at 10,000×g and the supernatant fluid was removed. Cells were resuspended in 1 mL YT Broth and repelleted by centrifuging for 30 sec at 10,000×g. The supernatant fluid was removed and the pelleted cells were resuspended in 200 µL YT Broth. Following a 1 hr recovery period at 37° C., the transformed cells were diluted and mixed with 50 µL XL1-Blue MRF' E. coli. This mixture was plated onto YT agar supplemented with X-gal (40 mg/L), IPTG (12 mg/L) and tetracycline (25 mg/L), and incubated overnight at 37° C. Clear phage plaques were then picked and used to infect XL1-Blue MRF' E. coli. Phage DNA was isolated using 20% PEG 8000 and 2.5 M NaCl precipitation. M13mp19RF vector containing cosmid DNA fragments were recovered by normal miniprep plasmid isolation from the remaining E. coli pellet (Sambrook, J., et al., 1989). The recovered phage and plasmid were used as templates in dye terminator cycle sequencing reactions using the DNA Sequencing Kit with AmpliTaq® DNA Polymerase, FS and protocols supplied with the PRISM™ sequencing kit (ABI/Perkin Elmer, Great Britain). Reaction primers were pUC/M13 reverse (17-mer) and pUC/M13 forward (17-mer) (Promega, Madison, Wis.). All sequencing reactions were incubated in a Perkin-Elmer 9600 Thermal Cycler. With phage DNA as template, the thermocycler parameters were: 5 cycles of 95° C. for 4 sec; 55° C. for 10 sec; and 70° C. for 60 sec, followed by 10 cycles of 95° C. for 4 sec and 70° C. for 60 sec. For plasmid DNA as template, the thermocycler parameters were: 25 cycles of 96° C. for 30 sec; 50° C. for 15 sec, and 60° C. for 4 min. The DNA sequence was obtained analysis of the DNA samples on an ABI Model 377 DNA Sequencer (ABI/Perkin Elmer).

The resulting sequence data were sorted and aligned using the Sequencher software package (Version 3.1.1; Gene Codes Corporation, Ann Arbor, Mich.). Gaps in the alignment of sequence contigs or second strand sequence reactions were solved through direct primer design and walking using cosmid DNA or a subclone derivative as template. All oligonucleotides were synthesized using a 394 DNA/RNA Synthesizer (ABI/Perkin Elmer). Double stranded nucleotide sequence was obtained for the entire insert contained in the pDAB2097 recombinant cosmid. PHRED-PHRAP analysis software (University of Washington, Seattle, Wash., USA) was used to assess the quality of the double-stranded sequence determined for the entire 39 kb insert contained in cosmid pDAB2097. Nucleotide positions that had quality scores <15 were resolved by repeated sequencing with the standard M13/pUC primers or with specifically designed primers, until high quality nucleotide sequence was obtained.

Nucleotide sequence analysis of the pDAB2097 insert DNA. The 39,005 bp sequence obtained from the pDAB2097 cosmid (SEQ ID NO. 6) was analyzed using the Vector NTI™ Suite (Informax, Inc. North Bethesda, Md., USA) to identify encoded ORFs (Open Reading Frames). Six full length ORFs and one partial ORF were identified (FIG. 1 and Table 5).

TABLE 5

ORFs identified in the pDAB2097 cosmid insert

| ORF Designation | ORF Position in SEQ ID NO. 13 | SEQ ID NO. (Nucleotide) | No. of Deduced Amino Acids | SEQ ID NO. (Amino Acid) |
|---|---|---|---|---|
| ORF1 | 1–1,533 | 7 | 511 | 8 |
| ORF2 | 1,543–5,715 | 9 | 1,391 | 10 |
| ORF3 | 5,764–7,707 | 11 | 648 | 12 |
| ORF4 | 10,709–18,277 | 13 | 2,523 | 14 |
| ORF5 | 18,383–21,430 (C*) | 15 | 1,016 | 16 |
| ORF6 | 21,487–25,965 (C) | 17 | 1,493 | 18 |
| ORF7 | 26,021–33,634 (C) | 19 | 2,538 | 20 |

*(C) designates complementary strand of SEQ ID NO: 6

The nucleotide sequences of the identified ORFs and the deduced amino acid sequences encoded by these ORFs were used to search the databases at the National Center for Biotechnology Information by using BLASTn, BLASTp, and BLASTx, via the ".gov" (government) website of ncbi/nih for BLAST. These analyses showed that the ORFs identified in the pDAB2097 insert had significant amino acid sequence identity to genes previously identified in *Photorhabdus luminescens* and *Xenorhabdus nematophilus* (Table 6). It is noteworthy that the xpt gene sequences presented in GenBank accession number AJ308438 were obtained from a recombinant cosmid that expressed oral insecticidal activity.

TABLE 6

Similarity of Deduced Proteins encoded by pDAB2097 ORFs to Known Genes

| pDAB2097 ORF* (deduced amino acids) | Gene/ORF Designation (GenBank Accession) | % Amino Acid Sequence Identity to Database Match |
|---|---|---|
| ORF1 (1–511) | tccA (AF047028) | 21.4% |
| ORF2 (313–1,391) | xptD1 (AJ308438) | 96.6% |
| ORF3 (1–648) | chi (AJ308438) | 100% |
| ORF4 (1–2,523) | xptA1 (AJ308438) | 99.5% |
| ORF5 (1–1,016) | xptB1 (AJ308438) | 95.9% |
| ORF6 (1–1,402) | xptC1 (AJ308438) | 96.4% |
| ORF7 (1–2,538) | xptA2 (AJ308438) | 95.1% |

*Deduced Amino Acid Positions with Identity to Database Sequence

Since ORF2, ORF4, ORF5, ORF6, and ORF7 were shown to have at least 95% amino acid sequence identity to previously identified genes, the same gene nomenclature was adopted for further studies on the ORFs identified in the pDAB2097 insert sequence (Table 7).

TABLE 7

Nomenclature of ORFs identified in pDAB2097 insert sequence

| pDAB2097 ORF | Gene Designation |
|---|---|
| ORF2 | xptD1 |
| ORF4 | xptA1 |
| ORF5 | xptB1 |
| ORF6 | xptC1 |
| ORF7 | xptA2 |

From comparison of the deduced amino sequences of the xpt genes found in pDAB2097 with the biochemical data obtained from the characterization of $Toxin_{XwiA}$, it was concluded that xptA2 encodes the $Toxin_{XwiA}$ protein. The data supporting this conclusion are as follows (Table 8). First, the N-terminal sequence obtained for $Toxin_{XwiA}$ (SEQ ID NO. 1) exactly matches the first 20 amino acids encoded by xptA2. Second, the four internal amino acid sequences obtained from $Toxin_{XwiA}$ are found in the xptA2 deduced amino acid sequence.

TABLE 8

$Toxin_{XwiA}$ amino acid sequences found in the deduced amino acid sequence of xptA2

| Residue Position of Deduced XptA2 | Amino Acid Sequence from $Toxin_{XwiA}$ | SEQ ID NO. |
|---|---|---|
| 1–20 | MYSTAVLLNKISPTRDGQTM | 1 |
| 71–80 | ANPQLSGAIR | 4 |
| 1,890–1,897 | LLDQLILR | 5 |
| 1,915–1,919 | MWYVR | 2 |
| 2,386–2,391 | LTQFLR | 3 |

EXAMPLE 5

Purification and Characterization of Insecticidal Toxin Encoded by Cosmid pDAB2097

As described in Example 3, the recombinant cosmid clone pDAB2097 demonstrated insecticidal activity against THW, TBW, CEW, ECB, and BAW (Table 4). The nature of the insecticidal activity encoded by this cosmid was investigated by biochemical purification and characterization. Insect bioassay using THW, as described in Example 1, was used during the purification process to monitor the biochemical purification of insecticidal activities.

Concentrated cell pellets of *E. coli* cells harboring pDAB2097 were produced by processing 5 liters of fermentation broths prepared as follows. A single colony of the recombinant clone was inoculated into 1 L LB plus 100 µg/mL ampicillin in 2.8 L Fernbach flasks. Inoculated flasks were shaken on a rotary shaker at 150 rpm at 28° C. for 2 days, the cultures were dispensed into sterile 1.0 L polyethylene bottles, and then centrifuged at 12,400×g for 30 min at 4° C. Supernatant fluid was removed and discarded. Cell pellets were resuspended in 50 mM potassium phosphate buffer, pH 7.0 and lysed by mechanical disruption in a Bead Beater® Blender with 0.1 mm beads according to the manufacture's protocol. The cell debris was removed by filtering through cheesecloth and centrifugation at 27,000×g for 15 minutes at 4° C. The supernatant liquid was applied to a Q Sepharose XL anion exchange column (1.6×10 cm) at 5 mL/min, and bound proteins were then eluted with 30 mL of 20 mM Tris-HCl, pH 8.0, containing 0.5 M NaCl.

The protein fraction was loaded onto a gel filtration column (2.6×100 cm) of Sepharose CL-4B which was equilibrated with Buffer A. Proteins were eluted in Buffer A at a flow rate of 0.75 mL/min. Bioassays were performed on each fraction against THW. Active fractions were pooled and applied at a flow rate of 1 mL/min to a Mono Q column (1.0×10 cm) equilibrated with Buffer A.

The proteins bound to the column were eluted with a linear gradient of 0 to 1 M NaCl in Buffer A at 2 mL/min for 60 min. Two mL fractions were collected and activity was determined in a dilution series of each fraction in insect bioassay.

Solid ammonium sulfate was added to the above protein fractions to a final concentration of 1.7 M, and the solution was applied at 1 mL/min to a phenyl-Superose column (0.5×5 cm) equilibrated with 1.7 M $(NH_4)_2SO_4$ in 50 mM potassium phosphate buffer, pH 7.0 (Buffer B). After washing the column with 10 mL of Buffer C, proteins bound to the column were eluted with a linear gradient Buffer B to 5 mM potassium phosphate, pH 7.0 at 1 mL/min for 120 min. Fractions were dialyzed overnight against Buffer A. The most active fractions, as determined by bioassay on THW, were pooled and applied at 1 mL/min to a Mono Q column (0.5×5 cm) equilibrated with Buffer B. The proteins bound to the column were eluted at 1 mL/min by a linear gradient of 0 to 1 M NaCl in Buffer A.

The last step of the purification was accomplished by gel filtration through a Superdex 200 column (1.0×30 cm) which was pre-equilibrated with Buffer A. The active fractions were applied to the column at 0.5 mL aliquots and eluted with Buffer A at 0.5 mL/min.

SDS-PAGE analysis of the purified toxin from *E. coli* harboring cosmid pDAB2097 indicated a predominant peptide of about 220 kDa or more. The native molecular weight of the toxin complex, as determined by gel filtration, was approximately 860 kDa (which would be consistent with a tetramer of the predominant peptides). The purified protein having insecticidal activity, and encoded by the recombinant cosmid pDAB2097 (i.e. Xwi-8C3), was designated as Toxin$_{Xwi-8C3}$. The $LD_{50}$ for Toxin$_{Xwi-8C3}$ was determined to be approximately 300 ng/cm² against THW.

EXAMPLE 6

Characterization of Toxin$_{XwiA}$ and Toxin$_{Xwi-8C3}$ by MALDI-TOF Analysis

MALDI-TOF analysis was used to obtain information regarding the relationship between Toxin$_{XwiA}$ and Toxin$_{Xwi-8C3}$. For this analysis, peptide mass fingerprints were obtained for both Toxin$_{XwiA}$ and Toxin $_{Xwi-8C3}$, and these data were compared to a theoretical peptide mass fingerprint of the deduced amino acid sequence from ORF xptA2. To generate these peptide mass fingerprints, Toxin$_{XwiA}$ and Toxin$_{Xwi-8C3}$ were digested with trypsin and the mass of the resulting peptides was determined using mass spectroscopy. Such digestion with trypsin generates a specific peptide "fingerprint" for each purified toxin based upon the specific cleavage site of trypsin. Since the alteration of only a single amino acid residue can detectably alter the mass of a given tryptic peptide, the identification of common peptide masses between two fingerprints indicates a degree of amino acid sequence identity.

MALDI-TOF analysis of Toxin$_{XwiA}$ and Toxin$_{Xwi-8C3}$ Toxin$_{XwiA}$ and Toxin$_{Xwi-8C3}$ proteins were subjected to preparative 1-D separation in order to produce well-resolved, purified toxin proteins in quantities sufficient for peptide mass fingerprinting. A standard procedure for protein separation was followed (Laemmli, 1970), and purified protein was loaded in each well of 4–20% gradient sodium dodecyl sulfate polyacrylamide gel (SDS-PAGE; Owl Scientific Co., Mass.) for electrophoresis. Electrophoresis was conducted at constant 35 mA for 2 h. The proteins were visualized by staining in a solution of Coomassie Brilliant Blue R-250 (Bio-Rad).

Following separation of proteins by SDS PAGE, protein bands were excised from gels using a stainless steel scalpel and placed into a 1.5-mL polypropylene Eppendorf tube. After adding 0.7 mL of de-stain solution (50% acetonitrile in 25 mM $NH_4HCO_3$), gel pieces were crushed to <1 mm² using a Kontes Pellet Pestle™, followed by addition of another 0.7 mL of destain solution. Samples were shaken vigorously for 30 minutes and then centrifuged to pellet the gel pieces. The supernatant was discarded and subsequent de-stain steps were performed until gel pieces were translucent in color, at which time the gel pieces were dried under vacuum centrifugation for 15 minutes. Dried gel pieces were covered with a volume (15–20 µL per protein band) of trypsin (50 µg/mL in 25 mM $NH_4HCO_3$, pH 8.0) which allowed complete rehydration of the gel pieces. Proteolysis occurred for 16 hours at 37° C. Peptides were extracted with the addition of 0.3 mL of 50% acetonitrile in 0.5% trifluoroacetic acid (TFA), immediately followed by vigorous shaking for 1 hour. After brief centrifugation to pellet the gel pieces, the supernatant was saved in a siliconized 0.5-mL Eppendorf tube. Gel pieces were dried under vacuum centrifugation for 15 minutes. After rehydration with 0.1 mL of 0.5% TFA, the sample was placed in a sonication bath for 10 minutes. Then, 0.1 mL of acetonitrile was added, followed by vigorous shaking for 1 hour. After centrifugation, the supernatant was combined with the first extract and dried using vacuum centrifugation.

To determine peptide mass fingerprints of Toxin$_{XwiA}$ and Toxin$_{Xwi-8C3}$, peptides were solubilized with 10 µl of 0.1% TFA. Soluble peptides (0.6 µl) were mixed by pipetting with 0.6 µl of matrix solution (α-cyano-4-hydroxycinnamic acid, at 10 mg/mL in 50% acetonitrile in 0.5% TFA), placed onto the MALDI plate, and allowed to dry. Internal calibration was performed using autolyic trypsin peptide masses (m/z 805.41 and/or m/z 2163.05). Mass analyses were recorded on a PerSeptive Biosystems (Framingham, Mass.) Voyager DE™-STR delayed extraction time-of-flight reflectron mass spectrometer equipped with a nitrogen laser (337 nm). Mass spectra were collected in positive ion mode with the reflectron flight tube using the following instrument settings: 20 kV ion acceleration, grid voltage of 75%, guide wire voltage of 0.02–0.03%, and a low mass gate setting of 600.

Peptide mass fingerprint analysis of Toxin$_{XwiA}$ and Toxin$_{Xwi-8C3}$. MALDI-TOF MS analysis was used to compare the peptide mass fingerprints obtained for tryptic digests of purified Toxin$_{Xwi-8C3}$ protein prepared from *E. coli* cells harboring pDAB2097, the in silico tryptic digests predicted from the deduced amino acid sequence encoded by ORF xptA2, and the tryptic digests generated from the native protein Toxin$_{XwiA}$ (Table 9). Fifty-seven tryptic peptide masses of Toxin$_{XwiA}$ matched the in silico digest of the deduced amino acid sequence of XptA2. The relatively high number of matching peptide masses from the observed Toxin$_{XwiA}$ peptides and the theoretical deduced XptA2 peptides indicates that ORF xptA2 encodes the Toxin$_{XwiA}$ protein. Similarly, eleven peptide masses from Toxin$_{Xwi-8C3}$ matched both XptA2 theoretical tryptic masses and native Toxin$_{XwiA}$ tryptic masses (in bold type). These data indicate that the recombinant insecticidal activity purified from *E coli* harboring cosmid pDAB2097 (i.e. Toxin$_{Xwi8C3}$) is derived from expression of ORF xptA2, and that this cosmid encodes at least one of the proteins responsible for the insecticidal activity of the native Xwi strain.

TABLE 9

Comparison of observed tryptic peptide mass fingerprints of Toxin$_{XwiA}$ and Toxin$_{Xwi-8C3}$ with the in silico trypsin digest of deduced amino acid sequence from XptA2

| Residue # of XptA2 | Sequence | Seq ID # | Toxin$_{XwiA}$ Observed [M + H$^+$] | Toxin$_{Xwi-8C3}$ Observed [M + H$^+$] | XptA2 Theoretical [M + H$^+$] |
|---|---|---|---|---|---|
| 0016–0034 | DGQTMTLADLQYLSFSELR | 23 | 2188.05 | n.d.* | 2188.06 |
| 0035–0047 | KIFDDQLSWGEAR | 24 | 1564.74 | 1564.81 | 1564.78 |
| 0036–0047 | IFDDQLSWGEAR | 25 | 1436.67 | n.d. | 1436.68 |
| 0048–0057 | HLYHETIEQK | 26 | 1297.65 | n.d. | 1297.66 |
| 0071–0080 | ANPQLSGAIR | 27 | 1026.56 | n.d. | 1026.57 |
| 0091–0099 | SYDEMFGAR | 28 | 1075.43 | n.d. | 1075.45 |
| 0100–0124 | SSSFVKPGSVASMFSPAGYLTELYR | 29 | 2681.38 | n.d. | 2681.33 |
| 0128–0141 | DLHFSSSAYHLDNR | 30 | 1661.75 | n.d. | 1661.77 |
| 0194–0208 | QAIDTPYHQPYETIR | 31 | 1831.87 | 1831.88 | 1831.90 |
| 0209–0223 | QVIMTHDSTLSALSR | 32 | 1658.82 | n.d. | 1658.86 |
| 0369–0375 | EFGATLR | 33 | 793.41 | n.d. | 793.41 |
| 0416–0420 | IYAYR | 34 | 685.37 | n.d. | 685.37 |
| 0487–0496 | VFYTLFYSHR | 35 | 1332.67 | n.d. | 1332.68 |
| 0537–0558 | IFEADGNTVSIDPDEEQSTFAR | 36 | 2441.14 | n.d. | 2441.11 |
| 0628–0639 | TTASLSSGELPR | 37 | 1218.60 | n.d. | 1218.64 |
| 0797–0813 | NQPAGQHNIDTLFSLYR | 38 | 1973.97 | 1973.98 | 1973.99 |
| 0893–0898 | TLVNIR | 39 | 715.45 | n.d. | 715.45 |
| 0987–1000 | LAEAIAGIQLYINR | 40 | 1544.87 | 1544.82 | 1544.88 |
| 1017–1027 | QFFTDWTVNNR | 41 | 1427.65 | n.d. | 1427.67 |
| 1028–1036 | YSTWGGVSR | 42 | 1012.47 | 1012.49 | 1012.49 |
| 1037–1050 | LVYYPENYIDPTQR | 43 | 1770.86 | 1770.86 | 1770.87 |
| 1080–1092 | TYLTRFETVADLK | 44 | 1556.78 | n.d. | 1556.83 |
| 1093–1115 | VVSAYHDNVNSNTGLTWFVGQTR | 45 | 2565.20 | n.d. | 2565.25 |
| 1116–1124 | ENLPEYYWR | 46 | 1269.58 | 1269.62 | 1269.59 |
| 1143–1166 | EWTKIDTAVNPYKDAIRPVILRER | 47 | 2883.56 | n.d. | 2883.59 |
| 1165–1179 | ERLHLIWVEKEEVAK | 48 | 1879.05 | n.d. | 1879.05 |
| 1195–1199 | LAFLR | 49 | 619.39 | n.d. | 619.40 |
| 1277–1284 | MENTALSR | 50 | 921.48 | n.d. | 921.48 |
| 1290–1304 | NTFDIIHTQGNDLVR | 51 | 1742.87 | n.d. | 1742.89 |
| 1346–1363 | YSSDNLAITLHNAAFTVR | 52 | 1993.00 | n.d. | 1993.02 |
| 1364–1372 | YDGSGNVIR | 53 | 980.48 | n.d. | 980.48 |
| 1421–1437 | NYIASVQGHLMNADYTR | 54 | 1952.92 | n.d. | 1952.93 |
| 1438–1451 | RLILTPVENNYYAR | 55 | 1721.95 | n.d. | 1721.94 |
| 1593–1605 | RVNYNPEDILFLR | 56 | 1648.89 | n.d. | 1648.88 |
| 1594–1605 | VNYNPEDILFLR | 57 | 1492.76 | 1492.77 | 1492.78 |
| 1606–1620 | ETHSGAQYMQLGVYR | 58 | 1739.81 | n.d. | 1739.82 |

TABLE 9-continued

Comparison of observed tryptic peptide mass fingerprints
of Toxin$_{XwiA}$ and Toxin$_{Xwi-8C3}$ with the in silico trypsin
digest of deduced amino acid sequence from XptA2

| Residue # of XptA2 | Sequence | Seq ID # | Toxin$_{XwiA}$ Observed [M + H$^+$] | Toxin$_{Xwi-8C3}$ Observed [M + H$^+$] | XptA2 Theoretical [M + H$^+$] |
|---|---|---|---|---|---|
| 1635–1649 | ANTGIDTILTMETQR | 59 | 1663.77 | n.d. | 1663.83 |
| 1668–1677 | YDPAEHGDER | 60 | 1188.49 | n.d. | 1188.49 |
| 1681–1692 | IHIGNVGGNTGR | 61 | 1194.62 | n.d. | 1194.64 |
| 1885–1890 | IATFMR | 62 | 738.39 | n.d. | 738.39 |
| 1891–1898 | LLDQLILR | 63 | 983.62 | n.d. | 983.63 |
| 1999–2003 | LFNLR | 64 | 662.40 | n.d. | 662.40 |
| 2026–2050 | ALLTSMVQASQGGSAVLPGTLSLYR | 65 | 2520.36 | n.d. | 2520.35 |
| 2051–2057 | FPVMLER | 66 | 891.48 | n.d. | 891.48 |
| 2106–2121 | TVDEVDADIAVLAESR | 67 | 1702.77 | 1702.83 | 1702.85 |
| 2131–2145 | YQQLYDEDINHGEQR | 68 | 1907.82 | n.d. | 1907.85 |
| 2186–2191 | WGAALR | 69 | 673.38 | n.d. | 673.38 |
| 2220–2228 | RRQEWEIQR | 70 | 1300.66 | n.d. | 1300.69 |
| 2221–2228 | RQEWEIQR | 71 | 1144.57 | n.d. | 1144.59 |
| 2222–2228 | QEWEIQR | 72 | 988.44 | n.d. | 988.42 |
| 2281–2287 | ALYSWMR | 73 | 926.45 | n.d. | 926.46 |
| 2315–2325 | ELTDNGVTFIR | 74 | 1264.63 | 1264.61 | 1264.66 |
| 2352–2359 | VWLERDER | 75 | 1102.55 | n.d. | 1102.57 |
| 2387–2392 | LTQFLR | 76 | 777.46 | 777.45 | 777.46 |
| 2423–2435 | IFSDYPESLGNTR | 77 | 1498.69 | n.d. | 1498.72 |
| 2439–2455 | QVSVTLPALVGPYEDIR | 78 | 1857.01 | n.d. | 1857.01 |
| 2456–2468 | AVLNYGGSIVMPR | 79 | 1376.71 | n.d. | 1376.74 |

*n.d. = not detected

EXAMPLE 7

Expression of Toxin Complex Genes and Bioassay of TC Proteins from *Xenorhabdus* Xwi

Figure 2:
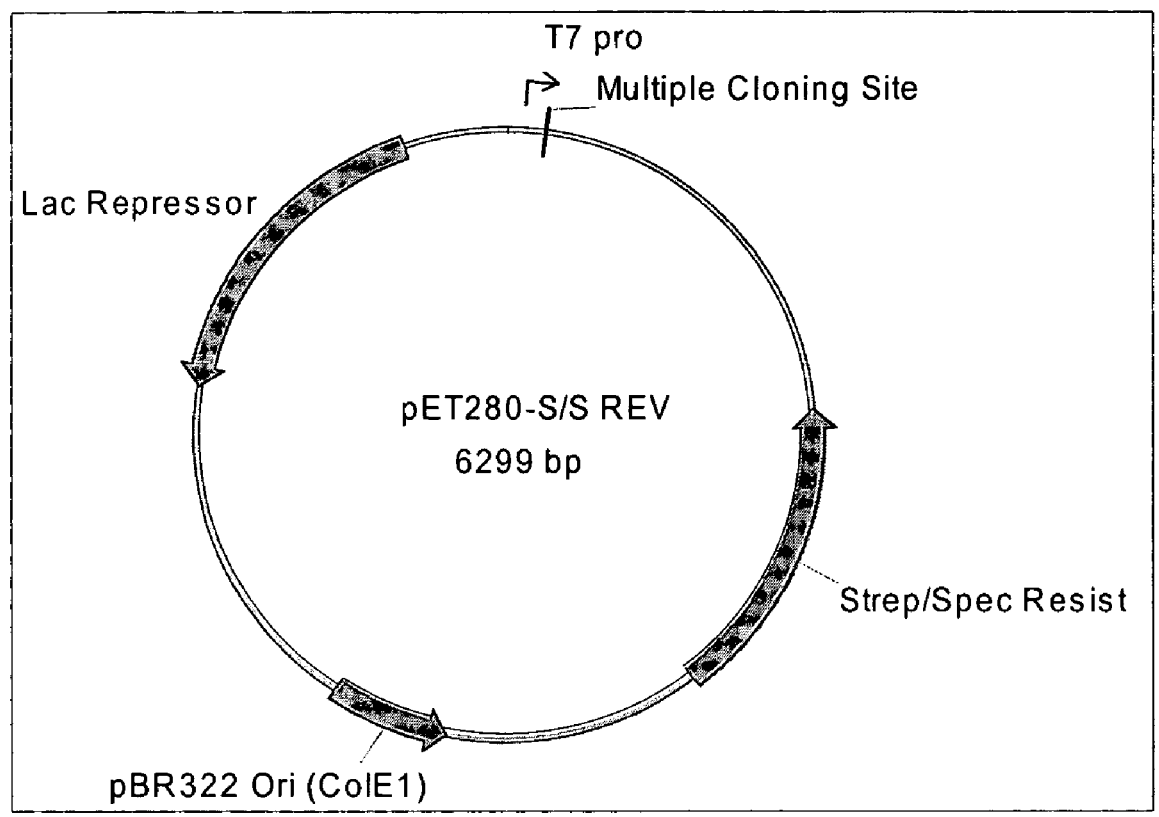
FIG. 2 shows expression vector plasmid pET280 vector.
Figure 3:
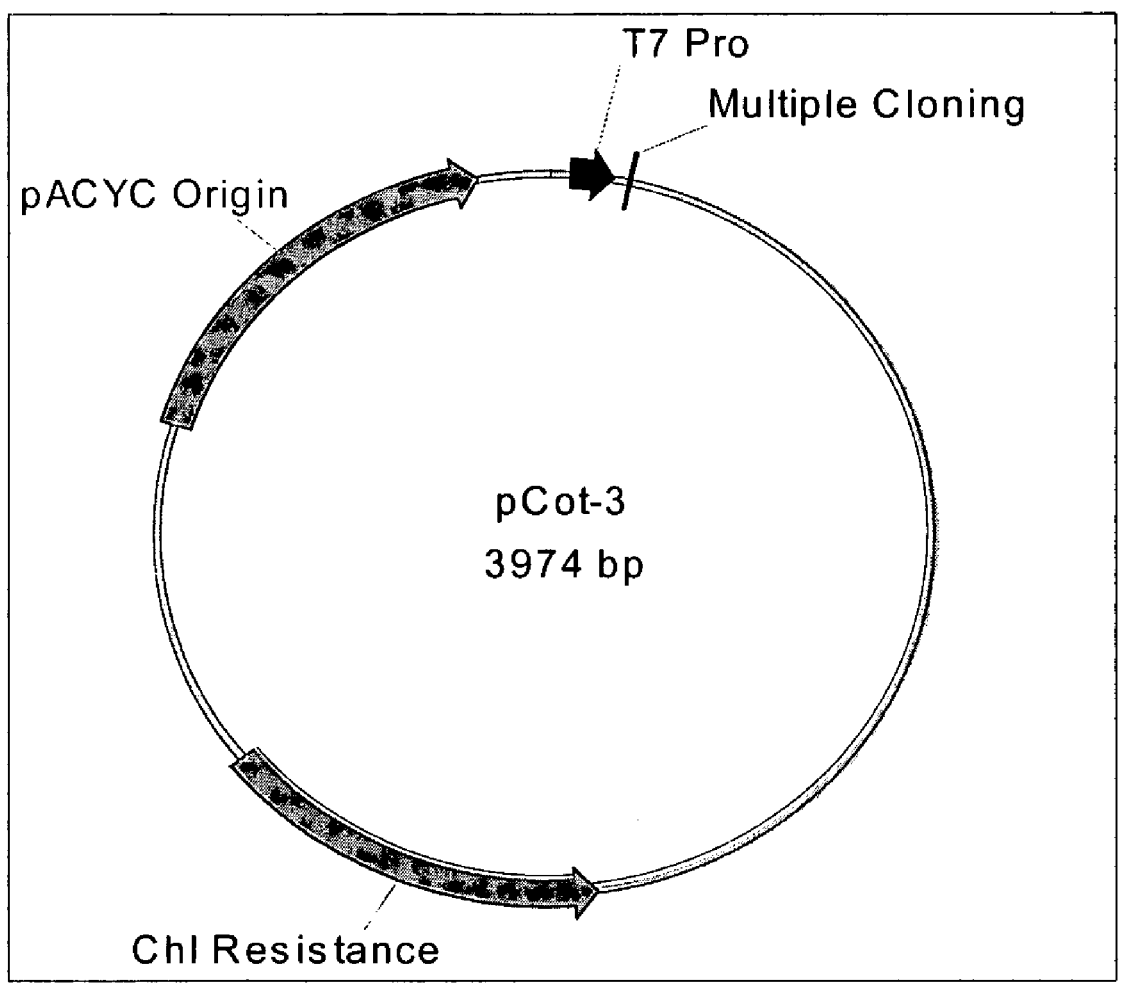
FIG. 3 shows expression plasmid pCot-3.
Figure 4:
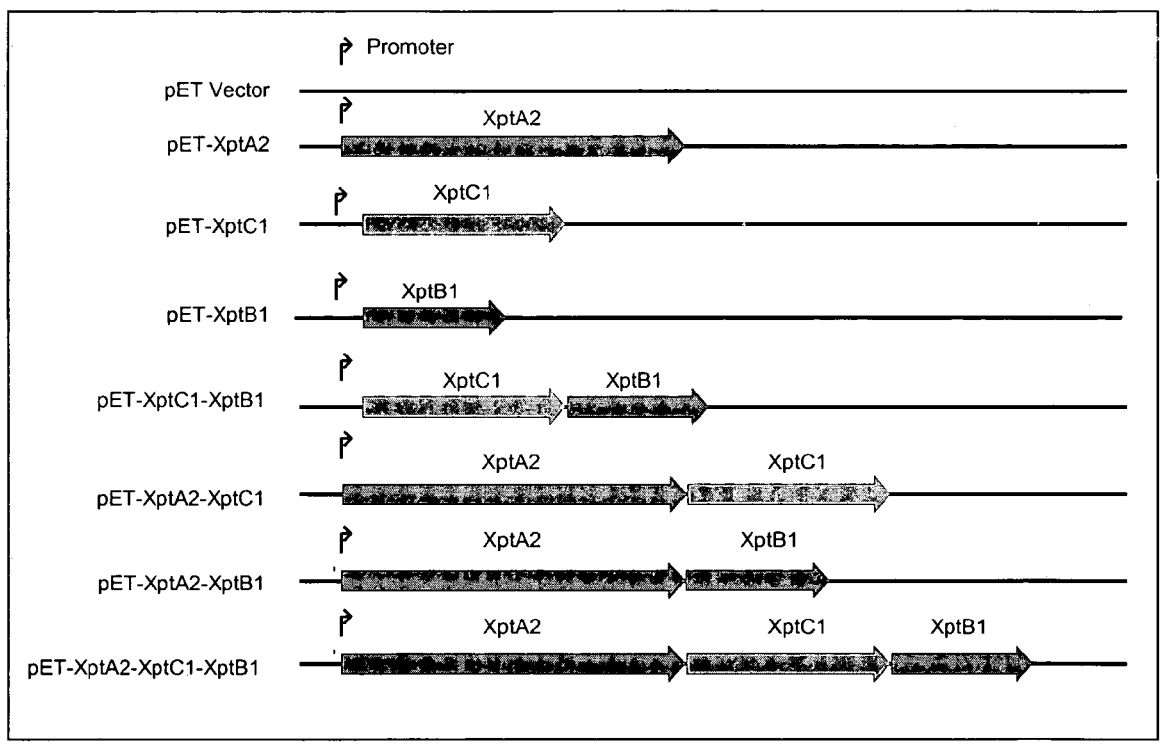
FIG. 4 is a schematic diagram of pET constructions.

*Xenorhabdus* Xwi genes were expressed in *E. coli*. Several plasmids were constructed in which polycistronic arrangements of up to three genes were constructed. Each gene contained a separate ribosome binding site and start codon, a coding sequence and a stop codon. The expression system was mediated by the strong T7 phage promoter and T7 RNA polymerase (FIG. 2, pET). Similarly, in some constructions polycistronic arrangements of coding sequences were used. Schematic diagrams describing constructions used in the experiments are shown in FIG. 4.

Construction of pET280-XptA2, pET280-XptC1, and pET280-XptB1. The coding sequences for the XptA2, XptC1, and XptB1 proteins were each PCR amplified from pDAB2097, a recombinant cosmid containing the three genes that encode these proteins (see Example 6). The PCR primer sets used to amplify these coding sequences are listed in Table 10. In all of these primer sets, the forward primer did not change the coding sequence of the gene but provided 5' non coding SalI and XbaI sites as well as a ribosome binding site. The reverse primers also did not alter the corresponding coding sequences, but provided a 3' XhoI cloning site. Following amplification with components of the EPICENTRE Fail Safe PCR kit, the engineered XptA2, XptC1, and XptB1 coding sequences were each cloned into pCR2.1. The cloned amplified products were sequence confirmed to ensure that PCR-induced mutations did not alter the coding sequences. Recombinant plasmids that contained unaltered coding sequences for XptA2, XptC1, and XptB1 were identified and designated as pDAB3056, pDAB3064, and pDAB3055, respectively. The coding sequences were each cut from the pCR2.1 derivatives and transferred to a modified pET vector via the 5' XbaI and 3' XhoI sites to create plasmids pET280-XptA2, pET280-XptC1, and pET280-XptB1. The plasmid pET280-SS is a modified pET28 (Novagen, Madison, Wis.) plasmid with the multiple cloning site replaced and a streptomycin/spectinomycin gene inserted into the backbone.

TABLE 10

PCR Primers Used to Amplify XptA2, XptC1, and XptB1 Coding Sequences

| Coding Sequence Amplified | Forward Primer Sequence (5'–3') | Reverse Primer Sequence (5'–3') |
|---|---|---|
| XptA2 | GTCTAGACGTGCGTCG ACAAGAAGGAGATATA CCATGTATAGCACGGC TGTATTACTCAATAAA ATCAGTCCCACTCGCG ACGG* (SEQ ID:80) | GCTCGAGATTAATTAA GAACGAATGGTATAGC GGATATGCAGAATGAT ATCGCTCAGGCTCTCC (SEQ ID NO:81) |
| XptC1 | GTCTAGACGTGCGTCG ACAAGAAGGAGATATA CCATGCAGGGTTCAAC ACCTTTGAAACTTGAA ATACCGTCATTGCCCT C (SEQ ID NO:82) | GACTCGAGAGCATTAA TTATGCTGTCATTTCA CCGGCAGTGTCATTTT CATCTTCATTCACCAC (SEQ ID NO:83) |
| XptB1 | GTCTAGACGTGCGTCG ACAAGAAGGAGATATA CCATGAAGAATTTCGT TCACAGCAATACGCCA TCCGTCACCGTACTGG ACAACC (SEQ ID NO:84) | GCTCGAGCAGATTAAT TATGCTTCGGATTCAT TATGACGTGCAGAGGC GTTAAAGAAGAAGTTA TT (SEQ ID NO:85) |

*Underlined sequences in primers correspond to protein coding sequences

Construction of pET280-XptA280-XptC1. Plasmid pET280-XptA2 DNA was cut with XhoI and ligated into the unique SalI site in pDAB3064. The resulting ligated product contained both pCR2.1 and pET280-SS vector backbones and could be recovered by antibiotic selection using a combination of streptomycin (25 µg/mL), spectinomycin (25 µg/mL), and ampicillin (100 µg/mL). DNA of the recovered plasmids was digested with XhoI to check fragment orientation. A plasmid with the XptC1 coding region immediately downstream of the XptA2 coding region was obtained and the DNA was digested with XhoI to remove the pCR2.1 vector backbone. The resulting construct, which contains the pET280-SS vector backbone and the coding sequences for XptA2 and XptC1, was self-ligated to produce pET280-XptA2-XptC1.

Construction of pET280-XptC1-XptB1. Plasmid pET280-XptC1 DNA was cut with XhoI and ligated into the unique SalI site in pDAB3055. The resulting ligated product contained both pCR2.1 and pET280-SS vector backbones and could be recovered by antibiotic selection using a combination of streptomycin (25 µg/mL), spectinomycin (25 µg/mL), and ampicillin (100 µg/mL). DNA of the recovered plasmids was digested with XhoI to check fragment orientation. A plasmid with the XptB1 coding region immediately downstream of the XptC1 coding region was obtained and the DNA was digested with XhoI to remove the pCR2.1 vector backbone. The resulting construct, which contains the pET280-SS vector backbone and the coding sequences for XptC1 and XptB1, was self-ligated to produce pET280-XptC1-XptB1.

Construction of pET280-XptA2-XptB1. Plasmid pET280-XptA2 DNA was cut with XhoI and ligated into the unique SalI site in pDAB3055. The resulting ligated product contained both pCR2.1 and pET280-SS vector backbones and could be recovered by antibiotic selection using a combination of streptomycin (25 µg/mL), spectinomycin (25 µg/mL), and ampicillin (100 µg/mL). DNA of the recovered plasmids was digested with XhoI to check fragment orientation. A plasmid with the XptB1 coding region immediately downstream of the XptA2 coding region was obtained and the DNA was digested with XhoI to remove the pCR2.1 vector backbone. The resulting construct, which contains the pET280-SS vector backbone and the coding sequences for XptA2 and XptB1, was self-ligated to produce pET280-XptA2-XptB1.

Construction of pET280-XptA2-XptC1-XptB1. Plasmid pET280-XptA2-XptC1 DNA was cut with XhoI and ligated into the unique SalI site in pDAB3055. The resulting ligated product contained both pCR2.1 and pET280-SS vector backbones and could be recovered by antibiotic selection using a combination of streptomycin (25 µg/mL), spectinomycin (25 µg/mL), and ampicillin (100 µg/mL). The recovered plasmids were digested with XhoI to check fragment orientation. A plasmid with the XptB1 coding region immediately downstream of the XptC1 coding region was obtained and the DNA was digested with XhoI to remove the pCR2.1 vector backbone. The resulting construct, which contains the pET280-SS vector backbone and the XptA2, XptC1, and XptB1 coding sequences, was self-ligated to produce pET280-XptA2-XptC1-XptB1.

Expression of T7-based constructions. The expression plasmids were transformed into E. coli T7 expression strain BL21(DE3) (Novagen, Madison, Wis.) cells and plated on LB agar containing a combination of streptomycin (25 µg/mL) and spectinomycin (25 µg/mL) and 50 mM glucose, and transformants were grown at 37° C. overnight. Approximately 10–100 well isolated colonies were used to inoculate 200 mL of sterile LB containing a combination of streptomycin (25 µg/mL) and spectinomycin (25 µg/mL) plus 75 µM isopropyl-β-D-thiogalatopyranoside (IPTG) in 500 mL baffled flasks. The cultures were shaken at 200 rpm at 28° C. for 24 hours: Cells were collected by centrifugation (approximately 3000×g) and resuspended in phosphate buffer (30 mM, pH 7.4; NutraMax; Gloucester, Mass.) to a cell density of 30–120 $OD_{600}$ units/mL. Diluted cells were then used for insect bioassay.

EXAMPLE 8

Insect Bioassay Results of Expressed Toxin Complex Genes

A series of expression experiments was performed using the pET expression system as described above. E. coli cells were transformed, induced and grown overnight at 28° C. The cells were collected, washed, normalized to equal concentrations, and tested for insecticidal activity against Ostrinia nubilalis European corn borer (ECB), corn earworm (CEW), and tobacco budworm (TBW). As shown in Table 11, the highest levels of insecticidal activity were observed when xptA2, xptC1, and xptB1 were present in the same construct.

TABLE 11

| Bioassay of Heterologously Expressed *Xenorhabdus* Toxin Complex Genes on TBW, CEW, and ECB | | | |
|---|---|---|---|
| Plasmid Tested | TBW Bioassay | CEW Bioassay | ECB Bioassay |
| pET-280-SS | 0* | 0 | 0 |
| pET-280-XptA2 | +++ | +++ | ++ |
| pET-280-XptC1 | 0 | 0 | 0 |
| pET-280-XptB1 | 0 | 0 | 0 |
| pET-280-XptA2-XptC1 | + | + | 0 |
| pET-280-XptA2-XptB1 | 0 | 0 | 0 |
| pET-280-XptC1-XptB1 | 0 | 0 | 0 |
| pET-280-XptA2-XptC1-XptB1 | +++++ | +++++ | +++++ |

*Whole *E. coli* cells were washed with phosphate buffer, concentrated, adjusted to equal cell concentrations, and applied to insect diet preparations.
Grading Scale represents % mortality and/or growth inhibition relative to controls
(0 = 0–10%;
+ = 11–20%;
++ = 21–40%;
+++ = 41–60% = ++++, 61–80%;
+++++ = 81–100%).

Further Bioassay Results. *E. coli* cells were co-transformed with the pET280 and pCoT constructs listed in Table 12. Transformants were induced, processed and bioassayed as described above. In these assays, co-transformants that contained pCOT/pET280-XptA2-XptC1-XptB1 plasmid combinations exhibited the highest levels of insecticidal activity.

TABLE 12

| Bioassay | |
|---|---|
| Plasmids Tested | CEW Bioassay |
| pET280/pCoT | 0* |
| pCoT/pET280-XptA2 | +++ |
| pCoT/pET280-XptA2-XptC1-XptB1 | +++++ |

*Whole *E. coli* cells were washed with phosphate buffer, concentrated, adjsuted to equal cell concentrations, and applied to insect diet preparations.
Grading Scale represents % mortality and/or growth inhibition relative to controls
(0 = 0–10%;
+ = 11–20%;
++ = 21–40%;
+++ = 41–60% = ++++, 61–80%;
+++++ = 81–100%).

The invention claimed is:

1. An isolated polynucleotide that encodes a protein that has toxin activity against an insect, wherein said protein comprises SEQ ID NO:20.

2. The polynucleotide of claim 1, wherein said polynucleotide comprises SEQ ID NO:19.

3. The polynucleotide of claim 1, wherein said polynucleotide comprises condons optimized for expression in a plant.

4. A transgenic plant that comprises the polynucleotide of claim 1.

5. The plant of claim 4, wherein said plant is selected from cotton plants, corn plants, and soybean plants.

6. A transgenic plant cell that comprises the polynucleotide of claim 1.

7. The plant cell of claim 6, wherein said plant cell is selected from a cotton plant cell, a corn plant cell, and a soybean plant cell.

8. A seed comprising the cell of claim 6.

9. A purified bacterial cell comprising the isolated polynucleotide of claim 1.

* * * * *

UNITED STATES PATENT AND TRADEMARK OFFICE
CERTIFICATE OF CORRECTION

PATENT NO. : 7,071,386 B2  Page 1 of 1
APPLICATION NO. : 10/753901
DATED : July 4, 2006
INVENTOR(S) : Scott B. Bintrim et al.

It is certified that error appears in the above-identified patent and that said Letters Patent is hereby corrected as shown below:

Column 4,
Line 28, "and tccc)." should read -- and *tccC*). --.

Column 14,
Line 62, "[1981] *ICA-UCLA*" should read -- [1981] *ICN-UCLA* --.

Column 20,
Line 29, "exon intronjunctions" should read -- exon:intron junctions --.

Column 32,
Line 48, "from the :strain" should read -- from the strain --.
Line 51, "(50.mM Tris/" should read -- (50 mM Tris/ --.
Line 52, "Tween 20,0.5% Triton" should read -- Tween 20, 0.5% Triton --.
Line 65, "in 500 L" should read -- in 500 µL --.

Column 33,
Line 54, "100 ampicillin" should read -- 100 mg/L ampicillin --.

Column 36,
Line 42, "obtained analysis" should read -- obtained by analysis --.

Column 45,
Line 43, "pET280-XptA280-XptC1." should read -- pET280-XptA2-XptC1. --.

Column 165, Claim 3,
Line 45, "condons" should read -- codons --.

Signed and Sealed this

Twenty-fifth Day of December, 2007

JON W. DUDAS
*Director of the United States Patent and Trademark Office*